United States Patent
Receveur et al.

(10) Patent No.: US 11,699,517 B2
(45) Date of Patent: Jul. 11, 2023

(54) ULTRA-WIDEBAND LOCATING SYSTEMS AND METHODS

(71) Applicant: Hill-Rom Services, Inc., Batesville, IN (US)

(72) Inventors: Timothy J. Receveur, Apex, NC (US); Frederick Collin Davidson, Apex, NC (US); Stephen R. Embree, Chapel Hill, NC (US); Britten J. Pipher, Raleigh, NC (US); Eric D. Agdeppa, Cincinnati, OH (US); Steven D. Baker, Beaverton, OR (US); Bradley T. Smith, Raleigh, NC (US); Pamela Wells, Hixson, TN (US); Laura A. Hassey, Raleigh, NC (US); Kiana M. Dezelon, Batesville, IN (US); Thomas A. Myers, Syracuse, NY (US); Andrew S. Robinson, Durham, NC (US); Varad N. Srivastava, Skaneateles, NY (US); Douglas A. Seim, Okeana, OH (US); Kenzi L. Mudge, Raleigh, NC (US); Jennifer A. Gunn, Durham, NC (US); John S. Schroder, Apex, NC (US); Brandon Smith, Cary, NC (US); Tanya M. Hawthorne, Raleigh, NC (US); Elizabeth A. Kowal, Cary, NC (US)

(73) Assignee: Hill-Rom Services, Inc., Batesville, IN (US)

(*) Notice: Subject to any disclaimer, the term of this patent is extended or adjusted under 35 U.S.C. 154(b) by 361 days.

(21) Appl. No.: 16/944,926

(22) Filed: Jul. 31, 2020

(65) Prior Publication Data

US 2021/0065885 A1    Mar. 4, 2021

Related U.S. Application Data

(60) Provisional application No. 62/894,125, filed on Aug. 30, 2019.

(51) Int. Cl.
*G16H 40/20* (2018.01)
*G16H 40/67* (2018.01)
(Continued)

(52) U.S. Cl.
CPC .......... *G16H 40/20* (2018.01); *A61G 7/0527* (2016.11); *G06K 7/10306* (2013.01);
(Continued)

(58) Field of Classification Search
CPC ...... G16H 40/20; G16H 40/67; H04B 17/318; A61G 7/0527; A61G 2205/60; H04W 4/029; G06K 7/10306
See application file for complete search history.

(56) References Cited

U.S. PATENT DOCUMENTS

| 5,182,823 A | 2/1993 | Alsip |
| 5,760,704 A | 6/1998 | Barton et al. |

(Continued)

FOREIGN PATENT DOCUMENTS

| JP | 2013-134544 | 7/2013 |
| WO | WO 97/25682 | 7/1997 |

(Continued)

OTHER PUBLICATIONS

Jonathan Strickland, How Near Field Communications Works, How Stuff Works (Nov. 12, 2012) (Year: 2012).*

(Continued)

*Primary Examiner* — Evangeline Barr
*Assistant Examiner* — Jordan L Jackson
(74) *Attorney, Agent, or Firm* — Barnes & Thornburg LLP

(57) ABSTRACT

High-accuracy locating systems and methods are used for determining successful caregiver rounding, monitoring whether housekeepers have properly cleaned patient beds, or determining whether patients have ambulated sufficient dis-
(Continued)

tances during recovery. Patient beds having at least two locating tags are used for establishing patient care zones around the patient beds. Locating anchors and equipment tags are moved around a patient room to determine optimum locating anchor placement within the patient room based on signal quality values. A locating tag on a patient bed switches roles to operate as a locating anchor in response to the patient bed becoming stationary. A locating tag has a digital compass which is used to determine a field of good ranging relative to a front of a caregiver wearing the locating tag.

31 Claims, 10 Drawing Sheets

(51) Int. Cl.
  *A61G 7/05*     (2006.01)
  *H04B 17/318*   (2015.01)
  *H04W 4/029*    (2018.01)
  *G06K 7/10*     (2006.01)

(52) U.S. Cl.
  CPC ........... *G16H 40/67* (2018.01); *H04B 17/318* (2015.01); *H04W 4/029* (2018.02); *A61G 2205/60* (2013.01)

(56) References Cited

U.S. PATENT DOCUMENTS

| | | |
|---|---|---|
| 5,790,114 A | 8/1998 | Geaghan et al. |
| 5,838,223 A | 11/1998 | Gallant et al. |
| 6,130,860 A | 10/2000 | Suzuki |
| 6,145,253 A | 11/2000 | Gallant et al. |
| 6,288,978 B1 | 9/2001 | Suzuki |
| 6,911,916 B1 | 6/2005 | Wang et al. |
| 6,957,187 B1 | 10/2005 | Kameda |
| 7,263,669 B2 | 8/2007 | Denholm |
| 7,319,386 B2 | 1/2008 | Collins, Jr. et al. |
| 7,344,079 B2 | 3/2008 | Steusloff et al. |
| 7,364,067 B2 | 4/2008 | Steusloff et al. |
| 7,450,024 B2 | 11/2008 | Wildman et al. |
| 7,475,019 B2 | 1/2009 | Rosenfeld et al. |
| 7,522,477 B1 | 4/2009 | Sheldon |
| 7,538,659 B2 | 5/2009 | Ulrich et al. |
| 7,562,026 B2 | 7/2009 | DelMonego et al. |
| 7,567,238 B2 | 7/2009 | Sugimoto et al. |
| 7,587,329 B2 | 9/2009 | Thompson et al. |
| 7,607,571 B2 | 10/2009 | Steusloff et al. |
| 7,676,386 B2 | 3/2010 | Stephenson |
| 7,746,218 B2 | 6/2010 | Collins, Jr. et al. |
| 7,831,679 B2 | 11/2010 | Apacible et al. |
| 7,904,312 B2 | 3/2011 | Denholm |
| 7,916,014 B2 | 3/2011 | Rapaport et al. |
| 7,987,110 B2 | 7/2011 | Cases et al. |
| 8,027,849 B2 | 9/2011 | Johnson et al. |
| 8,068,051 B1 | 11/2011 | Osterweil |
| 8,077,552 B1 | 12/2011 | Pope et al. |
| 8,094,521 B2 | 1/2012 | Levy |
| 8,115,641 B1 | 2/2012 | Dempsey |
| 8,169,304 B2 | 5/2012 | Schuman, Sr. et al. |
| 8,224,683 B2 | 7/2012 | Manos |
| 8,240,550 B2 | 8/2012 | Steusloff et al. |
| 8,384,526 B2 | 2/2013 | Schuman, Sr. et al. |
| 8,598,995 B2 | 12/2013 | Schuman et al. |
| 8,773,269 B2 | 7/2014 | Richardson et al. |
| 8,779,924 B2 | 7/2014 | Pesot et al. |
| 9,058,635 B1 | 6/2015 | Rybkin |
| 9,098,993 B2 | 8/2015 | Reed, Jr. |
| 9,240,120 B2 | 1/2016 | Girardeau et al. |
| 9,465,916 B2 | 10/2016 | Girardeau et al. |
| 9,659,148 B2 | 5/2017 | Girardeau et al. |
| 9,959,733 B2 | 5/2018 | Gu et al. |
| 9,971,869 B2 | 5/2018 | Girardeau et al. |
| 9,984,211 B2 | 5/2018 | Hsu |
| 10,226,177 B2 | 3/2019 | Chamberlain |
| 10,257,277 B2 | 4/2019 | Schlapfer et al. |
| 10,332,625 B2 | 6/2019 | Ting et al. |
| 10,629,049 B2 | 4/2020 | Hassey et al. |
| 2004/0128163 A1 | 7/2004 | Goodman et al. |
| 2006/0049936 A1 | 3/2006 | Collins et al. |
| 2006/0053035 A1 | 3/2006 | Eisenberg |
| 2006/0149589 A1 | 7/2006 | Wager |
| 2006/0173725 A1 | 8/2006 | Abraham et al. |
| 2006/0247948 A1 | 11/2006 | Ellis et al. |
| 2006/0267753 A1 | 11/2006 | Hussey et al. |
| 2006/0277070 A1 | 12/2006 | Hungerford et al. |
| 2007/0094046 A1 | 4/2007 | Cobbs et al. |
| 2007/0112610 A1 | 5/2007 | Johnson et al. |
| 2007/0122783 A1 | 5/2007 | Habashi |
| 2007/0210917 A1 | 9/2007 | Collins, Jr. et al. |
| 2007/0216660 A1 | 9/2007 | Sposato et al. |
| 2008/0082363 A1 | 4/2008 | Habashi |
| 2008/0106374 A1 | 5/2008 | Sharbaugh |
| 2008/0164998 A1 | 7/2008 | Scherpbier |
| 2008/0281637 A1 | 11/2008 | Matz |
| 2009/0021486 A1 | 1/2009 | Chaudhri et al. |
| 2009/0043634 A1 | 2/2009 | Tisdale |
| 2009/0089092 A1 | 4/2009 | Johnson et al. |
| 2009/0089093 A1 | 4/2009 | Johnson et al. |
| 2009/0094529 A1 | 4/2009 | Gonzalez et al. |
| 2009/0112618 A1 | 4/2009 | Johnson et al. |
| 2009/0119126 A1 | 5/2009 | Johnson et al. |
| 2009/0125332 A1 | 5/2009 | Martin |
| 2009/0125335 A1 | 5/2009 | Manetta et al. |
| 2009/0125840 A1 | 5/2009 | Squilla et al. |
| 2009/0178004 A1 | 7/2009 | Stoval, III et al. |
| 2009/0182577 A1 | 7/2009 | Squilla et al. |
| 2009/0212925 A1 | 8/2009 | Schuman, Sr. et al. |
| 2009/0212956 A1 | 8/2009 | Schuman et al. |
| 2009/0217080 A1 | 8/2009 | Ferguson et al. |
| 2009/0254365 A1 | 10/2009 | Gravina |
| 2009/0322548 A1 | 12/2009 | Gottlieb |
| 2010/0070294 A1 | 3/2010 | Horne et al. |
| 2010/0079276 A1 | 4/2010 | Collins, Jr. et al. |
| 2010/0191824 A1 | 7/2010 | Lindsay |
| 2010/0198622 A1 | 8/2010 | Gajic et al. |
| 2010/0305972 A1 | 12/2010 | McLaren et al. |
| 2010/0332509 A1 | 12/2010 | Rogers et al. |
| 2011/0010200 A1 | 1/2011 | Firozvi et al. |
| 2011/0153352 A1 | 6/2011 | Semian |
| 2011/0205062 A1 | 8/2011 | Pesot et al. |
| 2011/0208541 A1 | 8/2011 | Wilson et al. |
| 2011/0276343 A1 | 11/2011 | Lagor et al. |
| 2012/0010901 A1 | 1/2012 | Johnson et al. |
| 2012/0029932 A1 | 2/2012 | Stein et al. |
| 2012/0078661 A1 | 3/2012 | Sheldon et al. |
| 2012/0089419 A1 | 4/2012 | Huster |
| 2012/0253836 A1 | 10/2012 | Noble et al. |
| 2012/0310664 A1 | 12/2012 | Long et al. |
| 2013/0127620 A1* | 5/2013 | Siebers ................ A61B 5/1113 340/573.1 |
| 2013/0141233 A1* | 6/2013 | Jacobs ................ G16H 20/40 340/521 |
| 2014/0145848 A1 | 5/2014 | Amir |
| 2014/0266642 A1 | 9/2014 | Girardeau et al. |
| 2014/0266733 A1* | 9/2014 | Hayes ..................... A61G 7/05 600/484 |
| 2015/0156637 A1* | 6/2015 | Li ....................... H04W 56/002 455/454 |
| 2015/0269824 A1 | 9/2015 | Zhang |
| 2016/0034731 A1 | 2/2016 | Lin |
| 2016/0110509 A1 | 4/2016 | Girardeau et al. |
| 2017/0004264 A1* | 1/2017 | Girardeau ............... G16Z 99/00 |
| 2017/0035370 A1 | 2/2017 | Collins, Jr. et al. |
| 2017/0262593 A1 | 9/2017 | Girardeau et al. |
| 2017/0364644 A1* | 12/2017 | Johnson ............... G16H 40/67 |
| 2018/0075725 A1 | 3/2018 | Geng et al. |
| 2018/0174420 A1 | 6/2018 | Clark et al. |
| 2018/0322760 A1* | 11/2018 | Ribble ................. G16H 40/67 |
| 2019/0108908 A1 | 4/2019 | Faulks et al. |
| 2019/0122762 A1* | 4/2019 | Al-Ali ................. G16H 40/20 |

(56) References Cited

U.S. PATENT DOCUMENTS

| | | | |
|---|---|---|---|
| 2019/0228632 A1 | 7/2019 | Hassey et al. | |
| 2020/0090804 A1 | 3/2020 | Robinson et al. | |
| 2020/0203010 A1* | 6/2020 | Durlach | A61G 7/00 |

FOREIGN PATENT DOCUMENTS

| | | |
|---|---|---|
| WO | WO 98/14888 | 4/1998 |
| WO | WO 2008/030249 | 3/2008 |
| WO | WO 2008/061833 | 5/2008 |
| WO | WO 2010/052624 | 5/2010 |
| WO | WO 2010/091073 | 8/2010 |
| WO | WO 2017/083353 | 5/2017 |

OTHER PUBLICATIONS

Chung et al., Signaling and multiple access techniques for ultra-wideband 4G wireless communication systems, 12(2) IEEE Wireless Communications 46-55 (Apr. 18, 2005) (Year: 2005).*

"The WISER way to track, find & secure the things that matter" from WISER Systems; https://www.wisersystems.com/productsbuy/; dated Jan. 24, 2018; 5 pages.

"PLUS Synchronization Distribution Panel" brochure from Time Domain; Time Domain Product Sheets; 2 pages; printed Jan. 24, 2018.

"Precise Location Ultra Wideband System" brochure from Time Domain; Time Domain Product Sheets; 2 pages; printed Jan. 24, 2018.

"Dart UWB Technology" product datasheet from Zebra Technologies; 2 pages; printed Jan. 24, 2018.

"DartTag Portfolio" product datasheet from Zebra Technologies; 2 pages; printed Jan. 24, 2018.

"Dart UWB Hub & Sensors" product datasheet from Zebra Technologies; 2 pages; printed Jan. 24, 2018.

DecaWave "DWM1000 IEEE 802.15.4-2011 UWB Transceiver Module" datasheet; © Decawave Ltd 2016; Version 1.6; 29 pages.

* cited by examiner

ULTRA-WIDEBAND LOCATING SYSTEMS AND METHODS

The present disclosure claims the benefit, under 35 U.S.C. 119(e), of U.S. Provisional Application No. 62/894,125, filed Aug. 30, 2019, which is hereby incorporated by reference herein in its entirety.

BACKGROUND

The present disclosure relates to locating systems used to monitor the whereabouts of people and equipment in a facility and particularly, to ultra-wideband (UWB) locating systems and methods. More particularly, the present disclosure relates to high-accuracy locating systems used in healthcare facilities.

Locating systems are used in various facilities to determine the whereabouts of people and equipment. Such locating systems are used widely in healthcare facilities, for example, to determine the locations of caregivers and medical equipment. A variety of wireless technologies such as infrared (IR), radio frequency (RF), ultrasound, and so forth have been used for communication between portable locating tags and fixed-in-place receivers or transceivers. In recent times, ultra-wideband (UWB) locating systems have been developed and are able to determine the locations of locating tags much more accurately than the predecessor systems. See International Publication No. WO 2017/083353 A1 for a discussion of a UWB locating system, for example. UWB chipsets are becoming more affordable allowing for UWB locating systems to be used more widely. For example, Decawave, Ltd. of Dublin, Ireland makes UWB chipsets such as the DWM100 IC and those found in the DWM1000 Module and the DWM1001 Module.

While UWB locating systems are known in general, the industry has not yet fully realized the potential for more sophisticated algorithms in connection with such locating systems. Accordingly, a need persists for improvements in high-accuracy locating systems, such as UWB locating systems, particularly those used in healthcare facilities. Locating systems that improve caregiver workflow and reduce medical device alarm fatigue would be welcomed in the healthcare industry.

SUMMARY

An apparatus, system, or method may comprise one or more of the features recited in the appended claims and/or the following features which, alone or in any combination, may comprise patentable subject matter:

According to a first aspect of the present disclosure, a caregiver rounding system may include a bed that may be configured to support a patient thereon, an equipment locating tag that may be coupled to the bed, and a caregiver locating tag that may be coupled to a caregiver. The caregiver rounding system of the first aspect may also include a plurality of receivers that may be mounted at fixed locations and that may be in wireless communication with the equipment locating tag and the caregiver locating tag, and at least one computer that may be communicatively coupled to the plurality of receivers. The equipment locating tag, the caregiver locating tag, the plurality of receivers, and the at least one computer may cooperate to form a high-accuracy locating system that may be operable to determine a location of the equipment locating tag and the caregiver locating tag within at least one foot of an actual location of the equipment locating tag and the caregiver locating tag, respectively. The at least one computer of the first aspect may model a rounding zone adjacent the bed based on the location of the equipment locating tag. The at least one computer may determine that the caregiver has successfully completed a caregiver round if the caregiver locating tag is located within the rounding zone for a threshold period of time.

In some embodiments of the first aspect, the rounding zone may be defined as being within a boundary that is about three feet from a periphery of the bed. Alternatively or additionally, the rounding zone may be defined as being within a boundary calculated as being about three feet away from a footprint of the bed as theoretically projected onto a floor supporting the bed. If desired, the rounding zone may be defined as being a circular boundary having a radius of about five feet and centered on the equipment locating tag. Optionally, the threshold period of time of the first aspect is about five minutes. Alternatively, the threshold period of time of the first aspect may be greater than about one minute.

Optionally, the equipment locating tag and the caregiver locating tag of the first aspect may communicate with the plurality of receivers via ultra-wideband (UWB) signals. If desired, the locations of the equipment locating tag and the caregiver locating tag may be determined by the at least one computer using two way ranging and time difference of arrival (TDOA) techniques. Alternatively or additionally, the locations of the equipment locating tag and the caregiver locating tag of the first aspect may be determined by the at least one computer using time of arrival (TOA) at which transmissions from the equipment locating tag and the caregiver locating tag are received at the plurality of receivers. Further alternatively or additionally, the at least one computer may use signals from only a subset of the plurality of receivers to determine the location of the equipment locating tag and the caregiver locating tag. The subset may be determined based on signal strength of signals from the equipment locating tag and the caregiver locating tag to the plurality of receivers, for example. In some instances, the subset may include at least three receivers from the plurality of receivers that may have highest signal strength values as compared to others of the plurality of receivers.

In some embodiments of the first aspect, the bed may include a sensor that may sense a presence of a patient on the bed and the at least one computer may be configured to determine that a successful caregiver round has occurred only if the patient is present on the bed as sensed by the sensor. If desired, the bed may include communication circuitry that may be configured to transmit patient presence data for receipt by the at least one computer. The sensor may include a weight sensor of a weigh scale system of the bed, for example. In some embodiments, the caregiver rounding system of the first aspect may further include a patient locating tag that may be coupled to a patient. The at least one computer may be configured to determine that a successful caregiver round has occurred only if the patient locating tag is determined to be within the rounding zone with the caregiver locating tag for the threshold period of time.

According to a second aspect of the present disclosure, a caregiver rounding system may include a patient locating tag that may be coupled to a patient, a caregiver locating tag that may be coupled to a caregiver, and a plurality of receivers that may be mounted at fixed locations and in wireless communication with the patient locating tag and the caregiver locating tag. The caregiver rounding system of the second aspect may also include at least one computer that may be communicatively coupled to the plurality of receivers. The patient locating tag, the caregiver locating tag, the plurality of receivers, and the at least one computer may cooperate to form a high-accuracy locating system that may be operable to determine a location of the patient locating tag and the caregiver locating tag within at least one foot of an actual location of the patient locating tag and the caregiver locating tag, respectively. The at least one computer of the second aspect may model a rounding zone that may be adjacent the patient based on the location of the patient locating tag. The at least one computer may determine that the caregiver has successfully completed a caregiver round if the caregiver locating tag is located within the rounding zone for a threshold period of time.

In some embodiments of the second aspect, the rounding zone may be defined as being within a boundary that is about three feet from the patient locating tag. Optionally, a boundary of the rounding zone may be defined as a circle on a floor with the patient locating tag being situated vertically above a center of the circle. For example, a radius of the circle may be about three feet in length. If desired, the threshold period of time may be about five minutes. Alternatively, the threshold period of time may be greater than about one minute. If desired, the at least one computer of the second aspect may be configured to determine that a successful caregiver round has occurred only if the patient locating tag and the caregiver locating tag are both determined to be within a patient room assigned to the patient.

Optionally, the patient locating tag and the caregiver locating tag of the second aspect may communicate with the plurality of receivers via ultra-wideband (UWB) signals. If desired, the locations of the patient locating tag and the caregiver locating tag may be determined by the at least one computer using two way ranging and time difference of arrival (TDOA) techniques. Alternatively, the locations of the patient locating tag and the caregiver locating tag may be determined by the at least one computer using time of arrival (TOA) at which transmissions from the patient locating tag and the caregiver locating tag are received at the plurality of receivers. Further alternatively or additionally, the at least one computer may use signals from only a subset of the plurality of receivers to determine the location of the patient locating tag and the caregiver locating tag. The subset may be determined based on signal strength of signals from the patient locating tag and the caregiver locating tag to the plurality of receivers, for example. In some instances, the subset may include at least three receivers from the plurality of receivers that may have highest signal strength values as compared to others of the plurality of receivers.

According to a third aspect of the present disclosure, a caregiver rounding method may include providing a bed that may be configured to support a patient thereon, coupling an equipment locating tag to the bed, providing a caregiver locating tag to be transported by a caregiver, and providing a plurality of receivers that may be mounted at fixed locations and that may be in wireless communication with the equipment locating tag and the caregiver locating tag. The method of the third aspect may also include communicatively coupling at least one computer to the plurality of receivers. The equipment locating tag, the caregiver locating tag, the plurality of receivers, and the at least one computer of the third aspect may cooperate to form a high-accuracy locating system that may be operable to determine a location of the equipment locating tag and the caregiver locating tag within at least one foot of an actual location of the equipment locating tag and the caregiver locating tag, respectively. The method of the third aspect may further include, with the at least one computer, modeling a rounding zone that may be adjacent the bed based on the location of the equipment locating tag, and with the at least one computer, determining that the caregiver has successfully completed a caregiver round if the caregiver locating tag is located within the rounding zone for a threshold period of time.

In some embodiments of the third aspect, modeling the rounding zone may include modeling the rounding zone as being within a boundary that may be about three feet from a periphery of the bed. Alternatively, modeling the rounding zone may include modeling the rounding zone as being within a boundary calculated as being about three feet away from a footprint of the bed as theoretically projected onto a floor supporting the bed. Further alternatively, modeling the rounding zone may include modeling the rounding zone as being a circular boundary having a radius of about five feet and centered on the equipment locating tag. Optionally, the threshold period of time of the third aspect may be about five minutes. Further optionally, the threshold period of time of the third aspect may be greater than about one minute.

If desired, the equipment locating tag and the caregiver locating tag of the third aspect may communicate with the plurality of receivers via ultra-wideband (UWB) signals. The caregiver rounding method of the third aspect may further include, with the at least one computer, determining the locations of the equipment locating tag and the caregiver locating tag using two way ranging and time difference of arrival (TDOA) techniques. Alternatively or additionally, the caregiver rounding method of the third aspect may further include, with the at least one computer, determining the locations of the equipment locating tag and the caregiver locating tag using time of arrival (TOA) at which transmissions from the equipment locating tag and the caregiver locating tag are received at the plurality of receivers.

In some embodiments of the third aspect, the caregiver rounding method further includes, with the at least one computer, using signals from only a subset of the plurality of receivers to determine the location of the equipment locating tag and the caregiver locating tag. The subset may be determined based on signal strength of signals from the equipment locating tag and the caregiver locating tag to the plurality of receivers of the third aspect. The subset may include at least three receivers from the plurality of receivers having highest signal strength values as compared to others of the plurality of receivers, for example.

Optionally, the caregiver rounding method of the third aspect may further include sensing a presence of a patient on the bed using at least one sensor. The at least one computer may be configured to determine that a successful caregiver round has occurred only if the patient is present on the bed as sensed by the sensor. Further optionally, the caregiver rounding method of the third aspect may further include transmitting patient presence data for receipt by the at least one computer using communication circuitry of the bed. If desired, the sensor may include a weight sensor of a weigh scale system of the bed. In some embodiments, the caregiver rounding method of the third aspect may further include providing a patient locating tag to be transported by a patient and determining with the at least one computer that a successful caregiver round has occurred only if the patient locating tag is determined to be within the rounding zone with the caregiver locating tag for the threshold period of time.

According to a fourth aspect of the present disclosure, a caregiver rounding method may include providing a patient locating tag to be transported by a patient, providing a caregiver locating tag to be transported by a caregiver, and providing a plurality of receivers that may be mounted at fixed locations and that may be in wireless communication with the patient locating tag and the caregiver locating tag. The method of the fourth aspect may also include communicatively coupling at least one computer to the plurality of receivers. The patient locating tag, the caregiver locating tag, the plurality of receivers, and the at least one computer of the fourth aspect may cooperate to form a high-accuracy locating system operable to determine a location of the patient locating tag and the caregiver locating tag within at least one foot of an actual location of the patient locating tag and the caregiver locating tag, respectively. The method of the fourth aspect may further include, with the at least one computer, modeling a rounding zone that may be adjacent the patient based on the location of the patient locating tag, and with the at least one computer, determining that the caregiver has successfully completed a caregiver round if the caregiver locating tag is located within the rounding zone for a threshold period of time.

In some embodiments of the fourth aspect, modeling the rounding zone may include modeling the rounding zone as being within a boundary that may be about three feet from the patient locating tag. Alternatively, modeling the rounding zone may include modeling the rounding zone as being within a boundary that may be defined as a circle on a floor with the patient locating tag being situated vertically above a center of the circle. If desired, a radius of the circle is about three feet in length. Optionally, the threshold period of time of the fourth aspect may be about five minutes. Further optionally, the threshold period of time of the fourth aspect may be greater than about one minute.

If desired, the patient locating tag and the caregiver locating tag of the fourth aspect may communicate with the plurality of receivers via ultra-wideband (UWB) signals. The caregiver rounding method of the fourth aspect may further include, with the at least one computer, determining the locations of the patient locating tag and the caregiver locating tag using two way ranging and time difference of arrival (TDOA) techniques. Alternatively or additionally, the caregiver rounding method of the fourth aspect may further include, with the at least one computer, determining the locations of the patient locating tag and the caregiver locating tag using time of arrival (TOA) at which transmissions from the patient locating tag and the caregiver locating tag are received at the plurality of receivers.

In some embodiments of the fourth aspect, the caregiver rounding method may further include, with the at least one computer, using signals from only a subset of the plurality of receivers to determine the location of the patient locating tag and the caregiver locating tag. The subset may be determined based on signal strength of signals from the patient locating tag and the caregiver locating tag to the plurality of receivers of the fourth aspect. The subset may include at least three receivers from the plurality of receivers having highest signal strength values as compared to others of the plurality of receivers, for example. Optionally, the caregiver rounding system of the fourth aspect may further include, with the at least one computer, determining that a successful caregiver round has occurred only if the patient locating tag and the caregiver locating tag are both determined to be within a patient room assigned to the patient.

According to a fifth aspect of the present disclosure, a system for monitoring proper cleaning of a patient bed by a housekeeper may include a housekeeper locating tag that may be transported by the housekeeper, a plurality of receivers that may be mounted at fixed locations and that may be in wireless communication with the housekeeper locating tag, and at least one computer that may be communicatively coupled to the plurality of receivers. The housekeeper locating tag, the plurality of receivers, and the at least one computer of the fifth aspect may cooperate to form a high-accuracy locating system that may be operable to determine a location of the housekeeper locating tag within at least one foot of an actual location of the housekeeper locating tag. The at least one computer may model a patient bed position of a patient bed in a patient room. The at least one computer may determine that the housekeeper has properly cleaned the patient bed if the housekeeper locating tag is determined to have substantially circumnavigated the patient bed position.

In some embodiments of the fifth aspect, the at least one computer may model the patient bed position as being a set of coordinates at which a patient bed is expected to occupy in the patient room. Optionally, the system of the fifth aspect may further include an equipment locating tag that may be coupled to the patient bed and that may be in communication with the plurality of receivers. In such situations, the at least one computer may model the patient bed position as being within a boundary around the equipment locating tag. For example, the boundary may be defined as a circle having a radius of about two feet. Alternatively, the boundary may be defined as a rectangle having dimensions commensurate in size with a periphery of the hospital bed.

Optionally, the system of the fifth aspect may further include an equipment locating tag that may be coupled to the patient bed and that may be in communication with the plurality of receivers. If desired, the at least one computer may model the patient bed position as being a location of the equipment locating tag and the at least one computer may determine that the housekeeper has properly cleaned the bed if the housekeeper locating tag is determined to have substantially circumnavigated the equipment locating tag. It is contemplated by this disclosure that the housekeeper locating tag may be considered to have substantially circumnavigated the equipment locating tag if the housekeeper locating tag has traveled at least 270 degrees around the equipment locating tag. It is also contemplated by this disclosure that the housekeeper locating tag may be considered to have substantially circumnavigated the patient bed position if the housekeeper locating tag has traveled at least 270 degrees around the patient bed position as modeled in the at least one computer.

In some embodiments of the fifth aspect, the patient bed and a model of the patient bed position may include a head end, a foot end, a first side and a second side. In such embodiments, the housekeeper locating tag may be considered to have substantially circumnavigated the patient bed position if the housekeeper locating tag has been determined by the at least one computer to have been next to each of the head end, foot end, first side, and second side. Optionally, the at least one computer may track an amount of time that the housekeeper locating tag spends circumnavigating the patient bed position and the at least one computer may determine that the housekeeper has properly cleaned the patient bed only if the housekeeper locating tag is determined to have spent more than a minimum amount of time circumnavigating the patient bed position. Further optionally, the at least one computer may initiate a notification to a supervisor if the housekeeper is determined by the at least one computer not to have properly cleaned the patient bed.

If desired, the housekeeper locating tag of the fifth aspect may communicate with the plurality of receivers via ultra-wideband (UWB) signals. The location of the housekeeper locating tag may be determined by the at least one computer of the fifth aspect using two way ranging and time difference of arrival (TDOA) techniques. Alternatively or additionally, the location of the housekeeper locating tag may be determined by the at least one computer using time of arrival (TOA) at which transmissions from the housekeeper locating tag are received at the plurality of receivers.

In some embodiments of the fifth aspect, the at least one computer may use signals from only a subset of the plurality of receivers to determine the location of the housekeeper locating tag. The subset may be determined based on signal strength of signals from the housekeeper locating tag to the plurality of receivers of the fifth aspect. The subset may include at least three receivers from the plurality of receivers having highest signal strength values as compared to others of the plurality of receivers of the fifth aspect, for example.

Optionally, the at least one computer of the fifth aspect may determine that the housekeeper has properly cleaned the patient bed only if the housekeeper locating tag is determined to have remained in proximity of the patient bed position within a threshold distance while circumnavigating the patient bed position. For example, the threshold distance may be about three feet in some embodiments of the fifth aspect.

According to a sixth aspect of the present disclosure, a method for monitoring proper cleaning of a patient bed by a housekeeper may include providing a housekeeper locating tag to be transported by the housekeeper, providing a plurality of receivers that may be mounted at fixed locations and that may be in wireless communication with the housekeeper locating tag, and communicatively coupling at least one computer to the plurality of receivers. The housekeeper locating tag, the plurality of receivers, and the at least one computer of the sixth aspect may cooperate to form a high-accuracy locating system that may be operable to determine a location of the housekeeper locating tag within at least one foot of an actual location of the housekeeper locating tag. The method of the sixth aspect may also include, with the at least one computer, modeling a patient bed position of a patient bed in a patient room, and with the at least one computer, determining that the housekeeper has properly cleaned the patient bed if the housekeeper locating tag is determined to have substantially circumnavigated the patient bed position.

In some embodiments of the sixth aspect, modeling the patient bed position with the at least one computer may include modeling the patient bed position as being a set of coordinates at which a patient bed is expected to occupy in the patient room. Optionally, the method of the sixth aspect may further include providing an equipment locating tag that may be coupled to the patient bed and that may be in communication with the plurality of receivers. If desired, modeling the patient bed position with the at least one computer may include modeling the patient bed position as being within a boundary around the equipment locating tag. For example, the boundary may be defined as a circle having a radius of about two feet. Alternatively, the boundary may be defined as a rectangle having dimensions commensurate in size with a periphery of the hospital bed.

Optionally, the method of the sixth aspect may further include providing an equipment locating tag that may be coupled to the patient bed and that may be in communication with the plurality of receivers. Further optionally, modeling the patient bed position with the at least one computer may include modeling the patient bed position as being a location of the equipment locating tag. In such instances, the at least one computer may determine that the housekeeper has properly cleaned the bed if the housekeeper locating tag is determined to have substantially circumnavigated the equipment locating tag.

In some embodiments of the sixth aspect, the housekeeper locating tag may be considered to have substantially circumnavigated the equipment locating tag if the housekeeper locating tag has traveled at least 270 degrees around the equipment locating tag. Alternatively, the housekeeper locating tag may be considered to have substantially circumnavigated the patient bed position if the housekeeper locating tag has traveled at least 270 degrees around the patient bed position as modeled in the at least one computer. If desired, the patient bed and a model of the patient bed position may include a head end, a foot end, a first side and a second side. The housekeeper locating tag may be considered to have substantially circumnavigated the patient bed position if the housekeeper locating tag has been determined by the at least one computer of the sixth aspect to have been next to each of the head end, foot end, first side, and second side.

Optionally, the method of the sixth aspect may further include, with the at least one computer, tracking an amount of time that the housekeeper locating tag spends circumnavigating the patient bed position. Further optionally, the at least one computer may determine that the housekeeper has properly cleaned the patient bed only if the housekeeper locating tag is determined to have spent more than a minimum amount of time circumnavigating the patient bed position. If desired, the method of the sixth aspect may further include, with the at least one computer, initiating a notification to a supervisor if the housekeeper is determined by the at least one computer not to have properly cleaned the patient bed.

In some embodiments, the housekeeper locating tag may communicate with the plurality of receivers via ultra-wide-band (UWB) signals. The method of the sixth aspect may further include, with the at least one computer, determining the location of the housekeeper locating tag using two way ranging and time difference of arrival (TDOA) techniques. Alternatively or additionally, the method of the sixth aspect may further include, with the at least one computer, determining the location of the housekeeper locating tag using time of arrival (TOA) at which transmissions from the housekeeper locating tag are received at the plurality of receivers.

Optionally, the method of the sixth aspect may further include, with the at least one computer, using signals from only a subset of the plurality of receivers to determine the location of the housekeeper locating tag. For example, the subset may be determined based on signal strength of signals from the housekeeper locating tag to the plurality of receivers of the sixth aspect. If desired, the subset of the sixth aspect may include at least three receivers from the plurality of receivers having highest signal strength values as compared to others of the plurality of receivers.

In some embodiments of the sixth aspect, the at least one computer may determine that the housekeeper has properly cleaned the patient bed only if the housekeeper locating tag is determined to have remained in proximity of the patient bed position within a threshold distance while circumnavigating the patient bed position. For example, wherein the threshold distance may be about three feet according to the sixth aspect.

According to a seventh aspect of the present disclosure, a system for determining how far a patient has ambulated within a healthcare facility may include a patient locating tag that may be coupled to a patient, a plurality of receivers that may be mounted at fixed locations and that may be in wireless communication with the patient locating tag, and at least one computer that may be communicatively coupled to the plurality of receivers. The patient locating tag, the plurality of receivers, and the at least one computer of the seventh aspect may cooperate to form a high-accuracy locating system operable to determine a location of the patient locating tag within at least one foot of an actual location of the patient locating tag. The at least one computer of the seventh aspect may calculate a total distance that the patient has ambulated based on movement of the patient locating tag within the healthcare facility over a threshold period of time.

In some embodiments, the system of the seventh aspect may further include a plurality of equipment locating tags that may be attached to mobile patient support apparatuses. In such embodiments, the at least one computer may omit from the total distance any movement of the patient locating tag that may be accompanied by a substantially concurrent movement of at least one of the plurality of equipment locating tags that may be within a threshold distance of the patient locating tag based on an assumption that the patient is possibly being transported on the respective patient support apparatus rather than ambulating.

Optionally, the threshold distance of the seventh aspect may be about five feet or less. The total distance may include movement of the patient locating tag within a patient room assigned to the patient and movement of the patient locating tag outside the patient room. For example, movement of the patient locating tag within the patient room may include movement of the patient locating tag between a patient bed in the patient room and a bathroom included in the patient room. Still further, movement of the patient locating tag outside the patient room may include movement of the patient locating tag in a hallway adjacent to the patient room.

If desired, the threshold period of time of the seventh aspect may be about four hours or more. Alternatively or additionally, the threshold period of time may correspond to a shift during which caregivers of the healthcare facility work. Further alternatively or additionally, the threshold period of time may be less than four hours.

In some embodiments, the at least one computer of the seventh aspect may record the total distance in memory after the threshold period of time has elapsed. Optionally, after the threshold period of time has elapsed, the at least one computer may transmit the total distance to an electronic medical records (EMR) computer for storage in the patient's electronic medical record. Further optionally, the at least one computer may compare the total distance to a predetermined distance after the threshold period of time has elapsed and may determine whether or not the total distance exceeds the predetermined distance. If desired, the at least one computer may report a result of the comparison to a caregiver. Alternatively or additionally, the at least one computer may report a result of the comparison to a nurse call server.

Optionally, the patient locating tag of the seventh aspect may communicate with the plurality of receivers via ultra-wideband (UWB) signals. Further optionally, the location of the patient locating tag may be determined by the at least one computer using two way ranging and time difference of arrival (TDOA) techniques. Alternatively or additionally the location of the patient locating tag of the seventh aspect may be determined by the at least one computer using time of arrival (TOA) at which transmissions from the patient locating tag are received at the plurality of receivers. It is contemplated that the at least one computer of the seventh aspect may use signals from only a subset of the plurality of receivers to determine the location of the patient locating tag and the subset may be determined based on signal strength of signals from the patient locating tag to the plurality of receivers. For example, the subset of the seventh aspect may include at least three receivers from the plurality of receivers having highest signal strength values as compared to others of the plurality of receivers.

According to an eighth aspect of the present disclosure, a method for determining how far a patient has ambulated within a healthcare facility may include providing a patient locating tag to be transported by a patient, providing a plurality of receivers that may be mounted at fixed locations and that may be in wireless communication with the patient locating tag, and communicatively coupling at least one computer to the plurality of receivers. The patient locating tag, the plurality of receivers, and the at least one computer of the eighth aspect may cooperate to form a high-accuracy locating system that may be operable to determine a location of the patient locating tag within at least one foot of an actual location of the patient locating tag. The method of the eighth aspect may further include calculating, with the at least one computer, a total distance that the patient has ambulated based on movement of the patient locating tag within the healthcare facility over a threshold period of time.

In some embodiments, the method of the eighth aspect may further include attaching a plurality of equipment locating tags to mobile patient support apparatuses. In such embodiments, the method may include omitting, with the at least one computer, from the total distance any movement of the patient locating tag that may be accompanied by a substantially concurrent movement of at least one of the plurality of equipment locating tags that may be within a threshold distance of the patient locating tag based on an assumption that the patient is possibly being transported on the respective patient support apparatus rather than ambulating.

Optionally, the threshold distance may be about five feet or less. The total distance may include movement of the patient locating tag of the eighth aspect within a patient room assigned to the patient and movement of the patient locating tag outside the patient room. For example, movement of the patient locating tag within the patient room may include movement of the patient locating tag between a patient bed in the patient room and a bathroom included in the patient room. Still further, movement of the patient locating tag outside the patient room includes movement of the patient locating tag in a hallway adjacent to the patient room.

If desired, the threshold period of time of the eighth aspect may be about four hours or more. Alternatively or additionally, the threshold period of time may correspond to a shift during which caregivers of the healthcare facility work. Further alternatively or additionally, the threshold period of time may be less than four hours.

In some embodiments, the method of the eighth aspect may further include recording in memory of the at least one computer the total distance after the threshold period of time has elapsed. Optionally, the method of the eighth aspect may further include, after the threshold period of time has elapsed, transmitting with the at least one computer the total distance to an electronic medical records (EMR) computer for storage in the patient's electronic medical record. Further optionally, the method of the eighth aspect may further include, with the at least one computer, comparing the total distance to a predetermined distance after the threshold period of time has elapsed and determining whether or not the total distance exceeds the predetermined distance. If desired, the method of the eighth aspect may further include, with the at least one computer, reporting a result of the comparison to a caregiver. Alternatively or additionally, the method of the eighth aspect may further include, with the at least one computer, reporting a result of the comparison to a nurse call server.

Optionally, the patient locating tag of the eighth aspect may communicate with the plurality of receivers via ultra-wideband (UWB) signals. Further optionally, the method of the eighth aspect may further include, with the at least one computer, determining the location of the patient locating tag using two way ranging and time difference of arrival (TDOA) techniques. Alternatively or additionally, the method of the eight aspect may further include, with the at least one computer, determining the location of the patient locating tag using time of arrival (TOA) at which transmissions from the patient locating tag are received at the plurality of receivers. Further optionally, the method of the eighth aspect may further include, with the at least one computer, using signals from only a subset of the plurality of receivers to determine the location of the patient locating tag and the subset may be determined based on signal strength of signals from the patient locating tag to the plurality of receivers. For example, the subset of the eight aspect may include at least three receivers from the plurality of receivers having highest signal strength values as compared to others of the plurality of receivers.

According to a ninth aspect of the present disclosure, a system for locating a caregiver in a patient room may include a patient bed that may include circuitry, a first transceiver that may be carried by the patient bed and that may be coupled to the circuitry, a second transceiver that may be carried by the patient bed and that may be coupled to the circuitry, and a caregiver locating tag that may be transported by a caregiver in the patient room. The caregiver locating tag of the ninth aspect may communicate a tag identification (ID) to the circuitry via the first and second transceivers. The circuitry of the ninth aspect may use one or more of two way ranging techniques, time difference of arrival (TDOA) techniques, or time of arrival (TOA) techniques to determine a location of the caregiver locating tag in the patient room.

In some embodiments of the ninth aspect, the first transceiver may be situated adjacent a head end of the patient bed and the second transceiver may be situated adjacent a foot end of the patient bed. If desired, the first and second transceivers may be situated along a longitudinal centerline of the patient bed. Optionally, the circuitry of the patient bed of the ninth aspect may model a caregiver control zone around the patient bed and if the circuitry determines that the caregiver locating tag is within the caregiver control zone, the bed circuitry may determine which functions of the patient bed the caregiver has permission to modify. For example, silencing bed alarms may be among the functions of the patient bed that the caregiver may have permission to modify when within the caregiver control zone. Alternatively or additionally, activating at least one therapy function may be among the functions of the patient bed that the caregiver may have permission to modify when within the caregiver control zone. Further alternatively or additionally, activating movement of one or more portions of a bed frame of the patient bed may be among the functions that the caregiver may have permission to modify when within the caregiver control zone.

Optionally, the system of the ninth aspect may further include a server remote from the patient bed. The remote server and bed circuitry may be in communication such that the remote server may communicate the functions of the patient bed that the caregiver has permission to modify in response to receipt of information from the bed circuitry regarding the tag ID that is located within the caregiver control zone.

If desired, the system of the ninth aspect may further include a third transceiver that may be mounted in the patient room and a hub computer that may be in communication with the third transceiver. The third transceiver may be in communication with the first and second transceivers carried by the patient bed. Optionally, the hub computer may determine a location and orientation of the patient bed in the patient room based on transmissions from the first and second transceivers to the third transceiver. Further optionally, the hub computer may use one or more of two way ranging techniques, time difference of arrival (TDOA) techniques, or time of arrival (TOA) techniques to determine the location and orientation of the patient bed in the patient room.

In some embodiments, the system of the ninth aspect further includes at least one server that may include at least one of a nurse call server, a real time locating system (RTLS) server, and an electronic medical records (EMR) server that may be in communication with the hub computer. The hub computer may communicate information pertaining to the location and orientation of the patient bed to the at least one server of the ninth aspect. If desired, the hub computer and circuitry of the patient bed may cooperate to determine a location of the caregiver in the patient room based on communications that may be received from the caregiver locating tag by the first, second, and third transceivers. Alternatively, the system of the ninth aspect may further include at least one server that may include at least one of a nurse call server, a real time locating system (RTLS) server, and an electronic medical records (EMR) server that may be in communication with the hub computer and the hub computer may communicate information pertaining to the location of the caregiver locating tag to the at least one server.

If desired, the third transceiver of the ninth aspect may communicate with the first and second transceivers using ultra-wideband (UWB) signals. It is also contemplated that the caregiver locating tag of the ninth aspect may communicate with the first, second, and third transceivers using ultra-wideband (UWB) signals. Still further, it is contemplated that the caregiver locating tag of the ninth aspect may communicate with the first and second transceivers using ultra-wideband (UWB) signals.

According to a tenth aspect of the present disclosure, a method for locating a caregiver in a patient room may include providing a patient bed that may have circuitry, a first transceiver that may be coupled to the circuitry, and a second transceiver that may be coupled to the circuitry. The method of the tenth aspect may also include providing a caregiver locating tag that may be transported by a caregiver in the patient room and communicating a tag identification (ID) from the caregiver locating tag to the circuitry via the first and second transceivers. The method of the tenth aspect may further include determining with the circuitry using one or more of two way ranging techniques, time difference of arrival (TDOA) techniques, or time of arrival (TOA) techniques a location of the caregiver locating tag in the patient room.

In some embodiments of the tenth aspect, providing the patient bed with the first transceiver and the second transceiver may include providing the patient bed with the first transceiver situated adjacent a head end of the patient bed and with the second transceiver situated adjacent a foot end of the patient bed. Alternatively or additionally, providing the patient bed with the first transceiver and the second transceiver may include providing the patient bed with the first and second transceivers situated along a longitudinal centerline of the patient bed.

The method of the tenth aspect may further include modeling with the circuitry a caregiver control zone around the patient bed and, if the circuitry determines that the caregiver locating tag may be within the caregiver control zone, determining with the bed circuitry which functions of the patient bed the caregiver has permission to modify. For example, silencing bed alarms may be among the functions of the patient bed that the caregiver may have permission to modify when within the caregiver control zone. Alternatively or additionally, activating at least one therapy function may be among the functions of the patient bed that the caregiver may have permission to modify when within the caregiver control zone. Further alternatively or additionally, activating movement of one or more portions of a bed frame of the patient bed may be among the functions that the caregiver may have permission to modify when within the caregiver control zone.

Optionally, the method of the tenth aspect further includes providing a server that may be remote from the patient bed and that may be in communication with the circuitry of the patient bed. The method of the tenth aspect may also include communicating from the remote server the functions of the patient bed that the caregiver may have permission to modify in response to receipt of information from the bed circuitry regarding the tag ID that may be located within the caregiver control zone.

If desired, the method of the tenth aspect may further include providing a third transceiver that may be mounted in the patient room and providing a hub computer that may be in communication with the third transceiver. Optionally, the third transceiver may be in communication with the first and second transceivers carried by the patient bed. Further optionally, the method of the tenth aspect may also include determining with the hub computer a location and orientation of the patient bed in the patient room based on transmissions from the first and second transceivers to the third transceiver. Still further optionally, the method of the tenth aspect may further include determining with the hub computer using one or more of two way ranging techniques, time difference of arrival (TDOA) techniques, or time of arrival (TOA) techniques, the location and orientation of the patient bed in the patient room.

In some embodiments, the method of the tenth aspect may further include providing at least one server comprising at least one of a nurse call server, a real time locating system (RTLS) server, and an electronic medical records (EMR) server that may be in communication with the hub computer. The method may also include communicating to the at least one server from the hub computer information pertaining to the location and orientation of the patient bed of the tenth aspect.

Optionally, the method of the tenth aspect may further include using cooperatively the hub computer and the circuitry of the patient bed to determine a location of the caregiver in the patient room based on communications received from the caregiver locating tag by the first, second, and third transceivers. If desired, the method of the tenth aspect may also include providing at least one server comprising at least one of a nurse call server, a real time locating system (RTLS) server, and an electronic medical records (EMR) server that may be in communication with the hub computer, and communicating to the at least one server from the hub computer information pertaining to the location of the caregiver locating tag.

If desired, the third transceiver of the tenth aspect may communicate with the first and second transceivers using ultra-wideband (UWB) signals. It is also contemplated that the caregiver locating tag of the tenth aspect may communicate with the first, second, and third transceivers using ultra-wideband (UWB) signals. Still further, it is contemplated that the caregiver locating tag of the tenth aspect may communicate with the first and second transceivers using ultra-wideband (UWB) signals.

According to an eleventh aspect of the present disclosure, a method for configuring a patient room for a locating system may include determining a boundary of an area of interest in the patient room. The area of interest may be smaller than a floorplan of the entire patient room, for example. The method of the eleventh aspect may further include determining a first number, N, of possible mounting locations for locating system anchors on a wall or ceiling of the patient room, wherein N may be at least three. The method of the eleventh aspect may also include successively placing a locating system anchor at each of the first number, N, of possible mounting locations, successively placing a portable locating tag at a second number, M, of locations along the boundary, wherein M may be at least two. Still further, the method of the eleventh aspect may also include transmitting a signal from the portable locating tag to the locating system anchor, determining N×M signal quality values, V, using a computer that may be coupled to the locating system anchor, each signal quality value, V, corresponding to a respective individual combination of possible mounting locations for the locating system anchor and the second locations along the boundary. The system of the eleventh aspect may also include performing an error sum of squares operation with the computer to optimize first and second mounting locations from among the N possible mounting locations for at least first and second locating system anchors based on the signal quality values, V.

In some embodiments of the eleventh aspect, the boundary of the area of interest is defined around a patient bed located in the patient room. For example, the boundary may be shaped as a rectangle around the patient bed. If desired, the second number, M, of locations may include six locations with four of the M locations corresponding to corners of the rectangle. Optionally, fourth and fifth locations of the M locations may correspond to midpoints of long sides of the rectangle. Further optionally, long sides and at least one short side of the rectangle may be spaced at least two feet from an outer periphery of the patient bed. If desired, N may include at least six locations and M may include at least six locations.

Optionally, performing an error sum of squares operation with the computer to optimize first and second mounting locations from among the N possible mounting locations for at least first and second locating system anchors may include performing an error sum of squares operation with the computer to optimize first, second, and third mounting locations from among the N possible mounting locations for at least first, second, and third locating system anchors. In some instances, the signal quality values, V, may include signal strength. Successively placing the locating system anchor at each of the first number, N, of possible mounting locations may include mounting the locating anchor to a wheeled stand and moving the wheeled stand successively so that the locating system anchor may be held by the wheeled stand at each of the first number, N, of possible mounting locations. If desired, transmitting the signal from the portable locating tag to the locating system anchor may include transmitting an ultra-wideband (UWB) signal.

According to a twelfth aspect of the present disclosure, a locating system may include a plurality of locating tags that may include an equipment locating tag that may be coupled to a piece of mobile medical equipment, a plurality of locating anchors that may be mounted at fixed locations and in wireless communication with the plurality of locating tags, and at least one computer that may be communicatively coupled to the plurality of locating anchors. The plurality of locating tags, the plurality of locating anchors, and the at least one computer of the twelfth aspect may cooperate to form a high-accuracy locating system operable to determine a location of each locating tag of the plurality of locating tags within at least one foot of an actual location of the locating tags. The equipment locating tag may have its role changed so as to operate as a locating anchor of the plurality of locating anchors in response to the piece of mobile medical equipment becoming stationary.

In some embodiments of the twelfth aspect, the piece of mobile medical equipment may send a signal to indicate that it has become stationary in response to a power cord of the piece of medical equipment being plugged into a power outlet. Alternatively, the piece of mobile medical equipment may include a patient bed and the patient bed may send a signal to indicate that it has become stationary in response to casters of the patient bed being braked. Further alternatively, the piece of mobile medical equipment may include a patient bed and the patient bed may send a signal to indicate that it has become stationary in response to casters of the patient bed being braked and a power cord of the patient bed being plugged into a power outlet. Still further alternatively, the piece of mobile medical equipment may include a patient bed and the patient bed may send a signal to indicate that is has become stationary in response to a nurse call cable of the patient bed being connected to a nurse call port located in a patient room.

Optionally, the piece of mobile medical equipment may include a patient bed and the equipment locating tag may be coupled to the patient bed near a foot end of the patient bed. Further optionally, the piece of mobile medical equipment may include a patient bed and the equipment locating tag may be coupled to a footboard of the patient bed. If desired, the piece of mobile medical equipment may be located in a patient room that may have two locating anchors at fixed locations and the equipment locating tag may become a third locating anchor in the patient room after its role is changed to operate as one of the locating anchors.

In some embodiments of the twelfth aspect, prior to changing its role to operate as one of the locating anchors, a location of the equipment locating tag may be determined by the at least one computer using two way ranging and time difference of arrival (TDOA) techniques. Alternatively or additionally, prior to changing its role to operate as one of the locating anchors, a location of the equipment locating tag may be determined by the at least one computer using time of arrival (TOA) or time of flight (TOF) techniques. Optionally, the equipment locating tag of the twelfth aspect may communicate with the plurality of locating anchors using ultra-wideband (UWB) signals. If desired, the at least one computer of the twelfth aspect may keep track of whether the equipment locating tag has changed roles to operating as one of the locating anchors.

According to a thirteenth aspect of the present disclosure, a locating method may include providing a plurality of locating tags including providing an equipment locating tag that may be coupled to a piece of mobile medical equipment, mounting a plurality of locating anchors at fixed locations, the locating anchors being configured for wireless communication with the plurality of locating tags, and providing at least one computer that may be communicatively coupled to the plurality of locating anchors. The plurality of locating tags, the plurality of locating anchors, and the at least one computer of the thirteenth aspect may cooperate to form a high-accuracy locating system that may be operable to determine a location of each locating tag of the plurality of locating tags within at least one foot of an actual location of the locating tags. The method of the thirteenth aspect may also include an changing a role of the equipment locating tag to operate as a locating anchor of the plurality of locating anchors in response to the piece of mobile medical equipment becoming stationary.

In some embodiments, the locating method of the thirteenth aspect may further include sending a signal from the piece of mobile medical equipment to indicate that it has become stationary in response to a power cord of the piece of medical equipment being plugged into a power outlet. Alternatively, the piece of mobile medical equipment may include a patient bed and the method of the thirteenth aspect may further include sending a signal from the patient bed to indicate that it has become stationary in response to casters of the patient bed being braked. Further alternatively, the piece of mobile medical equipment may include a patient bed and the method of the thirteenth aspect may further include sending a signal from the patient bed to indicate that it has become stationary in response to casters of the patient bed being braked and a power cord of the patient bed being plugged into a power outlet. Still further alternatively, the piece of mobile medical equipment may include a patient bed and the method of the thirteenth aspect may further include sensing a signal from the patient bed to indicate that is has become stationary in response to a nurse call cable of the patient bed being connected to a nurse call port located in a patient room.

Optionally, the piece of mobile medical equipment may include a patient bed and the method of the thirteenth aspect may further include coupling the equipment locating tag to the patient bed near a foot end of the patient bed. Further optionally, the piece of mobile medical equipment may include a patient bed and the method of the thirteenth aspect may further include coupling the equipment locating tag to a footboard of the patient bed. If desired, the piece of mobile medical equipment may be located in a patient room that may have two locating anchors at fixed locations and the equipment locating tag may become a third locating anchor in the patient room after changing its role to operate as one of the locating anchors.

In some embodiments, the locating method of the thirteenth aspect may further include, prior to changing the role of the equipment locating tag to operate as one of the locating anchors, determining a location of the equipment locating tag with the at least one computer using two way ranging and time difference of arrival (TDOA) techniques. Alternatively or additionally, prior to changing the role of the equipment locating tag to operate as one of the locating anchors, the method of the thirteenth aspect may include determining a location of the equipment locating tag with the at least one computer using time of arrival (TOA) or time of flight (TOF) techniques. Optionally, the equipment locating tag of the thirteenth aspect may communicate with the plurality of locating anchors using ultra-wideband (UWB) signals. If desired, the locating method of the thirteenth aspect may further include operating the at least one computer to keep track of whether the equipment locating tag has changed roles to operating as one of the locating anchors.

According to a fourteenth aspect of the present disclosure, a locating system may include a locating tag that may be transported by a person and that may have a digital compass. The digital compass may be used to determine a direction of orientation of the locating tag and may be used to establish a field of good ranging through a predetermined angle in front of the locating tag and away from the person's body. The locating system of the fourteenth aspect may also include a plurality of locating anchors that may be mounted at fixed locations within a facility and at least one computer that may be in communication with the plurality of locating anchors. The at least one computer may detect ranging events between the locating tag and the plurality of locating anchors. The at least one computer may determine a location of the locating tag using only the ranging events associated with each of the locating anchors that are within the field of good ranging established by the digital compass. The at least one computer may ignore the ranging events associated with each of the locating anchors that are not within the field of good ranging established by the digital compass.

In some embodiments of the fourteenth aspect, the at least one computer may be configured to use a least squares fit technique to determine the location of the locating tag. Optionally, if more than three locating anchors are within the field of good ranging, the at least one computer may be configured to determine the location of the locating tag using only the three locating anchors within the field of good ranging that have highest received power. Further optionally, if more than three locating anchors are within the field of good ranging, the at least one computer may be configured to determine the location of the locating tag using only the three locating anchors within the field of good ranging that have lowest sums of squared error.

It is contemplated that, if more than three locating anchors are within the field of good ranging of the fourteenth aspect, the at least one computer may be configured to determine the location of the locating tag using only the three locating anchors within the field of good ranging that have lowest variance. Alternatively, if more than three locating anchors are within the field of good ranging, the at least one computer may be configured to determine the location of the locating tag using only the three locating anchors within the field of good ranging that are closest to the locating tag.

In some embodiments of the fourteenth aspect, the at least one computer may be configured to ignore ranging events between the locating tag and any of the locating anchors within the field of good ranging that experience a sudden dip in received power. Optionally, the at least one computer may be configured to compare actual distances between respective pairs of the locating anchors and calculated distances between the respective pairs of locating anchors based on ranging events between the respective pairs of locating anchors and to determine correction factors for respective locating anchors to use on the ranging events with the locating tag to account for attenuation losses.

If desired, the location of the locating tag of the fourteenth aspect is determined by the at least one computer using two way ranging and time difference of arrival (TDOA) techniques. Alternatively or additionally, the location of the locating tag may be determined by the at least one computer of the fourteenth aspect using time of arrival (TOA) or time of flight (TOF) techniques. If desired, the equipment locating tag may communicate with the plurality of locating anchors of the fourteenth aspect using ultra-wideband (UWB) signals. Optionally, the predetermined angle of the field of good ranging may be at least 90 degrees. Further optionally, the predetermined angle of the field of good ranging may be at least 120 degrees.

In some embodiments of the fourteenth aspect, the at least one computer may determine if the person's body may be obstructing a signal path between the locating tag and one or more of the plurality of locating anchors by performing a fast Fourier transform (FFT) on multiple frequencies within an ultra-wideband spectrum and comparing ratios of received signal power to a transfer function of electromagnetic radiation through water. In some such embodiments, if the at least one computer determines that the person's body may be obstructing the signal path, the at least one computer may ignore the ranging event between the locating tag and the locating anchor that may be determined to be obstructed by the person's body. Alternatively or additionally, if the at least one computer determines that the person's body may be obstructing the signal path, the at least one computer may correct the ranging event to account for refraction through the person's body.

According to a fifteenth aspect of the present disclosure, a locating method may include providing a locating tag to be transported by a person and having a digital compass, using the digital compass to determine a direction of orientation of the locating tag, using the digital compass to establish a field of good ranging through a predetermined angle in front of the locating tag and away from the person's body, providing a plurality of locating anchors that may be mounted at fixed locations within a facility, and providing at least one computer in communication with the plurality of locating anchors. The method of the fifteenth aspect may also include using the at least one computer to detect ranging events between the locating tag and the plurality of locating anchors, determining with the at least one computer a location of the locating tag using only the ranging events associated with each of the locating anchors that may be within the field of good ranging established by the digital compass, and with the at least one computer, ignoring the ranging events associated with each of the locating anchors that may not be within the field of good ranging established by the digital compass.

In some embodiments, the locating method of the fifteenth aspect may further include, with the at least one computer, using a least squares fit technique to determine the location of the locating tag. Optionally, the locating method of the fifteenth aspect my further include, if more than three locating anchors are within the field of good ranging, using the at least one computer to determine the location of the locating tag using only the three locating anchors within the field of good ranging that may have highest received power and/or that may have lowest sums of squared error and/or that may have lowest variance and/or that may be closest to the locating tag.

If desired, the locating method of the fifteenth aspect may further include, with the at least one computer, ignoring ranging events between the locating tag and any of the locating anchors within the field of good ranging that may experience a sudden dip in received power. It is contemplated that the locating method of the fifteenth aspect may further include, with the at least one computer, comparing actual distances between respective pairs of the locating anchors and calculated distances between the respective pairs of locating anchors based on ranging events between the respective pairs of locating anchors and determining correction factors for respective locating anchors to use on the ranging events with the locating tag to account for attenuation losses.

In some embodiments, the locating method of the fifteenth aspect may further include determining the location of the locating tag by the at least one computer using two way ranging and time difference of arrival (TDOA) techniques. Alternatively or additionally, the locating method of the fifteenth aspect may further include determining the location of the locating tag by the at least one computer using time of arrival (TOA) or time of flight (TOF) techniques. If desired, the equipment locating tag of the fifteenth aspect may communicate with the plurality of locating anchors using ultra-wideband (UWB) signals. Optionally, the predetermined angle of the field of good ranging may be at least 90 degrees. Further optionally, the predetermined angle of the field of good ranging may be at least 120 degrees.

Optionally, the locating method of the fifteenth aspect may further include using the at least one computer to determine if the person's body may be obstructing a signal path between the locating tag and one or more of the plurality of locating anchors by performing a fast Fourier transform (FFT) on multiple frequencies within an ultra-wideband spectrum and comparing ratios of received signal power to a transfer function of electromagnetic radiation through water. If the at least one computer determines that the person's body may be obstructing the signal path, the method of the fifteenth aspect may include ignoring with the at least one computer the ranging event between the locating tag and the locating anchor that may be determined to be obstructed by the person's body. Alternatively, if the at least one computer determines that the person's body may be obstructing the signal path, the method of the fifteenth aspect may include correcting the ranging event with the at least one computer to account for refraction through the person's body.

According to a sixteenth aspect of the present disclosure, a locating and bed control system may include a bed configured to support a patient thereon. The bed may have at least one sensor to monitor a bed condition and generate an alarm if the bed condition is sensed to be in an alarm state by the at least one sensor. The system of the sixteenth aspect may also include an equipment locating tag that may be coupled to the bed, a caregiver locating tag that may be coupled to a caregiver, a plurality of receivers that may be mounted at fixed locations and in wireless communication with the equipment locating tag and the caregiver locating tag, and at least one computer that may be communicatively coupled to the plurality of receivers. The equipment locating tag, the caregiver locating tag, the plurality of receivers, and the at least one computer of the sixteenth aspect may cooperate to form a high-accuracy locating system that may be operable to determine a location of the equipment locating tag and the caregiver locating tag within at least one foot of an actual location of the equipment locating tag and the caregiver locating tag, respectively. The at least one computer of the sixteenth aspect may model a patient contact zone that may be adjacent the bed based on the location of the equipment locating tag. The at least one computer of the sixteenth aspect may signal the bed to suppress monitoring of the bed condition by the at least one sensor in response to the caregiver locating tag being detected in the patient contact zone and the at least one computer also may determine that the caregiver may have successfully completed a caregiver round in response to the caregiver locating tag being detected in the patient contact zone.

In some embodiments of the sixteenth aspect, the at least one sensor may include a patient position monitoring (PPM) sensor and the alarm may be generated in response to the PPM sensor detecting that the patient may have moved toward exiting the bed by a threshold amount. Thus, after monitoring of the bed condition by the PPM sensor has been suppressed by the at least one computer, the caregiver may be able to assist the patient in getting out of the bed without the alarm being generated. If desired, the PPM sensor may be re-enabled to monitor for the alarm condition in response to the patient being returned to bed and the caregiver locating tag being detected to have left the patient contact zone.

Optionally, the bed of the sixteenth aspect may include a nurse call input that may be selectable by the patient to place a nurse call and the at least one computer may be configured to send a message to cancel the nurse call in response to the caregiver locating tag being detected in the patient contact zone. Alternatively or additionally, generation of the alarm may result in a nurse call being sent from the bed to a nurse call computer and the at least one computer may be configured to send a message to the nurse call computer to cancel the nurse call in response to the caregiver locating tag being detected in the patient contact zone.

In some embodiments, the bed is located in a patient room and the system of the sixteenth aspect may further include a second bed located in the patient room. In such embodiments, the at least one computer may be configured to determine that the caregiver may have successfully completed caregiver rounds for the patient on the bed and for a second patient on the second bed in response to the caregiver locating tag being detected in the patient contact zone adjacent the bed or in response to the caregiver locating tag being detected in a second patient contact zone adjacent the second bed.

It is contemplated by the present disclosure that the patient contact zone of the sixteenth aspect may be defined as being within a boundary that may be about three feet from a periphery of the bed. For example, the patient contact zone may be defined as being within a boundary calculated as being about three feet away from a footprint of the bed as theoretically projected onto a floor supporting the bed. Alternatively, the patient contact zone of the sixteenth aspect may be defined as being within a circular boundary having a radius of about five feet and centered on the equipment locating tag. Further alternatively, the patient contact zone of the sixteenth aspect may be defined as being within an ellipse-shaped boundary that may extend beyond both sides and both ends of the bed.

In some embodiments, the equipment locating tag and the caregiver locating tag of the sixteenth aspect may communicate with the plurality of receivers via ultra-wideband (UWB) signals. If desired, the locations of the equipment locating tag and the caregiver locating tag of the sixteenth aspect may be determined by the at least one computer using two way ranging and time difference of arrival (TDOA) techniques. Alternatively or additionally, the locations of the equipment locating tag and the caregiver locating tag of the sixteenth aspect may be determined by the at least one computer using time of arrival (TOA) at which transmissions from the equipment locating tag and the caregiver locating tag are received at the plurality of receivers.

Optionally, the at least one computer of the sixteenth aspect may use signals from only a subset of the plurality of receivers to determine the location of the equipment locating tag and the caregiver locating tag. The subset of the sixteenth aspect may be determined based on signal strength of signals from the equipment locating tag and the caregiver locating tag to the plurality of receivers. For example, the subset may include at least three receivers from the plurality of receivers of the sixteenth aspect having highest signal strength values as compared to others of the plurality of receivers.

In some embodiments, the at least one sensor of the sixteenth aspect may be configured to sense a presence of a patient on the bed and the at least one computer may be configured to determine that a successful caregiver round may have occurred only if the patient is present on the bed as sensed by the sensor. It is contemplated by the present disclosure that the locating and bed control system of the sixteenth aspect may further include a patient locating tag that may be coupled to a patient and the at least one computer may be configured to determine that a successful caregiver round may have occurred only if the patient locating tag is determined to be within the patient contact zone with the caregiver locating tag.

According to a seventeenth aspect of the present disclosure, a locating and bed control method may include providing a bed that may be configured to support a patient thereon. The bed may have at least one sensor to monitor a bed condition and generate an alarm if the bed condition is sensed to be in an alarm state by the at least one sensor. The method of the seventeenth aspect may further include providing an equipment locating tag that may be coupled to the bed, providing a caregiver locating tag that may be coupled to a caregiver, providing a plurality of receivers that may be mounted at fixed locations and in wireless communication with the equipment locating tag and the caregiver locating tag, and providing at least one computer that may be communicatively coupled to the plurality of receivers. The equipment locating tag, the caregiver locating tag, the plurality of receivers, and the at least one computer of the seventeenth aspect may cooperate to form a high-accuracy locating system that may be operable to determine a location of the equipment locating tag and the caregiver locating tag within at least one foot of an actual location of the equipment locating tag and the caregiver locating tag, respectively. The method of the seventeenth aspect may also include modeling with the at least one computer a patient contact zone that may be adjacent the bed based on the location of the equipment locating tag. The method of the seventeenth aspect may further include, with the at least one computer, sending a signal to the bed to suppress monitoring of the bed condition by the at least one sensor in response to the caregiver locating tag being detected in the patient contact zone and, with the at least one computer, determining that the caregiver may have successfully completed a caregiver round in response to the caregiver locating tag being detected in the patient contact zone.

In some embodiments of the seventeenth aspect, the at least one sensor may include a patient position monitoring (PPM) sensor and the method may further include generating the alarm in response to the PPM sensor detecting that the patient may have moved toward exiting the bed by a threshold amount. Thus, after monitoring of the bed condition by the PPM sensor has been suppressed by the at least one computer, the method of the seventeenth aspect may further include assisting the patient in getting out of the bed without the alarm being generated. If desired, the locating and bed control method of the seventeenth method may further include re-enabling the PPM sensor to monitor for the alarm condition in response to the patient being returned to bed and the caregiver locating tag being detected to have left the patient contact zone.

Optionally, the bed of the seventeenth aspect may include a nurse call input that may be selectable by the patient to place a nurse call and the method may further include, with the at least one computer, sending a message to cancel the nurse call in response to the caregiver locating tag being detected in the patient contact zone. Alternatively or additionally, generation of the alarm results in a nurse call being sent from the bed to a nurse call computer and the method of the seventeenth aspect may further include, with the at least one computer, sending a message to the nurse call computer to cancel the nurse call in response to the caregiver locating tag being detected in the patient contact zone.

In some embodiments, the bed is located in a patient room and the method of the seventeenth aspect may further include providing a second bed located in the patient room. The method of the seventeenth aspect may also include determining with the at least one computer that the caregiver may have successfully completed caregiver rounds for the patient on the bed and for a second patient on the second bed in response to the caregiver locating tag being detected in the patient contact zone adjacent the bed or in response to the caregiver locating tag being detected in a second patient contact zone adjacent the second bed.

It is contemplated by the present disclosure that the patient contact zone of the seventeenth aspect may be defined as being within a boundary that may be about three feet from a periphery of the bed. For example, the patient contact zone of the seventeenth aspect may be defined as being within a boundary calculated as being about three feet away from a footprint of the bed as theoretically projected onto a floor supporting the bed. Alternatively, the patient contact zone of the seventeenth aspect may be defined as being within a circular boundary having a radius of about five feet and centered on the equipment locating tag. Further alternatively, the patient contact zone of the seventeenth aspect may be defined as being within an ellipse-shaped boundary that may extend beyond both sides and both ends of the bed.

In some embodiments, the equipment locating tag and the caregiver locating tag of the seventeenth aspect communicate with the plurality of receivers via ultra-wideband (UWB) signals. If desired, the locating and bed control method of the seventeenth aspect may further include determining the locations of the equipment locating tag and the caregiver locating tag with the at least one computer using two way ranging and time difference of arrival (TDOA) techniques. Alternatively or additionally, the locating and bed control method of the seventeenth aspect may further include determining the locations of the equipment locating tag and the caregiver locating tag with the at least one computer using time of arrival (TOA) at which transmissions from the equipment locating tag and the caregiver locating tag are received at the plurality of receivers.

Optionally, the at least one computer of the seventeenth aspect may use signals from only a subset of the plurality of receivers to determine the location of the equipment locating tag and the caregiver locating tag. The subset of the seventeenth aspect may be determined based on signal strength of signals from the equipment locating tag and the caregiver locating tag to the plurality of receivers. For example, the subset of the seventeenth aspect may include at least three receivers from the plurality of receivers having highest signal strength values as compared to others of the plurality of receivers.

In some embodiments, the at least one sensor of the seventeenth aspect may be configured to sense a presence of a patient on the bed and the at least one computer may be configured to determine that a successful caregiver round may have occurred only if the patient is present on the bed as sensed by the sensor. It is contemplated by the present disclosure that the locating and bed control method of the seventeenth aspect may further include providing a patient locating tag that may be coupled to a patient and the at least one computer may be configured to determine that a successful caregiver round may have occurred only if the patient locating tag is determined to be within the patient contact zone with the caregiver locating tag.

According to an eighteenth aspect of the present disclosure, a locating system may include a plurality of locating tags that may be coupled to personnel within a facility, a plurality of locating anchors that may be mounted at fixed locations and in wireless communication with the plurality of locating tags, and a plurality of processing hubs that may be communicatively coupled to subsets of the plurality of locating anchors. The plurality of locating tags, the plurality of locating anchors, and the processing hubs of the eighteenth aspect may cooperate to form a high-accuracy locating system operable to determine a location of each locating tag of the plurality of locating tags within at least one foot of an actual location of the locating tags and the high-accuracy locating system may be devoid of any locating server.

In some embodiments, the locating system of the eighteenth aspect may further include a plurality of medical devices. The locating hubs may be configured to send location data to one or more medical devices of the plurality of medical devices of the eighteenth aspect. Alternatively or additionally, the processing hubs of the eighteenth aspect may be configured to send commands to one or more medical devices of the plurality of medical devices to control a feature of the medical device. If desired, the commands may be sent to the one or more medical devices by the processing hubs in response to a first locating tag of the plurality of locating tags being located within a device zone of the respective medical devices. At least one of the commands may be an alarm silence command to silence an alarm of the respective medical device, for example. Alternatively or additionally, at least one of the commands may be a nurse call cancel command to cancel a nurse call originating from the respective medical device. Optionally, the plurality of medical devices of the eighteenth aspect may include one or more of the following: a hospital bed, a vital signs monitor, an intravenous (IV) pump, a mattress controller, a deep vein thrombosis (DVT) therapy device, a passive motion machine, a pulse oximeter, or a patient lift.

It is contemplated by the present disclosure that each processing hub of the eighteenth aspect may be communicatively coupled to at least two locating anchors. If desired, each locating tag of the eighteenth aspect may include a radio frequency (RF) transmitter and each locating anchor may include an RF receiver. Optionally, the locating tags of the eighteenth aspect may communicate with the plurality of locating anchors via ultra-wideband (UWB) signals. The locations of the locating tags of the eighteenth aspect may be determined by the plurality of processing hubs using two way ranging and time difference of arrival (TDOA) techniques. Alternatively or additionally, the locations of the locating tags of the eighteenth aspect may be determined by the plurality of processing hubs using time of arrival (TOA) at which transmissions from the locating tags are received at the plurality of locating anchors or using time of flight (TOF) of transmissions between the locating tags and the plurality of locating anchors.

In some embodiments of the eighteenth aspect, each processing hub of the plurality of processing hubs may use signals from only a subset of the plurality of locating anchors to determine the location of the locating tags. For example, the subset of the eighteenth aspect may be determined based on signal strength of signals from the locating tags to each locating anchor of the plurality of locating anchors. If desired, the subset of the eighteenth aspect may include at least three locating anchors from the plurality of locating anchors having highest signal strength values as compared to others of the plurality of locating anchors.

According to a nineteenth aspect of the present disclosure, a locating method may include providing a plurality of locating tags that may be coupled to personnel within a facility, providing a plurality of locating anchors that may be mounted at fixed locations and in wireless communication with the plurality of locating tags, and providing a plurality of processing hubs that may be communicatively coupled to subsets of the plurality of locating anchors. The plurality of locating tags, the plurality of locating anchors, and the processing hubs of the nineteenth aspect may cooperate to form a high-accuracy locating system that may be operable to determine a location of each locating tag of the plurality of locating tags within at least one foot of an actual location of the locating tags and the high-accuracy locating system may be devoid of any locating server.

In some embodiments, the locating method of the nineteenth aspect further includes providing a plurality of medical devices and sending location data from the plurality of processing hubs to one or more medical devices of the plurality of medical devices. Alternatively or additionally, the locating method of the nineteenth aspect may further include providing a plurality of medical devices and sending commands from the plurality of processing hubs to one or more medical devices of the plurality of medical devices to control a feature of the medical device. If desired, the commands may be sent to the one or more medical devices by the processing hubs in response to a first locating tag of the plurality of locating tags being located within a device zone of the respective medical devices. At least one of the commands may be an alarm silence command to silence an alarm of the respective medical device, for example. Alternatively or additionally, at least one of the commands may be a nurse call cancel command to cancel a nurse call originating from the respective medical device. Optionally, the plurality of medical devices may include one or more of the following: a hospital bed, a vital signs monitor, an intravenous (IV) pump, a mattress controller, a deep vein thrombosis (DVT) therapy device, a passive motion machine, a pulse oximeter, or a patient lift.

It is contemplated by the present disclosure that each processing hub of the nineteenth aspect may be communicatively coupled to at least two locating anchors. If desired, each locating tag of the nineteenth aspect may include a radio frequency (RF) transmitter and each locating anchor may include an RF receiver. Optionally, the locating tags of the nineteenth aspect may communicate with the plurality of locating anchors via ultra-wideband (UWB) signals. Alternatively or additionally, the locating method of the nineteenth aspect may further include determining the locations of the locating tags by the plurality of processing hubs using two way ranging and time difference of arrival (TDOA) techniques. Further alternatively or additionally, the locating method of the nineteenth aspect may further include determining the locations of the locating tags by the plurality of processing hubs using time of arrival (TOA) at which transmissions from the locating tags are received at the plurality of locating anchors or using time of flight (TOF) of transmissions between the locating tags and the plurality of locating anchors.

In some embodiments of the nineteenth aspect, each processing hub of the plurality of processing hubs may use signals from only a subset of the plurality of locating anchors to determine the locations of the locating tags. For example, the subset of the nineteenth aspect may be determined based on signal strength of signals from the locating tags to each locating anchor of the plurality of locating anchors. If desired, the subset of the nineteenth aspect may include at least three locating anchors from the plurality of locating anchors having highest signal strength values as compared to others of the plurality of locating anchors.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
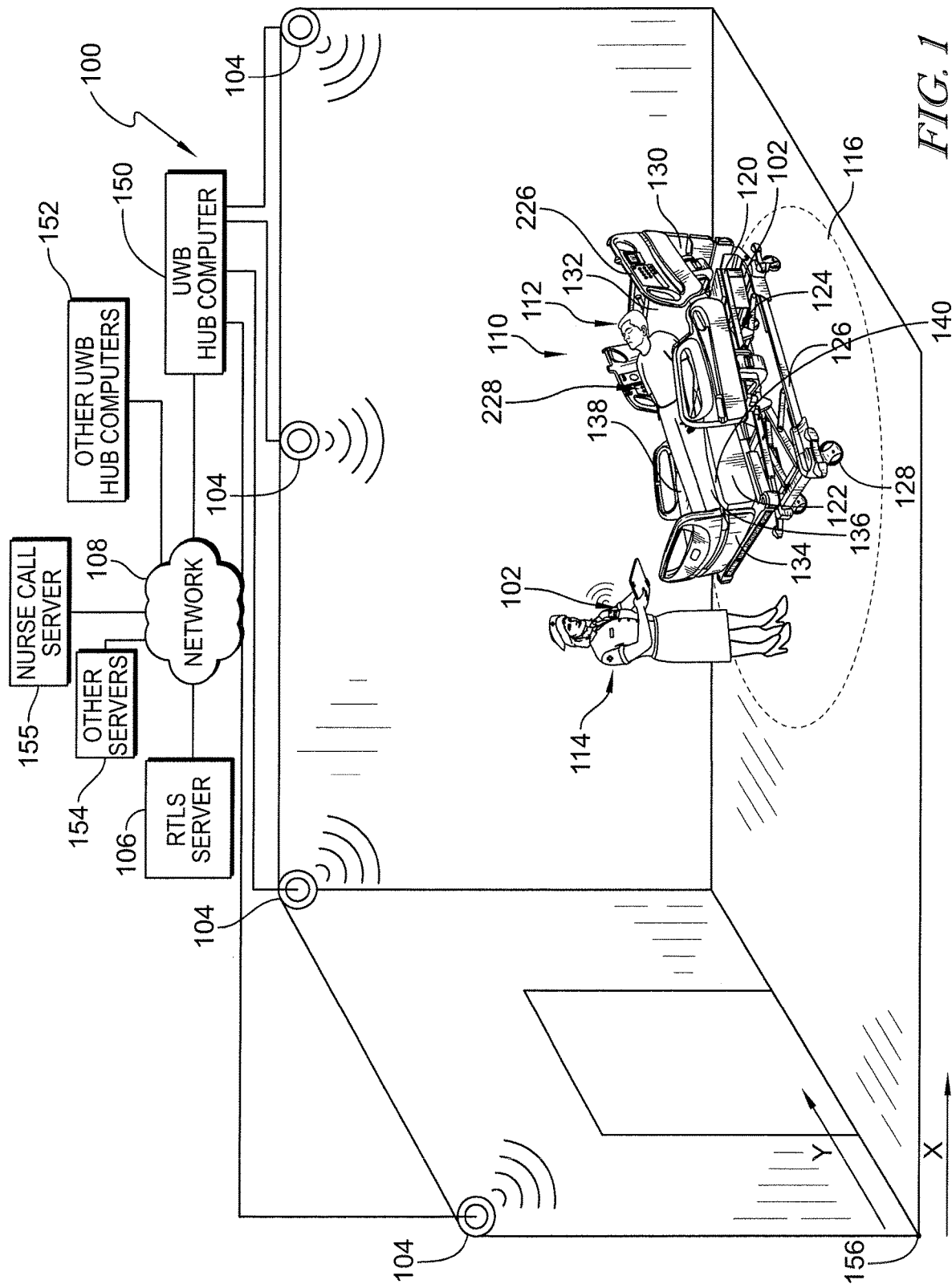
FIG. 1 is diagrammatic view of a caregiver rounding system showing a bed on which a patient is supported and a high-accuracy real time locating system (RTLS) including a plurality of tags, a plurality of ultra-wideband (UWB) locating receivers or transceivers wirelessly communicating with the plurality of tags, a UWB hub computer in communication with the UWB receivers, and an RTLS server in communication with UWB hub computer via a network, and showing a rounding zone (dotted line) around the bed in which a caregiver is standing.

A caregiver rounding system 100 of a healthcare facility is configured to determine successful rounds of a caregiver 114 when attending to each patient 112 of the caregiver's assigned patients. In some embodiments, a successful round occurs based on system 100 determining proximity of the caregiver 114 to the respective patient 112, for a predetermined amount of time, within a zone 116 adjacent to a patient support apparatus 110 that is configured to support the patient 112 as shown in FIG. 1. Thus, if the caregiver 114 is assigned to the patient 112, then a successful caregiver round occurs when the caregiver 114 is located within zone 116 for the predetermined period of time, such as two minutes or five minutes, for example. Although the following description relates to one patient 112 on one bed 110 in one patient room, it should be appreciated that the caregiver 114 is assigned to multiple patients 112 in multiple patient rooms and each room may have a rounding zone 116 around or near the respective bed 110 for determining successful caregiver rounds for each assigned patient.

The illustrated patient support apparatus 110 is embodied as a patient bed 110. However, it should be appreciated that this disclosure is applicable to other types of patient support apparatuses, including other types of beds, surgical tables, examination tables, stretchers, chairs, wheelchairs, patient lifts, and the like. In the description below, patient support apparatus 110 is sometimes referred to as patient bed 110 or just bed 110. However, the description is equally applicable to other types of patient support apparatuses 110 in a healthcare facility.

The overall system 100 is subdivided into sub-systems which are themselves, also referred to herein as "systems." For example, system 100 includes a locating system, sometimes referred to as a real time locating system (RTLS) in the art, that tracks the locations of caregivers and equipment throughout the healthcare facility. In some embodiments, the locating system is embodied as a high-accuracy locating system such as an ultra-wideband (UWB) locating system, but this need not be the case in other embodiments of high-accuracy locating systems such as those using radio detection and ranging (RADAR) equipment or cameras and/or other imaging equipment or other high-accuracy locating technologies.

The illustrative locating system includes a plurality of receivers or transceivers 104 positioned throughout the healthcare facility such as in the patient room of FIG. 1, in the hallway of the healthcare facility, and in other locations throughout the healthcare facility (e.g, staff break rooms, bathrooms, pharmacy, treatment rooms, operating rooms, imaging rooms, laboratories, cafeteria, etc.) at the discretion of the system designer. Transceivers 104 each include a receiver and a transmitter. However, in some embodiments, receivers 104 receive wireless transmissions but do not send wireless transmissions. In either case, receivers 104 and transceivers 104, as the case may be, are each configured to receive wireless transmissions. Transceivers 104 and receivers 104 are each communicatively coupled to other components of the locating system as will be discussed herein such as by use of wired connections like Ethernet cables or other cables.

The transceivers 104 or receivers 104, as the case may be, receive wireless transmissions from caregiver locating tags 102 that are worn by respective caregivers 114 and from equipment tags 102 that are attached to various pieces of equipment such as patient beds 110. Thus, when tag 102 is worn or carried by a caregiver, it is considered to be a caregiver locating tag 102 and when tag 102 is attached to equipment, it is considered to be an equipment locating tag 102. Similarly, when tag 102 is worn or carried by a patient, it is considered to be a patient locating tag 102. In the example of FIG. 1, the caregiver locating tag 102 is coupled to the clothing of the caregiver 114, such as with a clip, and the equipment locating tag 102 is attached to the patient bed 110 such as with a fastener (e.g., bolt, screw, snap, hook-and-loop fastener, adhesive, magnet, etc.). Caregiver locating tags 102 may instead be worn around the respective caregivers' necks on a necklace or attached to the caregivers' wrists on a wristband or bracelet, for example.

In some embodiments, the tags 102 receive a signal from the transmitter circuitry of one or more of the transceivers 104 and, in response, transmit a return signal to at least one of the transceivers 104. The return signal includes a tag identification (ID) which is unique to each tag 102. Such an arrangement preserves battery life of tags 102 because transmissions of tag ID's are only made by the tags 102 when in communicative proximity of one or more transceivers 104 and after receiving a request signal from at least one of the transceivers 104. In other embodiments, tags 102 operate to transmit their respective tag ID's on a periodic basis for receipt by receivers 104 or transceivers 104, as the case may be. In still other embodiments, short range wireless beacons or infrared transmitters are mounted at fixed locations throughout the healthcare facility and send a signal with a location ID to the tags 102 that are in the vicinity of the short range beacons and, in response to receipt of the signal, the tags 102 transmit their respective tag ID's and the location ID's to transceivers 104 or receivers 104. In each of these embodiments, transceivers 104 or receivers 104 transmit the received tag ID or tag ID's if multiple tags are present, to an RTLS server 106 of the locating system along with a respective transceiver ID and, if applicable, the location ID.

In some embodiments, the transceiver ID's or receiver ID's correlate to particular locations in the healthcare facility. Thus, the RTLS server 106 determines the locations of tags 102 within the healthcare facility by correlating the tag ID's with the transceiver or receiver ID's (and/or the location ID's, if applicable) and, ultimately, with the location correlated with the transceiver or receiver ID's and/or location ID's. RTLS server 106 also correlates the tag ID's with the respective caregivers wearing tags 102 and with the equipment to which tags 102 are attached, as the case may be. In some embodiments, patients 112 also have tags 102 for tracking the whereabouts of the patients 112 throughout the healthcare facility as alluded to above. Thus, in some embodiments, the locating system of overall system 100 includes tags 102, transceivers 104 (or receivers 104), and RTLS server 106. Tags 102 are sometimes referred to as "badges" and so the terms "tag" and "badge" are used interchangeably herein.

Figure 2:
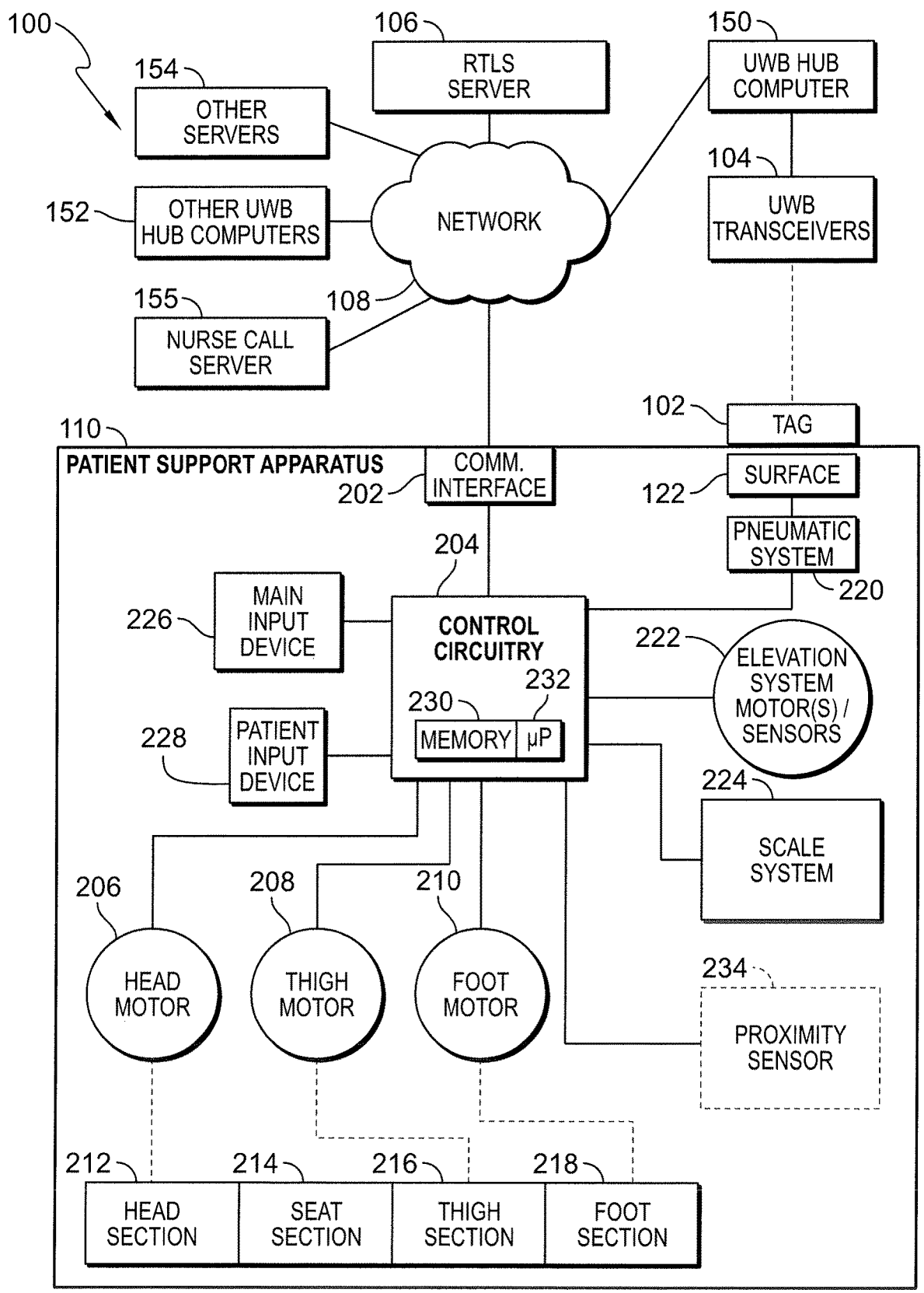
FIG. 2 is a block diagram showing electrical circuitry of the bed and showing an equipment locating tag of the plurality of tags on the bed and in communication with one or more UWB transceivers of the high-accuracy RTLS.

System 100 includes network infrastructure which is designated diagrammatically as network 108 in FIGS. 1 and 2. Network 108 is intended to represent the infrastructure (e.g., wireless access points, Ethernet jacks such as RJ-45 connectors, wires, routers, gateways, etc.) provided in a healthcare facility and the various computer devices (e.g., personal computers, servers, laptop computers, patient care equipment, etc.) that are coupled to the infrastructure. The various subsystems described herein include components that may communicate with each other using portions of network 108. In the illustrative example, transceivers 104 or receivers 104 communicate with RTLS server 106 via portions of network 108. In the description that follows, the term transceiver 104 will be used but the description is equally applicable to embodiments having receivers 104 unless specifically noted otherwise.

In some embodiments, tags 102 communicate wirelessly with transceivers 104 using infrared (IR) technology. In such embodiments, line of sight between tags 102 and one or more of transceivers 104 needs to remain unobstructed in order for communication to be established between the tags 102 and one or more of the transceivers 104 to determine the location of the tags 102 in the healthcare facility. Thus, the IR signals cannot pass through walls, equipment, and people located in the room. In general, locating systems that use IR communication between tags 102 and transceivers 104 are able to reliably determine that the tags 102 are located inside a particular room, but are not able to determine the exact location, within a relatively small accuracy threshold, of the tag 102 within the room.

As noted above, the locating system in some embodiments is embodied as a high-accuracy locating system such as an ultra-wideband (UWB) locating system. In such embodiments, tags 102 are configured as UWB tags 102 having UWB transceivers or transmitters, and transceivers 104 are configured as UWB transceivers or UWB receivers. The description that follows refers to UWB transceivers 104 but is equally applicable to embodiments using UWB receivers 104 unless specifically noted otherwise.

The UWB transceivers 104 are stationary and the UWB transceivers of tags 102 are mobile, but their circuitry otherwise may be substantially the same. Thus, tags 102 and transceivers 104 each include a housing that contains associated circuitry. The circuitry of tags 102 and transceivers 104 includes, for example, a processor such as a microprocessor or microcontroller or the like, memory for storing software, and communications circuitry including a transmitter, a receiver and at least one antenna. Transceivers 104 each include mounting hardware, such as brackets or plates or the like, in some embodiments, to permit the transceivers 104 to be mounted at fixed locations in the patient rooms and other locations of the healthcare facility with fasteners such as screws or the like.

In the illustrative example of system 100 of FIG. 1, the high-accuracy locating system further includes a UWB hub computer 150 which is communicatively coupled to other UWB hub computers 152 of the high-accuracy locating system via network 108 of the healthcare facility. UWB hub computer 150 serves as an intermediary between transceivers 104 and RTLS server 106. Of course, the other UWB hub computers 152 are also communicatively coupled to respective sets of transceivers 104. In the illustrative example, the high-accuracy locating system is also communicatively coupled to a nurse call server 155 and to other servers or computers 154 of the healthcare facility, such as to an EMR server or an admission/discharge/transfer (ADT) computer, just to name a couple. Nurse call server 155 is configured to determine and/or monitor whether caregivers 114 have successfully completed their rounds and to control the display of rounding information on various display devices such as an electronic status board, a master nurse call station, a caregiver mobile device (e.g., a caregiver's mobile phone), and graphical room stations of the nurse call system. The other servers and computers 154 block in FIGS. 1 and 2, generically represents all other computers and servers of network 108 in a healthcare facility.

As shown diagrammatically in FIG. 1, various lines interconnect transceivers 104 with hub computer 150 and interconnect servers and computers 106, 152, 154 with each other via network 108. It should be appreciated that these lines represent bidirectional communication over wired data links (including electrical wires such as Ethernet cables or fiber optic data links) and/or wireless data links, at the discretion of the designer of system 100. UWB transceivers 104 communicate wirelessly with tags 102 using radio frequency (RF). It is known that RF signals are able to pass through walls, ceilings, floors, and other objects such as people and equipment. Thus, according to this disclosure, it is not required that each patient room has a transceiver 104 located therein in those embodiments of the locating system using RF communication.

According to this disclosure, the portion of system 100 that operates as a high-accuracy locating system using UWB technology is able to determine the location of each tag 102 that is in communication with at least three of transceivers 104 within about one foot (30.48 cm) or less of the tag's actual location. In other embodiments, the locating system is able to determine the location of each tag 102 that is in communication with at least three of transceivers 104 within about three feet (91.44 cm) or less of the tag's actual location and such embodiments are still considered to be high-accuracy locating systems according to the present disclosure.

In some embodiments, the high-accuracy locating system is operable to determine the location of tags 102 in 3-dimensional space. However, in many embodiments, it suffices to determine the location of tags 102 in 2-dimensional space. Accordingly, FIG. 1 shows X and Y directions relative to a floor plan of the healthcare facility with point 156 serving as an arbitrary origin of an X-Y coordinate system. The Z dimension corresponds to a height in a Z direction (not shown) above the floor plan of FIG. 1. UWB locating systems typically operate within the 3.1 gigahertz (GHz) to 10.6 GHz frequency range. Suitable transceivers 104 in this regard include WISER Mesh Antenna Nodes and suitable tags 102 in this regard include Mini tracker tags, all of which are available from Wiser Systems, Inc. of Raleigh, N.C. and marketed as the WISER LOCATOR™ system.

In some embodiments, the high-accuracy locating system implementing UWB technology uses 2-way ranging, clock synchronization, and time difference of arrival (TDOA) techniques to determine the locations of tags 102 in the X and Y directions (and, optionally, the Z direction in some embodiments). See, for example, International Publication No. WO 2017/083353 A1, which is hereby incorporated by reference herein in its entirety for all that it teaches to the extent not inconsistent with the present disclosure which shall control as to any inconsistencies, for a detailed discussion of the use of these techniques in a UWB locating system. Using these techniques, distances between the stationary transceivers 104 and the various mobile tags 102 are determined based on bidirectional wireless signals communicated between tags 102 and transceivers 104. For example, the distance from each transceiver 104 to any particular tag 102 can be resolved onto the X-Y plane as a circle having a radius equal to the distance and having its center at the particular transceiver 104. The actual location of the mobile tag 102 is determined based on the point of intersection of three or more of the circles defined by radii from three or more corresponding transceivers 104.

The location of each stationary transceiver 104 is mapped onto the X-Y coordinate system by server 106. Thus, each transceiver has its own X and Y coordinates relative to origin 156. As the mobile tags 102 move throughout the healthcare facility, server 106 determines the X and Y coordinates of the various mobile tags 102 relative to origin 156 based on the distances from the known X and Y coordinates of the transceivers 104. In some embodiments, multiple origins similar to origin 156 are programmed in server 106 and the X and Y coordinates of tags 102 are calculated with respect to the closest origin. For example, each hub 150, 152 is associated with a respective unique origin in some embodiments.

It should be appreciated that, unless a tag 102 is midway between two transceivers 104 on a straight line connecting the two transceivers 104 (in which case the two circles generated will be tangent to each other at a single point), then two circles that are generated from the two transceivers 104 will intersect at two points such that a circle generated from a third transceiver 104 is needed to determine which of the two points is the one corresponding to the location of the tag 102. Generating fourth, fifth, sixth, etc. circles having other transceivers 104 as their respective centers will further increase the accuracy of determining the actual location of the particular tag 102. Due to small errors introduced by refraction of the RF signal through solid objects, including walls, people, equipment, etc., the three or more circles in many instances will not intersect at exactly the same point and so interpolation between clusters of circle intersections is performed to arrive at the calculated location of the particular mobile tag 102 of interest on the X-Y plane. These considerations are discussed in International Publication No. WO 2017/083353 A1 which is already incorporated by reference herein.

Tracking the locations of multiple mobile tags 102 in substantially real time using 2-way ranging, clock synchronization, TDOA, resolution of circles onto the X-Y plane, and interpolating intersection point clusters of the circles requires a large amount of computational power by hub computers 150, 152 and/or the associated RTLS server 106. Thus, each hub computer 150, 152 of the high-accuracy locating system receives incoming data from a predetermined number of transceivers 104. In the illustrative example of FIG. 1, hub computer 150 receives data from four transceivers 104. TDC Acquisition Holdings, Inc. of Huntsville, Ala. which does business as Time Domain, makes a hub computer (referred to as the PLUS Synchronization Distribution Panel) that is capable of receiving incoming data from up to 144 transceivers. The locating server or computer 106, in turn, receives data from the various hubs 150, 152 and tracks or monitors the locations of tags 102 in the healthcare facility. In some embodiments, the high accuracy locating system uses time of flight (TOF) techniques and/or time of arrival (TOA) techniques rather than TDOA techniques to determine the locations of tags 102.

Regardless of the number of transceivers 104 coupled to hub computers 150, 152, it is contemplated by the present disclosure that, in some embodiments, locating server 106 and/or hub computers 150, 152 are programmed to use signals from only a subset of the plurality of transceivers 104 to determine the location of any given locating tag 102. For example, the subset may be determined based on signal strength of signals between the particular locating tag 102 and the plurality of transceivers 104. The subset may include at least three transceivers 104 from the plurality of transceivers 104 having highest signal strength values as compared to others of the plurality of transceivers 104.

The caregiver rounding system 100 shown in FIG. 1 includes caregiver locating tags 102 worn by caregivers 114 and equipment locating tag 102 mounted to patient support apparatus 110. Transceivers 104 are configured to receive wireless signals from the tags 102 and the computer 150 and/or server 106 determines locations of the respective caregivers 114 and the patient support apparatus 110 with high-accuracy. Thus, the locations of tags 102 are considered to be the locations of the respective caregivers 114 and patient support apparatus 110. That is, server 106 determines the X and Y coordinates of each of tags 102 relative to origin 156. In some embodiments, the high-accuracy locating system portion of caregiver rounding system 100 determines a location of each tag 102 within about three feet or less, such as about one foot, of the actual location of the respective tag 102.

As mentioned above, a successful round occurs based on system 100 determining that the caregiver 114 assigned to care for the respective patient 112 is within a rounding zone 116 adjacent to the patient support apparatus 110 for a predetermined amount of time. In FIG. 1, caregiver 114 is depicted as being within zone 116. Thus, zone 116 is delineated by a set of points having X and Y coordinates that are stored in one or more computer devices of system 100 (e.g., stored within server 106) or is otherwise modeled mathematically or is superimposed on a model of a floor plan of the healthcare facility. Alternatively or additionally, the caregiver 114 is determined to be within zone 116 if the caregiver 114 is determined to be inside of a radius of a predetermined distance from the equipment locating tag 102 attached to patient support apparatus 110.

In some embodiments, it is server 155 that is configured with software which makes the determination regarding successful rounds based on information received from RTLS server 106, but in other embodiments, one of the other servers or computers 154, such as a workflow server, scheduling server, etc. is configured with the software that makes the determination regarding successful rounding based on caregiver location 114 relative to zone 116 as communicated by RTLS server 106. Accordingly, the present disclosure describes server 106 and server 155 as performing various calculations and functions to determine whether a successful round has occurred but the discussion is equally applicable to other computers, such as computers 150, 152, 154. That is, some functions described herein as being performed by server 106 or server 155 may, in some embodiments, be distributed among multiple computer devices 106, 150, 152, 154, 155.

In some embodiments, the rounding zone 116 around patient support apparatus 100 is defined as an area within about three feet of the patient support apparatus 110. That is zone 116 is modeled as an area three feet beyond a perimeter of a footprint of the patient bed. Zone 116, therefore, may be defined as a geometric footprint, such as a rectangle, as measured with respect to the equipment locating tag 102 that is attached to the patient support apparatus 110. Illustratively, the geometric footprint is a circle that is about six feet in radius from tag 102. Thus, zone 116 is defined as an area within about six feet of the equipment locating tag 102 mounted to the patient support apparatus 110. Assuming the equipment locating tag 102 attached to bed 110 is mounted along a centerline of bed 110, then zone 116 will extend about four feet beyond bed 110 in some areas assuming a width of bed 110 is about four feet (i.e., two feet on either side of the centerline).

It is known that some patient beds 110 are placed at particular locations within patient rooms. For example, a head wall unit or bed locator unit may be mounted to a wall in a patient room and the patient bed 110 may be placed with its head end centered on the head wall unit or bed locator unit. See, for example, U.S. Pat. No. 6,145,253 for examples of such head wall units and bed locator units. If patient bed 110 is expected to be situated at a particular location within a patient room, then in such embodiments, zone 116 may be defined around the patient support apparatus 110 according to a set of X and Y coordinates within the patient room as mapped within hub computer 150 or some other computer such as server 106.

In still other embodiments, zone 116 around the patient support apparatus 110 is defined as any area within the corresponding patient room that is beyond a threshold distance from a doorway of the first patient room. An illustrative doorway is shown to the left in FIG. 1 and a threshold distance may be defined about midway between the wall including the doorway and an oppositely facing wall of the patient room. By requiring the caregiver 114 to be situated within zone 116 adjacent to patient support apparatus 110 for a predetermined period of time, such as about 20 seconds to about 2 minutes just to give a couple arbitrary examples, the likelihood that the caregiver 114 will meaningfully interact with the patient 112 while making their rounds is enhanced.

In some embodiments, one of badges 102 may also be worn by patient 112. In such embodiments, zone 116 may be defined with respect to the badge 102 worn by the patient rather than with respect to the equipment locating tag 102 that is attached to patient support apparatus 110. That is, the caregiver 114 assigned to one or more patients 112 may be required to be in proximity with each of the patients 112 by a threshold distance in order for a successful caregiver round to be considered to have occurred. In such embodiments, therefore, successful rounds are able to occur outside of patient rooms such as if the patient 112 is in a treatment room, imaging room, operating room, or the like. Similarly, successful rounds are able to occur within the patient room even if the patient is not in bed 110, but is instead seated on a chair in the room, standing by a window of the room, located in a bathroom of the room, and so forth.

In connection with determining successful rounds, server 106 and/or server 155 further determines, based on tag ID data, whether the caregiver 114 located within zone 116 is among the caregivers assigned to care for the patient 112 that is assigned to the patient room. Of course, as noted above, server 106 also determines whether caregiver 114 is within zone 116 adjacent the patient support apparatus 110, or adjacent the patient as the case may be, for a predefined time period. In some embodiments, as noted above, rather than defining zone 116 with respect to the equipment locating tag 102 on bed 110, zone 116 is defined with respect to a patient locating tag 102 worn by, or otherwise carried by, the patient 112. As such, a determination of whether tags 102 of the assigned caregiver and patient are within a predefined distance (e.g., 3 to 5 feet) for a threshold period of time is made by server 106 and/or server 155 to determine a successful round.

In some embodiments, server 106 and/or server 155 receives patient data from the patient support apparatus 110 via a communication interface 202 of the patient support apparatus 110 as shown diagrammatically in FIG. 2. The patient data may indicate whether the patient 112 is currently supported on the patient support apparatus 110. It is contemplated by the present disclosure that the patient support apparatus 110 may determine a presence of the patient 112 on the patient support apparatus 110. For example, the patient support apparatus 110 may determine an amount of weight supported on the patient support apparatus using a scale system 224 integrated into the patient support apparatus 110. If the determined weight does not exceed a predefined weight, the patient support apparatus 110 determines the patient is not supported on the patient support apparatus 110. If, however, the determined weight exceeds the predefined weight, the patient support apparatus 110 determines that the patient 112 is supported on the patient support apparatus 110. This allows server 106 and/or server 155 to affirm that the assigned caregiver 114 is, in fact, attending to a patient 112 supported on a patient support apparatus 110 and not just an empty patient support apparatus 110. As such, server 106 and/or server 155 may further ensure that the caregiver round has been successfully completed only when the patient 112 is present on the patient support apparatus 110 as sensed by a sensor such as one or more load cells of the scale system 224.

In some embodiments, server 106 and/or server 155 and/or some other computer device 154 determines that a successful round has occurred only if the caregiver locating tag 102 of the caregiver 114 assigned to the patient 112 that is located in zone 116 for the threshold period time is also located in the zone 116 within a time range relative to a scheduled caregiver rounding time. For example, if the caregiver 114 is scheduled to make patient rounds for a given patient 112 every two hours, say 6:00 pm, 8:00 pm, 10:00 pm, etc., then the time range for successful rounding may be established to include some amount of time before and after the scheduled round time. To give an arbitrary example, the time range may include thirty minutes before the scheduled round time and fifteen minutes after the scheduled round time. Thus, in the hypothetical example, the time range for completing a successful round for the scheduled 6:00 pm round spans from 5:30 pm to 6:15 pm.

It is contemplated by the present disclosure that the time ranges before and after the scheduled round time for determining successful rounds are at the discretion of a programmer or system administrator of system 100 and may be any desired amounts of time before and after a scheduled round. By using such time ranges for determining successful rounds, caregivers 114 are prevented from successfully completing their rounds for a particular patient 112 too early or too late with regard to the rounding schedule. If a caregiver 114 assigned to a patient 112 does not complete a successful round within the time range or time window for successful rounding, then a missed round is logged in server 106 or server 155 or other computer device 154 for the assigned caregiver(s) 114.

In some embodiments, the time between which assigned caregivers 114 are determined to be within rounding zone 116 for the predetermined time periods are monitored. This permits server 106 and/or server 155 and/or some other computer device 154 to determine that a threshold amount of time has elapsed before a subsequent round after a successful round is also counted as a successful round. For example, if rounds are scheduled every two hours and the time range for successful rounding is established as one hour before and one hour after the scheduled round time, then assuming the 6:00 pm schedule round, a caregiver 114 could conceivably enter zone 116 at, say, 6:55 pm, stay in zone 116 until 7:00 pm, and then enter zone 116 again at say, 7:05 pm. Without the requirement of a minimum elapsed time between rounds being required, the scenario just described would result in a successful round for the 6:00 pm schedule round and a successful round for the 8:00 pm scheduled round even though the caregiver entered zone 116 only ten minutes apart. So, the minimum elapsed time required between successful rounds may be, for example, about 1 hour to about 1.5 hours if the rounds are scheduled every two hours. Of course, the minimum elapsed time is at the discretion of a programmer or system administrator of system 100 and may be set at different times for different scheduled round spacing (e.g., 3 hours apart, 4 hours apart, etc.).

Referring once again to FIG. 1, patient support apparatus 110 has a bed frame 124 which includes a base frame 126 with casters 128 and an upper frame or patient support platform 120. The patient support apparatus 110 further includes a headboard 130 at a head end 132, a footboard 134 at a foot end 136, and siderails 138 coupled to the patient support platform 120. A surface or mattress 122 is supported on the patient support platform 120 and, in some embodiments, includes a plurality of inflatable support bladders as is well known in the art. Mattress 122 has an upper surface 140 on which the patient 112 lies. Additionally, the patient support platform 120 includes a number of mattress support sections that support the mattress 122. The mattress support sections include a head section 212, a seat section 214, a thigh section 216, and a foot section 218 as shown diagrammatically in FIG. 2. The head section 212, the thigh section 216, and the foot section 218 are movable relative to the seat section 214 which, in some embodiments, is affixed to upper frame members of the patient support platform 120. For example, the head section 212 may be pivotably raised and lowered relative to the seat section 214, the thigh section 216 may be pivotably raised and lowered relative to the seat section 214, and the foot section 218 may be pivotably raised and lowered relative to the thigh section 216 and the seat section 214.

As shown diagrammatically in FIG. 2, the patient support apparatus 110 further includes a head motor or actuator 206 coupled to the head section 212 of the patient support apparatus 110, a thigh motor or actuator 208 coupled to the thigh section 214, and a foot motor or actuator 210 coupled to the foot section 218. Each of motors 206, 208, 210 may include, for example, an electric motor of a linear actuator. In the illustrative embodiment, a seat section 214 of the patient support apparatus 110 lacks a motor or actuator because it does not articulate relative to the frame members of platform 120. The head motor 260 is operable to raise and lower the head section 212 relative to seat section 214, the thigh motor 208 is operable to raise and lower the thigh section 216 relative to seat section 214, and the foot motor 210 is operable to raise and lower the foot section 218 relative to thigh section 216 and the seat section 214. In addition, the patient support apparatus 110 may include electronic medical record (EMR) charting capability that permits information or data to be charted into a patient's EMR automatically or via commands entered on the patient support apparatus 110. In some embodiments, server 106 and/or server 155 is used to chart information regarding caregiver handoffs of patients during caregiver shift changes into the patient's EMR, either automatically during or at the conclusion of a caregiver round, or in response to user inputs by a caregiver at server 106, at server 155, or at another computer 150, 152, 154.

As also shown diagrammatically in FIG. 2, the patient support apparatus 110 includes a pneumatic system 220 that controls inflation and deflation of the various air bladders of mattress 122. The pneumatic system 220 is represented in FIG. 2 as a single block but that block 220 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system 220 for inflating and deflating air bladders of mattresses of patient support apparatuses. It should be understood that the inflatable bladders are grouped into various zones of mattress 122. For example, head, seat, thigh and foot zones of mattress 122 each may have one or more bladders located above the respective sections 212, 214, 216, 218 of the same names, just to give one example of a mattress having a plurality of inflatable zones.

The illustrative patient support apparatus 110 includes one or more elevation system motors or actuators 222 to raise, lower, and tilt the patient support platform 120 relative to a base frame 126, which in some embodiments, comprise linear actuators with electric motors. Thus, actuators 222 are sometimes referred to herein as motors 222. The patient support apparatus 110 further includes scale system 224, as mentioned above, to determine a weight of the patient supported on the patient support apparatus 110.

The illustrative patient support apparatus 110 of FIG. 1 includes two user input devices: a caregiver input, which is referred to herein as a main input device 226, and a patient input device 228. The user input devices 226, 228 are electronically coupled to a controller 204 of patient support apparatus 110. For example, the controller 204 may include, among other components customarily included in such devices, a microprocessor 232 and a memory device 230. The memory device 232 may be, for example, a programmable read-only memory device ("PROM") including erasable PROM's (EPROM's or EEPROM's). In use, the memory device 230 is capable of storing, amongst other things, instructions in the form of, for example, a software routine (or routines) which, when executed by the microprocessor, allow the controller 204 to control operation of the features of the patient support apparatus 110.

The user input devices 226, 228 are capable of receiving inputs from a user (e.g., a patient, hospital staff, caregiver, etc.) and, in those embodiments, in which input devices 226, 228 are inputs on a graphical display, are also capable of providing output to the user related to various sensor and/or configuration data of the patient support apparatus 110. Sensor data may include various sensor readings related to current positions, levels, temperatures, pressure levels, etc. of various components of the patient support apparatus 110. In some embodiments, the configuration data may include a designated pressure level of each zone of the plurality of zones of the mattress 122, various settings for positioning the components of the patient support apparatus 110 (e.g., a designated angle of the head section 212 of the patient support apparatus 110 relative to the seat section 214 or relative to horizontal), notifications based on detected events corresponding to the sensor data, and/or any other configurable data that may be set by the user and managed by the controller 204.

Optionally, patient support apparatus 110 includes a proximity sensor 234 as shown diagrammatically in FIG. 2 (in dotted line). Proximity sensor 234 is configured to communicate with tags 102 worn by respective caregivers 114 or patients 112 when the caregivers or patients, as the case may be, are within a threshold distance of proximity sensor 234. Thus, in some embodiments, zone 116 is defined by the reception range between tags 102 and sensor 234. Data indicating that sensor 234 is in wireless communication with one or more tags 102 is among the bed data transmitted from communication interface 202 to one or more of servers 106, 154, 155 and/or computers 150, 152. In some embodiments, control circuitry 204 of the patient bed 110 includes UWB circuitry that is configured to process the wireless signals between proximity sensor 234 and any tags 102 in wireless communication with proximity sensor 234. In this regard, proximity sensor 234 and the UWB circuitry of patient bed 110 operate in a similar manner as transceivers 104 of the high-accuracy locating system.

Based on the foregoing, therefore, the present disclosure contemplates that caregiver rounding system 100 includes a bed 110 configured to support patient 112 thereon, equipment locating tag 102 coupled to the bed 110, and caregiver locating tag 102 coupled to the caregiver 114. The caregiver rounding system 100 also includes a plurality of receivers 104 that are mounted at fixed locations and that are in wireless communication with the equipment locating tag 102 and the caregiver locating tag 102. At least one computer, such as hubs 150 and/or server 106, are communicatively coupled to the plurality of receivers 104. The equipment locating tag 102, the caregiver locating tag 102, the plurality of receivers 104, and the at least one computer 106, 150 cooperate to form a high-accuracy locating system that is operable to determine a location of the equipment locating tag 102 and the caregiver locating tag 102 within at least one foot of an actual location of the equipment locating tag 102 and the caregiver locating tag 102, respectively. The at least one computer 106, 150, in some embodiments, model rounding zone 116 adjacent the bed 110 based on the location of the equipment locating tag 102. At least one computer 106, 150, 155 determines that the caregiver 114 has successfully completed a caregiver round if the caregiver locating tag 102 is located within the rounding zone 116 for a threshold period of time.

In some embodiments, the rounding zone 116 is defined as being within a boundary that is about three feet from a periphery of the bed 110. For example, the rounding zone 116 may be defined by a boundary calculated as being about three feet away from a footprint of the bed 110 as theoretically projected onto a floor supporting the bed 110. In the illustrative example, the rounding zone 116 is defined as being a circular boundary having a radius of about five feet and centered on the equipment locating tag 102 attached to bed 110. Optionally, the threshold period of time for determining a successful is about five minutes. However, the threshold period of time for determining a successful round may be greater than about one minute just to give another arbitrary example.

In the illustrative example of FIG. 1, the equipment locating tag 102 and the caregiver locating tag 102 communicate with the plurality of receivers 104 via ultra-wideband (UWB) signals. If desired, the locations of the equipment locating tag 102 and the caregiver locating tag 102 are determined by the at least one computer 106, 150 using two way ranging and time difference of arrival (TDOA) techniques. Alternatively or additionally, the locations of the equipment locating tag 102 and the caregiver locating tag 102 are determined by the at least one computer 106, 150 using time of arrival (TOA) at which transmissions from the equipment locating tag and the caregiver locating tag are received at the plurality of receivers, or by using time of flight (TOF) techniques. Further alternatively or additionally, the at least one computer 106, 150 uses signals from only a subset of the plurality of receivers 104 to determine the location of the equipment locating tag 102 and the caregiver locating tag 102. The subset may be determined based on signal strength of signals from the equipment locating tag 102 and the caregiver locating tag 102 to the plurality of receivers 104, for example. In some instances, the subset may include at least three receivers 104 from the plurality of receivers that have highest signal strength values as compared to others of the plurality of receivers 104.

In some embodiments, the bed 110 may include a sensor that senses a presence of the patient 112 on the bed 110 and the at least one computer 106, 150, 155 is configured to determine that a successful caregiver round has occurred only if the patient 112 is present on the bed 110 as sensed by the sensor. The illustrative bed 110 includes communication circuitry 202 that is configured to transmit patient presence data for receipt by the at least one computer 106, 150, 155. The sensor may include a weight sensor of a weigh scale system 224 of the bed 110, for example, or may include proximity sensor 234. In some embodiments, the caregiver rounding system 10 further include a patient locating tag 102 coupled to a patient. In some such embodiments, the at least one computer 106, 150, 155 is configured to determine that a successful caregiver round has occurred only if the patient locating tag 102 is determined to be within the rounding zone 116 with the caregiver locating tag 102 for the threshold period of time.

The present disclosure also contemplates that a notification is provided to caregiver 114 to indicate a successful round has occurred and/or to indicate that a successful round has not yet occurred for a particular patient 112. For example, an indicator such as one or more light emitting diodes (LED's) or a single multi-color LED of the caregiver locating tag 102, may be illuminated to indicate successful and/or unsuccessful caregiver rounding. For example, each time the caregiver 114 enters a patient room, the multi-color LED may be illuminated red or yellow to indicate that a successful round has not yet occurred. After the caregiver 114 meets the successful rounding criteria, as discussed above, then the multi-color LED is illuminated green. Upon exit of the patient room, the multi-color LED is no longer illuminated until the caregiver 114 enters the next patient room. Signals controlling the manner in which the multi-color LED is to be illuminated are communicated to the caregiver locating tag 102 from at least one computer device 106, 150, 152, 154, 155 of the high-accuracy locating system via one or more of the transceivers 104.

In some embodiments, a first LED is illuminated on the caregiver locating tag 102 to indicate that a successful round has not yet occurred and a second LED is illuminated on the caregiver locating tag 102 to indicate that a successful round has occurred. In some embodiments, the first LED is no longer illuminated when the second LED becomes illuminated. In other embodiments, the first LED remains illuminated when the second LED becomes illuminated. Both the first and second LED's may no longer be illuminated in response to the caregiver 114 leaving the room. Alternatively or additionally, one or more messages are displayed on a mobile device, such as a mobile phone, carried by the caregiver 114. For example, in response to the caregiver 114 entering a patient room, one of the computer devices 106, 150, 152, 154, 155 of system 100 initiates a message for display on the caregiver's mobile device indicating that a successful round has not yet occurred. Then, in response to at least one of the computer devices 106, 150, 152, 154, 155 of system 100 determining that a successful round has occurred, a message is sent to the caregiver's mobile device indicating that the round has been completed successfully. Alternatively or additionally, similar types of messages under similar circumstances are displayed on a graphical room station of a nurse call system or on some other computer device located in the patient room to provide a notification to the caregiver 114 regarding the status of caregiver rounding for the particular patient 112 in the patient room.

For additional details of a system configured to provide messages to the mobile devices of staff members, such as housekeepers 240, of a healthcare facility, see U.S. Patent Application Publication No. 2019/0108908 A1 which is hereby incorporated by reference herein in its entirety. For additional details of a nurse call system having graphical room stations, see U.S. Pat. Nos. 8,169,304 and 8,598,995, each of which is hereby incorporated by reference herein in its entirety. For additional details of the display of information relating to caregiver rounding, see U.S. Pat. No. 9,240,120 which is hereby incorporated by reference herein in its entirety. Nurse call server 155 of system 100 is configured to generate rounding reports of the type shown and described in U.S. Pat. No. 9,240,120 in some embodiments.

Figure 3:
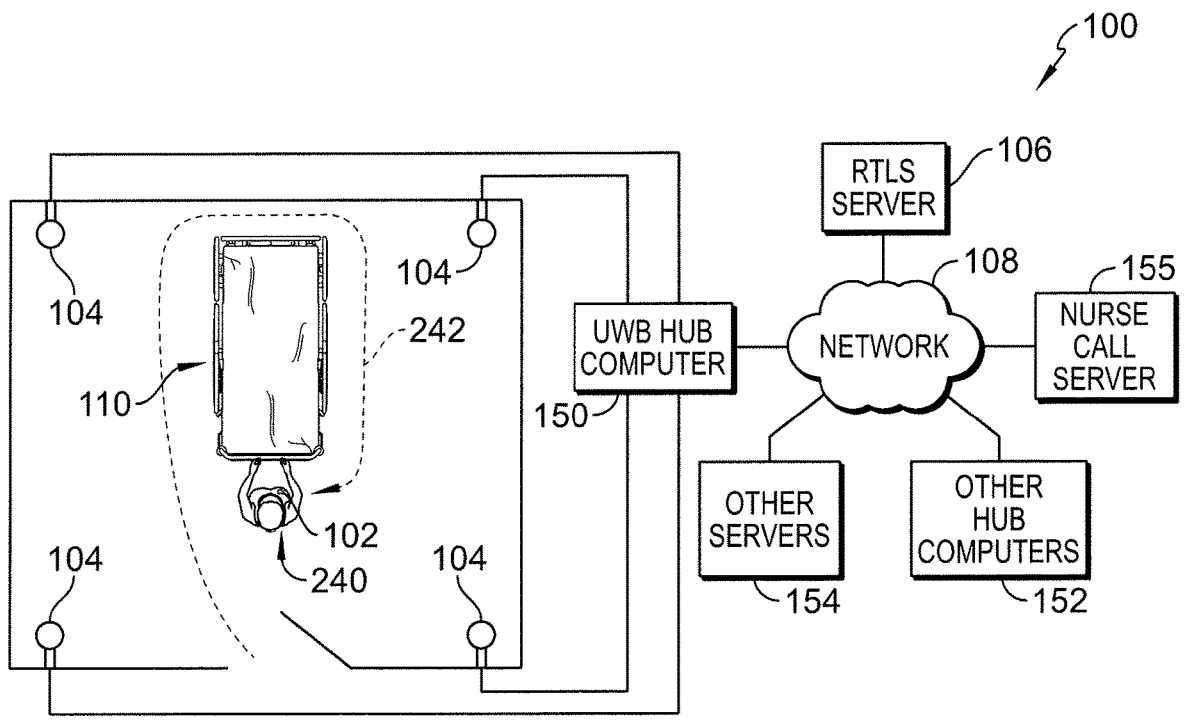
FIG. 3 is a diagrammatic top plan view showing a patient room having a bed therein and showing the high-accuracy RTLS monitoring movement of a housekeeper along a proper path (dotted line) that substantially circumnavigates the bed which is indicative that the housekeeper has properly cleaned the bed.
Figure 4:
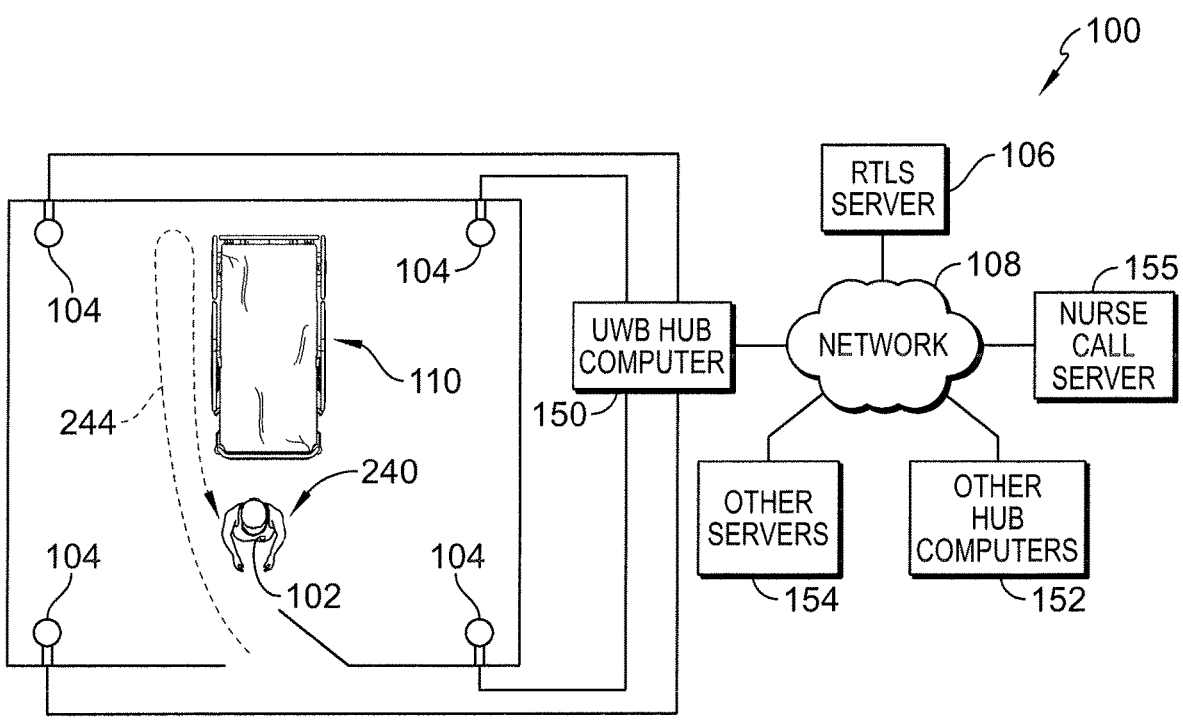
FIG. 4 is a diagrammatic top plan view, similar to FIG. 3, showing the high-accuracy RTLS monitoring movement of a housekeeper along an improper path (dotted line) that does not circumnavigate the bed which is indicative that the housekeeper has not properly cleaned the bed.

Referring now to FIGS. 3 and 4, a housekeeper 240 wearing a housekeeper locating tag 102 is present in a patient room with bed 110 which is to be cleaned by the housekeeper 240. System 100 is configured to monitor proper cleaning of bed 110 by the housekeeper 240. Components of system 100 of FIGS. 3 and 4 that are the same as like components of system 100 of FIGS. 1 and 2 described above are denoted with like reference numbers. However, this is not to imply that system 100 of FIGS. 3 and 4 for monitoring proper cleaning of bed 110 necessarily also has the rounding functionality discussed above in connection with FIGS. 1 and 2. In some embodiments, system 100 has only one of the described bed cleaning monitoring functionality or the described rounding monitoring functionality. In other embodiments, system 100 has both bed cleaning monitoring functionality and rounding monitoring functionality.

Housekeeper 240 wears or otherwise carries a housekeeper locating tag 102 and the high-accuracy locating system, including receivers 104, UWB hub computer 150, server 106 and, in some embodiments, other computers 154, 155, determines a path of movement of the housekeeper locating tag 102 relative to the bed 110 in the room. The movement of the housekeeper locating tag 102 is considered to correspond to the movement of the housekeeper 240. In FIG. 3, the housekeeper locating tag 102 is shown diagrammatically to have moved along a path 242 that substantially circumscribes bed 110 thereby indicating that the housekeeper has substantially circumnavigated bed 110. Thus, the movement of housekeeper 240 along path 242 around bed 110 is indicative that the housekeeper properly cleaned the bed. In FIG. 4, the housekeeper 240 is shown diagrammatically to have moved along a path 244 that only extends back and forth along one side of bed 110 which represents an example of improper movement of the housekeeper 240 during cleaning of bed 110.

As shown in FIG. 3, path 242 has portions adjacent the opposite sides, head end, and foot end of bed 110. However, path 242 does not completely surround bed 110 by forming a closed loop, for example. Thus, path 242 does not extend a full 360 degrees around bed 110 but this is not to say that the housekeeper 240 may not move a full 360 degrees or more around bed 110 while cleaning the bed 110. As such, housekeeper 240 is considered to have substantially circumnavigated bed 110 if the housekeeper locating tag 102 moves by about 270 degrees around bed 110, for example. Such movement includes, for example, the housekeeper 240 being located along opposite sides of bed 110 and along one or the other of the head end or foot end of bed 110. This accounts for the fact that the housekeeper is able to reach across the head end or foot end of bed 110 with one of their arms to clean (e.g., spray and/or wipe down) the head end or foot end of bed 110 while standing at one side of bed 110 or the other or both at different times.

One or more of computers 106, 150, 154, 155 may be configured to monitor for movement of housekeeper 240 around bed 110 by an amount greater than or less than about 270 degrees in other embodiments and such movement is still considered to represent proper cleaning of bed 110 due to the housekeeper 240 substantially circumnavigating the bed 110 as long as the amount of movement around bed 110 permits the housekeeper 240 to reach all portions of bed 110 that are to be cleaned. Also, to arrive at a determination that bed 110 has been properly cleaned by the housekeeper 240, the path 242 around bed 110 should be within a threshold distance, such as within 2 or 3 feet, of a perimeter of bed 110 to assure that the housekeeper is within arm's reach of the bed 110 during the cleaning process. Furthermore, in some embodiments, a minimum time threshold, such as about 2 to about 10 minutes, during which the housekeeper 240 is required to be located along path 242 is used to make the determination that the bed 110 has been properly cleaned. Such a minimum time threshold assures that the housekeeper does not move around bed 110 along path 242 too quickly for a proper cleaning of bed 110 to have occurred.

To determine whether the path 242 of housekeeper 240 around bed 110 meets the "proper cleaning" criteria, the high-accuracy locating system determines the location of the housekeeper locating tag 102 relative to an equipment location tag 102 carried by bed 110 in some embodiments. In other embodiments, one or more of the computer devices 106, 150, 152, 154, 155 of the high-accuracy locating system models an expected location of bed 110 within the room using X-Y coordinates as discussed above in connection with system 100 of FIGS. 1 and 2. In still other embodiments, a floor plan layout of the room with the bed 110 superimposed thereon may be modeled by one or more of the computer devices 106, 150, 152, 154, 155 and then the path 242 is compared to floor plan model.

The present disclosure also contemplates that a notification is provided to housekeeper 240 to indicate a proper cleaning and/or an improper cleaning of bed 110. For example, an indicator such as one or more light emitting diodes (LED's) or a single multi-color LED of the housekeeper locating tag 102, may be illuminated to indicate proper and/or improper cleaning of bed 110. For example, each time the housekeeper 240 enters a patient room, the multi-color LED may be illuminated red or yellow to indicate that the respective bed 110 has not yet been proper cleaned. After the housekeeper 240 substantially circumnavigates the bed 110 while meeting other proper cleaning criteria (e.g., time threshold, minimum distance from bed 110, etc.), if any, then the multi-color LED is illuminated green. Upon exit of the patient room, the multi-color LED is no longer illuminated until the housekeeper enters the next patient room. Signals controlling the manner in which the multi-color LED is to be illuminated are communicated to the housekeeper locating tag 102 from at least one computer device 106, 150, 152, 154, 155 of the high-accuracy locating system via one or more of the transceivers 104.

In some embodiments, a first LED is illuminated on the housekeeper locating tag 102 to indicate that the bed 110 has not yet been properly cleaned and a second LED is illuminated on the housekeeper locating tag 102 to indicate that the bed 110 has been properly cleaned. In some embodiments, the first LED is no longer illuminated when the second LED becomes illuminated. In other embodiments, the first LED remains illuminated when the second LED becomes illuminated. Both the first and second LED's may no longer be illuminated in response to the housekeeper 240 leaving the room.

Alternatively or additionally, one or more messages are displayed on a mobile device, such as a mobile phone, carried by the housekeeper 240. For example, in response to the housekeeper 240 entering a patient room, one of the computer devices 106, 150, 152, 154, 155 of system 100 initiates a message for display on the housekeeper's mobile device indicating that the bed 110 has not yet been properly cleaned. Then, in response to at least one of the computer devices 106, 150, 152, 154, 155 of system 100 determining that bed 110 has been properly cleaned, a message is sent to the housekeeper's mobile device indicating that the bed 110 has been successfully cleaned. Alternatively or additionally, similar types of messages under similar circumstances are displayed on a graphical room station of a nurse call system or on some other computer device located in the patient room to provide a notification to the housekeeper 240 regarding the status of properly cleaning bed 110. A notification to a supervisor, such as to a supervisor's mobile device, is initiated by server 106 or server 155 in some embodiments if the housekeeper 240 exits the patient room without having properly cleaned the respective bed 110.

For additional details of a system configured to provide messages to the mobile devices of staff members, such as housekeepers 240, of a healthcare facility, see U.S. Patent Application Publication No. 2019/0108908 A1 which is already incorporated by reference herein. For additional details of a nurse call system having graphical room stations, see U.S. Pat. Nos. 8,169,304 and 8,598,995, each of which is already incorporated by reference herein.

Based on the foregoing, the present disclosure contemplates that system 100 is configured for monitoring proper cleaning of patient bed 110 by housekeeper 240. The system 100 includes housekeeper locating tag 102 that is transported by the housekeeper 240, a plurality of receivers 104 that are mounted at fixed locations and that are in wireless communication with the housekeeper locating tag 102, and at least one computer 106, 150, 154, 155 communicatively coupled to the plurality of receivers 104. The housekeeper locating tag 102, the plurality of receivers 104, and the at least one computer 106, 150, 154, 155 cooperate to form a high-accuracy locating system that is operable to determine a location of the housekeeper locating tag 102 within at least one foot of an actual location of the housekeeper locating tag 102. In some embodiments, the at least one computer 106, 150, 154, 155 models a patient bed position of the patient bed 110 in the respective patient room. The at least one computer 106, 150, 154, 155 determines that the housekeeper 240 has properly cleaned the patient bed 110 if the housekeeper locating tag 120 is determined to have substantially circumnavigated the patient bed position.

In some embodiments, the at least one computer 106, 150, 154, 155 models the patient bed position as being a set of coordinates at which the patient bed 110 is expected to occupy in the patient room. Optionally, the system 100 further includes equipment locating tag 102 that is coupled to the patient bed 110 and that is in communication with the plurality of receivers 104. In such situations, the at least one computer 106, 150, 154, 155 models the patient bed position as being within a boundary around the equipment locating tag 102. For example, the boundary may be defined as a circle having a radius of about two feet. Alternatively, the boundary may be defined as a rectangle having dimensions commensurate in size with a periphery of the hospital bed 110.

If desired, the at least one computer 106, 150, 154, 155 models the patient bed position as being a location of the equipment locating tag 102 and the at least one computer 106, 150, 154, 155 determines that the housekeeper 240 has properly cleaned the bed 110 if the housekeeper locating tag 102 is determined to have substantially circumnavigated the equipment locating tag 102. It is contemplated by this disclosure that, in some embodiments, the housekeeper locating tag 102 is considered to have substantially circumnavigated the equipment locating tag 102 if the housekeeper locating tag 102 has traveled at least 270 degrees around the equipment locating tag 102. It is also contemplated by this disclosure that, in some embodiments, the housekeeper locating tag 102 is considered to have substantially circumnavigated the patient bed position if the housekeeper locating tag 102 has traveled at least 270 degrees around the patient bed position as modeled in the at least one computer 106, 150, 154, 155.

In some embodiments, the patient bed 110 and a model of the patient bed position includes a head end, a foot end, a first side and a second side. In such embodiments, the housekeeper locating tag 102 is considered to have substantially circumnavigated the patient bed position if the housekeeper locating tag 102 has been determined by the at least one computer 106, 150, 154, 155 to have been next to each of the head end, foot end, first side, and second side. Optionally, the at least one computer 106, 150, 154, 155 tracks an amount of time that the housekeeper locating tag 102 spends circumnavigating the patient bed position and the at least one computer 106, 150, 154, 155 determines that the housekeeper 240 has properly cleaned the patient bed only if the housekeeper locating tag 102 is determined to have spent more than a minimum amount of time circumnavigating the patient bed position. Further optionally, the at least one computer 106 150, 154, 155 initiates a notification to a supervisor if the housekeeper 240 is determined by the at least one computer 106, 150, 154, 155 not to have properly cleaned the patient bed.

If the illustrative example, the housekeeper locating tag 102 communicates with the plurality of receivers via ultrawideband (UWB) signals. The location of the housekeeper locating tag 102 is determined by the at least one computer 106, 150, 154, 155 using two way ranging and time difference of arrival (TDOA) techniques. Alternatively or additionally, the location of the housekeeper locating tag 102 is determined by the at least one computer using time of arrival (TOA) at which transmissions from the housekeeper locating tag are received at the plurality of receivers, or by using time of flight (TOF) techniques.

In some embodiments of system 100 of FIGS. 3 and 4, the at least one computer 106, 150, 154, 155 uses signals from only a subset of the plurality of receivers 104 to determine the location of the housekeeper locating tag 102. The subset may be determined based on signal strength of signals from the housekeeper locating tag 102 to the plurality of receivers 104. The subset may include at least three receivers 104 from the plurality of receivers 104 having highest signal strength values as compared to others of the plurality of receivers 104, for example. Optionally, the at least one computer 106, 150, 154, 155 determines that the housekeeper 240 has properly cleaned the patient bed 110 only if the housekeeper locating tag 102 is determined to have remained in proximity of the patient bed position within a threshold distance while circumnavigating the patient bed position. For example, the threshold distance may be about three feet in some embodiments of system 100 of FIGS. 3 and 4.

Figure 5:
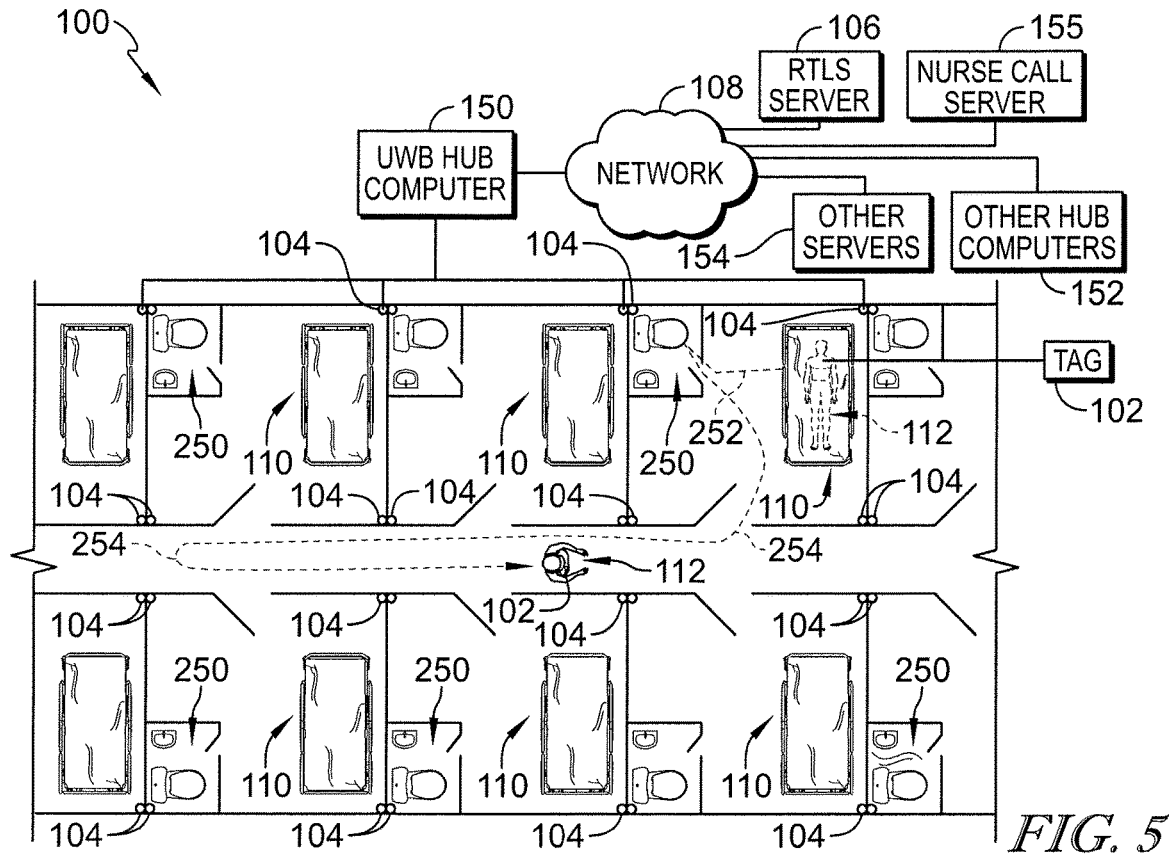
FIG. 5 a diagrammatic top plan view showing a number of patient rooms each having a bed therein and showing the high-accuracy RTLS monitoring how far a patient has ambulated along a path (dotted line) from the bed in the patient's assigned room to a bathroom and then from the bathroom down a hallway adjacent the patient's assigned room and partially back toward the patient's assigned room.

Referring now to FIG. 5, system 100 is configured to determine how far the patient 112 has ambulated within the healthcare facility. Thus, in the FIG. 5 embodiment, system 100 include a patient locating tag 102 coupled to the patient 112. It should be appreciated that system 100 is able to monitor the distances ambulated by multiple patients 112 but that only one patient is shown in FIG. 5 for discussion purposes. Components of system 100 of FIG. 5 that are the same as like components of system 100 of FIGS. 1-4 described above are denoted with like reference numbers. However, this is not to imply that system 100 of FIG. 5 for determining how far one or more patients 112 have ambulated necessarily also has the rounding functionality discussed above in connection with FIGS. 1 and 2 or the proper bed cleaning monitoring functionality discussed above in connection with FIGS. 3 and 4. In some embodiments, system 100 of FIG. 5 has only the patient ambulation distance monitoring functionality and in other embodiments, system 100 of FIG. 5 has either or both of the rounding functionality and/or bed cleaning monitoring functionality.

System 100 of FIG. 5 includes the plurality of receivers 104 that are mounted at fixed locations and that are in wireless communication with the patient locating tag 112. At least one computer 106, 150, 152, 154, 155 is communicatively coupled to the plurality of receivers 104. The patient locating tag 102, the plurality of receivers 104, and the at least one computer 106, 150, 152, 154, 155 of system 100 of FIG. 5 cooperate to form a high-accuracy locating system that is operable to determine a location of the patient locating tag 102 within at least one foot of an actual location of the patient locating tag 102. The at least one computer 106, 150, 152, 154, 155 of system 100 of FIG. 5 is configured to calculate a total distance that the patient 112 has ambulated based on movement of the patient locating tag 102 within the healthcare facility over a threshold period of time.

In some embodiments, system 100 of FIG. 5 further includes a plurality of equipment locating tags 102 that are attached to mobile patient support apparatuses such as stretchers, beds 110, wheelchairs, mobile patient lifts, and any other equipment capable of transporting patients from one location to another in a healthcare facility. In such embodiments, the at least one computer 106, 150, 152, 154, 155 omits from the total distance of patient ambulation any movement of the patient locating tag 102 that is also accompanied by a substantially concurrent movement of at least one of the plurality of equipment locating tags 102 that are within a threshold distance of the patient locating tag 102 based on an assumption that the patient 112 is possibly being transported on the respective patient support apparatus rather than ambulating. The threshold distance between the patient locating tag 102 and the equipment location tag 102 is about five feet or less in some embodiments.

The total distance of patient ambulation includes movement of the patient locating tag 102 within a patient room assigned to the patient, or any room for that matter, and movement of the patient locating tag 102 outside the patient room. For example, movement of the patient locating tag 102 within the patient room may include movement of the patient locating tag between the patient bed 110 in the patient room and a bathroom 250 included in the patient room as indicated by diagrammatic dotted line 252. Still further, movement of the patient locating tag 102 outside the patient room may include movement of the patient locating tag in a hallway adjacent to the patient room as indicated by the dotted line 254. In the depicted example, the patient 112 has traveled up and down a hallway after exiting the patient room as indicated diagrammatically by the portion of dotted line segment 254 outside of the patient room. Dotted line segments 252, 254 together show an overall path (collectively referred to as just path 254) of patient ambulation in the illustrative example.

As the patient 112 moves along the path 254, the at least one computer 106, 150, 152, 154, 155 tabulates a running total of the patient's distance traveled. Physicians or therapists, for example, sometimes prescribe or recommend that patients 112 ambulate (i.e., walk) a minimum distance each day during their recovery. Thus, system 100 of FIG. 5 monitors the patient ambulation distance for such patients 112 and compares the overall distance traveled along path 254 to the prescribed or recommended distance. In some instances, the physicians or therapists prescribe or recommend that the minimum distance of patient ambulation occur within a threshold period of time. For example, the threshold period of time in this regard may be about four hours, about eight hours, or more. Thus, the threshold period of time for patient ambulation may correspond to a shift during which caregivers 114 of the healthcare facility work. It is also within the scope of this disclosure for the threshold period of time for patient ambulation to be less than about four hours.

In some embodiments, the at least one computer 106, 150, 152, 154, 155 of system 100 of FIG. 5 records the total distance traveled along path 254 in memory after the threshold period of time has elapsed. It is contemplated by the present disclosure that, after the threshold period of time has elapsed, the at least one computer 106, 150, 152, 154, 155 transmits the total distance to an electronic medical records (EMR) computer for storage in the patient's electronic medical record. Furthermore, in some embodiments, the at least one computer 106, 150, 152, 154, 155 compares the total distance ambulated by the patient 112 to a predetermined distance, such as the prescribed or recommended distance, after the threshold period of time has elapsed and to determine whether or not the total distance exceeds the predetermined distance. The at least one computer may then report a result of the comparison to one or more caregivers 114. Alternatively or additionally, the at least one computer 106, 150, 152, 154, 155 reports the result of the comparison to nurse call server 155, assuming nurse call server 155 was not the computer that made the initial comparison. The distance ambulated by one or more patients 112 may be displayed on any one or more of a caregiver's mobile device, a display of nurse call computer 155, a status board of a nurse call system, a graphical room station, a display screen of computers 106, 152, etc., at the discretion of the system designer.

Similar to tags 102 of system 100 of FIGS. 1-4, the patient locating tag 102 of system 100 of FIG. 5 communicates with the plurality of receivers 104 via ultra-wideband (UWB) signals in some embodiments. Thus, the location of the patient locating tag 102 of system 100 of FIG. 5 may be determined by the at least one computer 106, 150, 152, 154, 155 using two way ranging and time difference of arrival (TDOA) techniques. Alternatively or additionally the location of the patient locating tag 102 of system 100 of FIG. 5 may be determined by the at least one computer 106, 150, 152, 154, 155 using time of arrival (TOA) at which transmissions from the patient locating tag are received at the plurality of receivers, or using time of flight (TOF) techniques. It is contemplated that the at least one computer 106, 150, 152, 154, 155 of system 100 of FIG. 5 may use signals from only a subset of the plurality of receivers 104 to determine the location of the patient locating tag 102 and the subset may be determined based on signal strength of signals from the patient locating tag 102 to the plurality of receivers 104. For example, the subset may include at least three receivers 104 from the plurality of receivers 104 having highest signal strength values as compared to others of the plurality of receivers 104.

Figure 6:
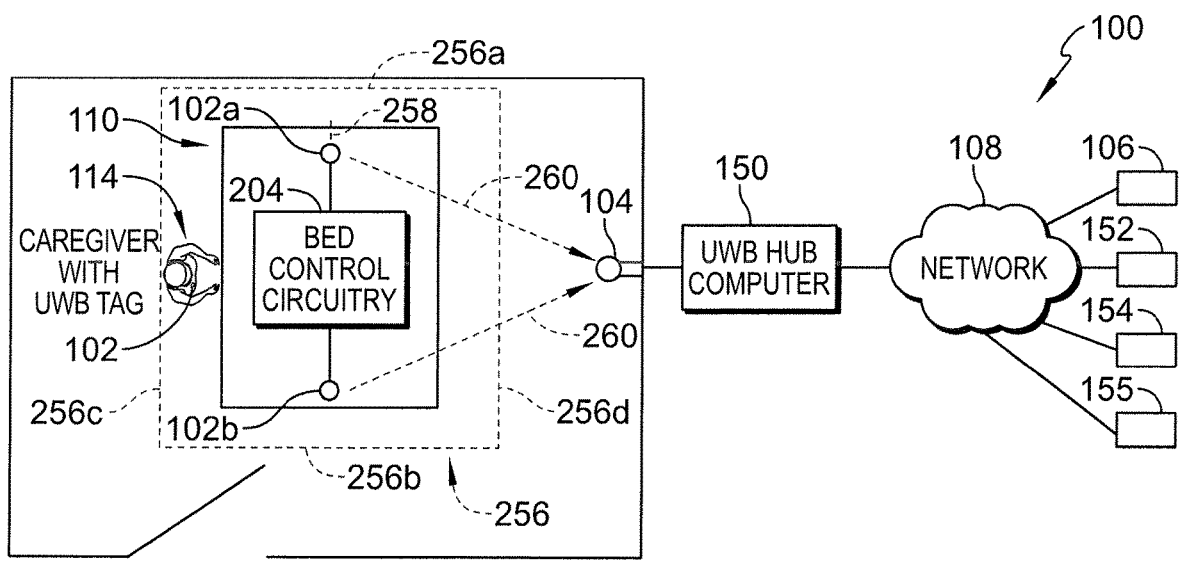
FIG. 6 is a diagrammatic top plan view showing a patient room having a bed therein and showing the bed having first and second transceivers coupled thereto for use, in cooperation with the high-accuracy RTLS, in determining a location of a caregiver locating tag in the room.

Referring now to FIG. 6, system 100 is configured to locate the caregiver 114 in a patient room and to determine whether the caregiver 114 is inside or outside a boundary 256 that is modeled around the bed 110. Bed 110 of system of 100 of FIG. 6 includes bed control circuitry 204, a first transceiver 102a that is carried by the patient bed 110 and that is coupled to the circuitry 204, and a second transceiver 102b that is carried by the patient bed 110 and that is coupled to the circuitry 204. The transceivers 102a, 102b are embodied as equipment locating tags in some embodiments. Caregiver locating tag 102 is transported by the caregiver 114 in the patient room. The caregiver locating tag 102 communicates a tag identification (ID) to the circuitry 204 via the first and second transceivers 102a, 102b in some embodiments. The circuitry 204 of bed 110 then uses one or more of two way ranging techniques, time difference of arrival (TDOA) techniques, time of arrival (TOA) techniques, or time of flight (TOF) techniques to determine a location of the caregiver locating tag 102 in the patient room relative to boundary 256.

In some embodiments of system 100 of FIG. 6, the first transceiver 102a is situated adjacent the head end of the patient bed 110 and the second transceiver 102b is situated adjacent the foot end of the patient bed. In the illustrative example, the first and second transceivers 102a, 102b are situated along a longitudinal centerline 258 of the patient bed 110. Thus, at least one computer 106, 150, 152, 154, 155 of system 100 is able to determination an orientation of bed 110 in the patient room by determining the locations of transceivers 102a, 102b based on signals from or between transceivers 102a, 102b of bed 110 and transceivers 104 of system 100. For example, the at least one computer 106, 150, 152, 154, 155 is able to model centerline or central axis 258 of bed 110 after determining the locations of transceivers 102a, 102b.

Once the locations of transceivers 102a, 102b are known and axis 258 modeled, the at least one computer 106, 150, 152, 154, 155 of system 100 is also able to implement a geofencing algorithm to establish the boundary 256 around bed 110. For example, segments 256a, 256b of boundary 256 are modeled as lines that are perpendicular to axis 258 and spaced a first distance, such as about 3 to about 5 feet, from the respective transceiver 102a, 102b and beyond the head and foot ends of bed 110. In a like manner, segments 256c, 256d of boundary 256 are modeled as lines that are parallel with axis 258 and spaced a second distance, such as about 3 to about 6 feet from transceivers 102a, 102b and beyond opposite sides of the bed 110. Thus, in the illustrative embodiment, boundary 256 is modeled as a quadrilateral such as a rectangle or square. In other embodiments, boundary 256 has a geometric shape other than quadrilateral. For example, boundaries formed by intersecting circles centered on transceivers 102a, 102b and having radii of about 4 to about 8 feet are also contemplated by the present disclosure.

Regardless of the shape of the boundary 256 around bed 110, the present disclosure contemplates that the circuitry 204 of the patient bed 110 models a caregiver control zone (e.g., the area within boundary 256) around the patient bed 110. Thus, if the circuitry 204 determines that the caregiver locating tag 102 is within the caregiver control zone, as shown in FIG. 6, the bed circuitry 204 then determines which functions of the patient bed 110 the caregiver 114 has permission to modify. For example, silencing bed alarms is among the functions of the patient bed 110 that some caregivers 114 may have permission to modify when located within the caregiver control zone defined within boundary 256. Alternatively or additionally, activating at least one therapy function is among the functions of the patient bed 110 some caregivers 114 may have permission to modify when located within the caregiver control zone defined by boundary 256. Further alternatively or additionally, activating movement of one or more portions of the bed frame of the patient bed 110 is among the functions that some caregivers 114 may have permission to modify when within the caregiver control zone. Thus, depending upon the type or role of the caregiver 114 within the caregiver control zone defined by boundary 256, different permissions for bed modification are established by the circuitry 204 of bed 110.

In some embodiments, system 100 of FIG. 6 is configured so that a server or computer remote from the patient bed 110, such as at least one of computers 106, 150, 152, 154, 155, communicates one or more messages to the patient bed 110 regarding the bed modification permissions that are granted to the caregiver 114 that is determined to be within the caregiver control zone. Such bed modification permission messages to bed 110 from at least one computer 106, 150, 152, 154, 155 may be in addition to, or in lieu, of the bed modification permission determinations made by circuitry 204 of bed 110. In either case, the at least one computer 106, 150, 152, 154, 155 and bed circuitry 204 are in communication such that at least one computer 106, 150, 152, 154, 155 communicates the functions of the patient bed 110 that the caregiver 114 has permission to modify in response to receipt of information from the bed circuitry 204 by the at least one computer 106, 150, 152, 154, 155 regarding the tag ID of the caregiver locating tag 102 that is located within the caregiver control zone surrounded by boundary 256.

In the illustrative example of FIG. 6, system 100 further includes a third transceiver 104 that is mounted in the patient room and the hub computer 150 is in communication with the third transceiver 104. The third transceiver 104 is in communication with the first and second transceivers 102a, 102b carried by the patient bed 110 as indicated by diagrammatic dotted line arrows 260. Thus, in some embodiments, the hub computer 150 determine a location and orientation of the patient bed 110 in the patient room based on transmissions 260 from the first and second transceivers 102a, 102b to the third transceiver 104. The present disclosure contemplates that the hub computer uses one or more of two way ranging techniques, time difference of arrival (TDOA) techniques, time of arrival (TOA) techniques, or time of flight (TOF) techniques to determine the location and orientation of the patient bed 110 in the patient room. In other embodiments, multiple transceivers 104 mounted in the patient room and/or adjacent patient rooms are in wireless communication with transceivers 102a, 102b of patient bed 110.

In some embodiments, system 100 of FIG. 6, the hub computer 150 communicates information pertaining to the location and orientation of the patient bed 110 to one or more of servers 106, 152, 154, 155. It is also contemplated by the present disclosure that, in some embodiments, the hub computer 150 and circuitry 204 of the patient bed 110 cooperate to determine the location of the caregiver 114 in the patient room based on communications that are received from the caregiver locating tag 102 by the first, second, and third transceivers 102a, 102b, 104. In the illustrative example of FIG. 6, the third transceiver 104 communicates with the first and second transceivers 102a, 102b of bed 110 using ultra-wideband (UWB) signals. Also in the illustrative FIG. 6 example, the caregiver locating tag 102 communicates with one or more of the first, second, and third transceivers 102a, 102b, 104 using ultra-wideband (UWB) signals.

Beds 110 of any of the embodiments disclosed herein in connection with FIGS. 1-5 and 7-13 may include first and second transceivers 102a, 102b as discussed herein in connection with the various FIG. 6 embodiments. Furthermore, systems 100 in which beds 110 have only one equipment locating tag 102 that is used for establishing a boundary, such as boundary 116 shown in FIG. 1, also may have the bed modification permission functionality discussed herein in connection with the various FIG. 6 embodiments.

Figure 7:
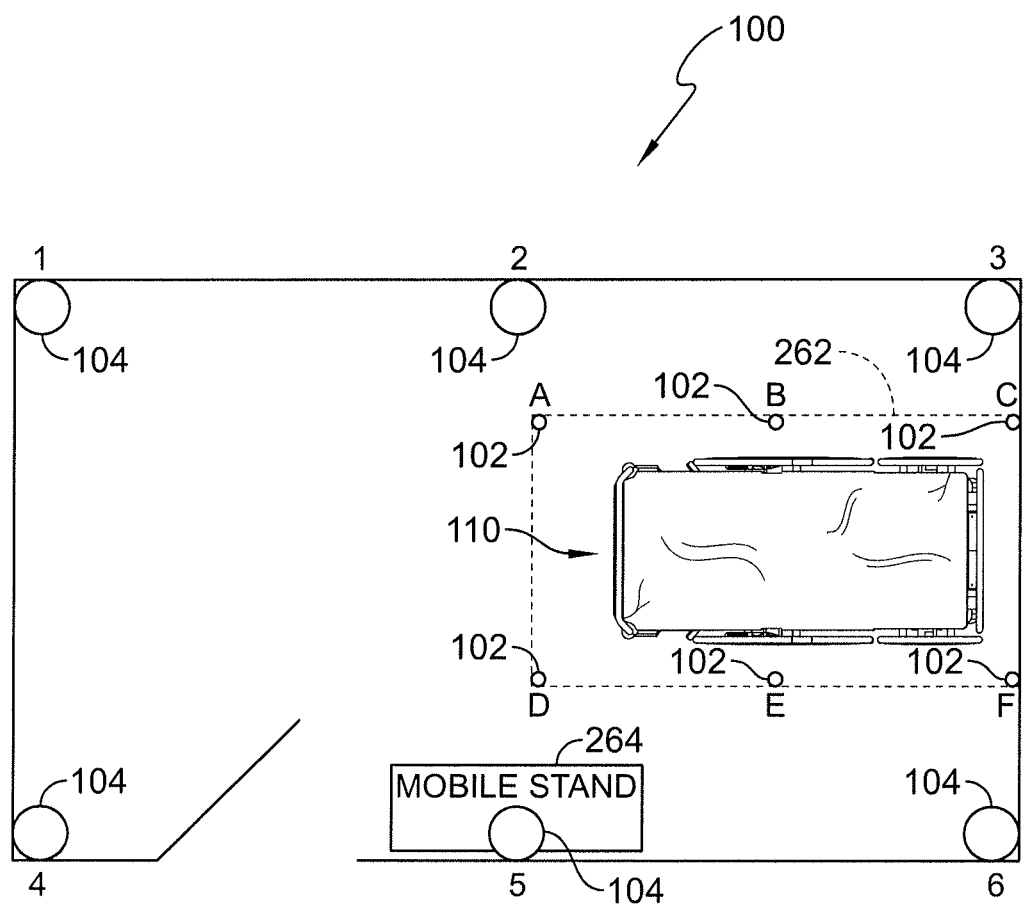
FIG. 7 is a diagrammatic top plan view showing a patient room having possible mounting locations for UWB locating receivers or transceivers labeled with numbers 1-6 and showing locations, labeled with letters A-G, at which a locating tag is placed along a boundary (dotted line) of an area of interest for evaluating signal quality values between locations 1-6 and A-G so that optimum mounting locations for a number of UWB locating receivers or transceivers less than 6 can be determined.

Referring now to FIG. 7, a patient room has patient bed 110 therein and is shown with a diagrammatic boundary 262 in dotted line around bed 110 to denote an area of interest. In the discussion that follows, transceivers or receivers 104 are referred to as locating system anchors 104 or locating anchors 104 or just anchors 104. When designing system 100 for a healthcare facility, it will be appreciated that the more locating anchors 104 that are used in the system 100, the more accurately the locations of mobile tabs 102 can be determined. However, the cost of the overall system 100 increases with the number of increasing anchors 104 that are used. Thus, cost and locating accuracy are competing design concerns of system 100.

Assuming that patient rooms, or any room for that matter, are only to have a limited number of anchors 104 per room, such as one, two or three anchors 104 per room, it is desirable for the limited number of anchors 104 to be mounted at locations that result in the optimum signal quality between the anchors 104 and mobile tags 102 that are within the area of interest defined by boundary 262, for example. Patient rooms and other rooms in healthcare facilities oftentimes have medical equipment that attenuates, blocks, or otherwise interferes with wireless communication between tags 102 and anchors 104. Thus, even in rooms of similar geometric floor plans, the optimum locations for mounting anchors 104 may vary from room to room depending upon the type and placement of equipment in the room.

With the foregoing in mind, and with continued reference to FIG. 7, the present disclosure contemplates a method for determining optimum mounting locations for anchors 104 in patient rooms. In the FIG. 7 example, there are six possible mounting locations for anchors 104 that are shown. These possible mounting locations for anchors 104 are labeled with numbers 1-6. For each possible mounting location 1-6, a locating tag 102 is moved to different locations along boundary 262. These six mobile tag locations along boundary 262 are labeled with letters A-F in FIG. 7. In other embodiments, there are more or less than six possible mounting locations for anchors 104 in the room and tag 102 is moved to more or less than six locations along boundary 262.

According to the contemplated method for determining optimum mounting locations for anchors 104, a test anchor 104 is placed temporarily at each of locations 1-6. While the test anchor is stationary at each respective location 1-6, the mobile tag 102 is placed at each location A-F along boundary 262 and measurements of signal quality values are taken by a computer that is transported with, and electrically coupled to, the test anchor 104. After the signal quality values are measured for each location 1-6 of the test anchor 104 and each location A-F of mobile tag 102 along boundary 262, a mathematical analysis is performed to determine the optimum location or locations for anchors 104 in the particular room under test. In some embodiments, the signal quality values correspond to signal strength values and the mathematical analysis includes an error sum of squares operation. As is apparent in FIG. 7, the area of interest as defined within boundary 262 is smaller than a floorplan of the entire patient room.

Based on the foregoing, therefore, the method for determining optimum placement of anchors 104 in the patient room includes determining a first number, N, of possible mounting locations for locating system anchors 104 on a wall or ceiling of the patient room. In some embodiments, N may is at least three. The method includes successively placing a locating system anchor 104 at each of the first number, N, of possible mounting locations and then, successively placing the portable locating tag 104 at a second number, M, of locations along the boundary 262. For example, M may is at least two.

Still further, the method of determining optimum placement of anchors 104 in the patient room includes transmitting a signal from the portable locating tag 102 to the locating system anchor 104 for each location N of anchor 104 and each location M of tag 102, thereby determining N×M signal quality values, V, using a computer coupled to the locating system anchor 104. Each signal quality value, V, corresponds to a respective individual combination of possible mounting locations 1-6 for the locating system anchor 104 and the particular second location A-F along the boundary 162 of tag 102. The method also includes performing an error sum of squares operation with the computer to optimize first and second mounting locations from among the N possible mounting locations for at least first and second locating system anchors 104 based on the signal quality values, V.

In the illustrative embodiment, the boundary 262 of the area of interest around patient bed 110 is shaped as a rectangle around the patient bed 100. Among the number, M, of six locations for placement of tag 102 along the boundary 262, four of the M locations correspond to corners of the rectangle. Illustratively, fourth and fifth locations of the M locations correspond to midpoints of the long sides of the rectangle. In some embodiments, the long sides and at least one short side of the rectangle is spaced at least two feet from an outer periphery of the patient bed 110.

In some embodiments, performing an error sum of squares operation with the computer coupled to the test anchor 104 to optimize mounting locations from among the N possible mounting locations for anchors 104 includes performing an error sum of squares operation with the computer to optimize first, second, and third mounting locations from among the N possible mounting locations for at least first, second, and third locating system anchors 104. In some instances, the signal quality values, V, include signal strength. Successively placing the test anchor 104 at each of the first number, N, of possible mounting locations includes mounting the locating anchor to a wheeled or mobile stand 264 and moving the mobile stand 264 successively so that the locating system anchor may be held by the wheeled stand 264 at each of the first number, N, of possible mounting locations. It is contemplated by the present disclosure that, transmitting the signal from the portable locating tag 102 to the locating system anchor 104 includes transmitting an ultra-wideband (UWB) signal.

The wheeled stand 264 includes, for example, a wheeled base and a vertically oriented telescopic pole assembly extending upwardly from the wheeled base. The telescopic pole assembly includes a lower pole fixed to the wheeled base and extending upwardly therefrom and an upper pole that vertically extends and retracts relative to the lower pole. The test anchor 104 is attached to an upper end region of the upper pole. The computer coupled to the test anchor 104 may be supported on a shelf that is mounted to the lower pole. When the mobile stand 264 is moved between locations 1-6 in the room, the upper pole may be retracted. After the mobile stand 264 is situated beneath the particular location 1-6 of interest, the upper pole is extended upwardly until the test anchor 104 is at the desired mounting height. The signal quality readings are then taken while the upper pole is extended. It should be appreciated that the method for determining placement of anchors 104, as shown diagrammatically in FIG. 7, can be used in connection with the various embodiments of system 100 shown and described in connection with any of FIGS. 1-6 and 8-13.

Figure 8:
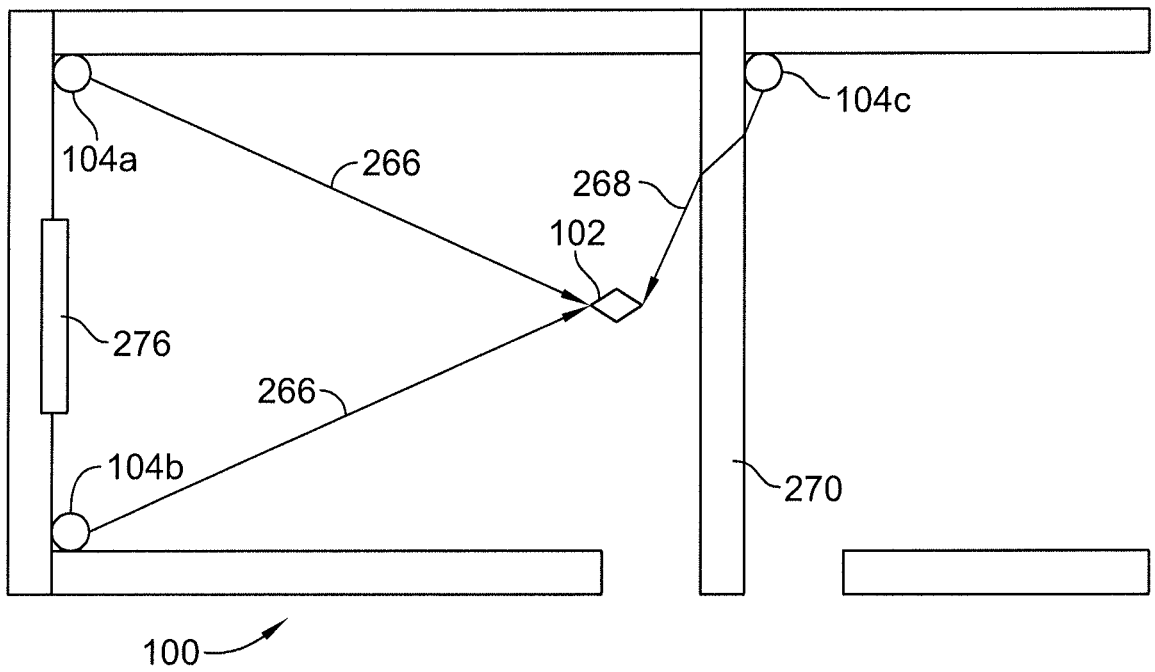
FIG. 8 is diagrammatic top plan view showing a mobile locating tag (diamond shaped) in a first room in communication with three UWB receivers or transceivers (circle shaped), one of which is located in a second room adjacent the first room, such that a wall between the first and second rooms refracts the signal between the mobile tag and the UWB receiver or transceiver in the second room.

Referring now to FIG. 8, mobile locating tag 102 is in communication with first and second locating system anchors 104a, 104b in a first patient room as indicated by diagrammatic arrows 266 and with a third locating system anchor 104c in a second patient room as indicated by diagrammatic arrow 268. A room wall 270 separates the first and second rooms. In UWB systems, like some embodiments of system 100 described herein, that use time of flight (TOF) or time difference of arrival (TDOA) with two way ranging, it is beneficial to have line-of-sight (LOS) between the mobile locating tag 102 and the anchors 104 being used to pinpoint the location of tag 102. Non-line-of-sight (NLOS) situations introduce errors in the two way ranging, due to the wireless UWB signal passing through objects, such as wall 270. Thus, in the FIG. 7 example, arrows 266 represent LOS signals between tag 102 and anchors 104a, 104b and arrow 268 represents an NLOS single between tag 102 and anchor 104c. The refraction of wireless signal 268 through wall 270 introduces an error in the distance calculated between anchor 104c and tag 102.

Figure 9:
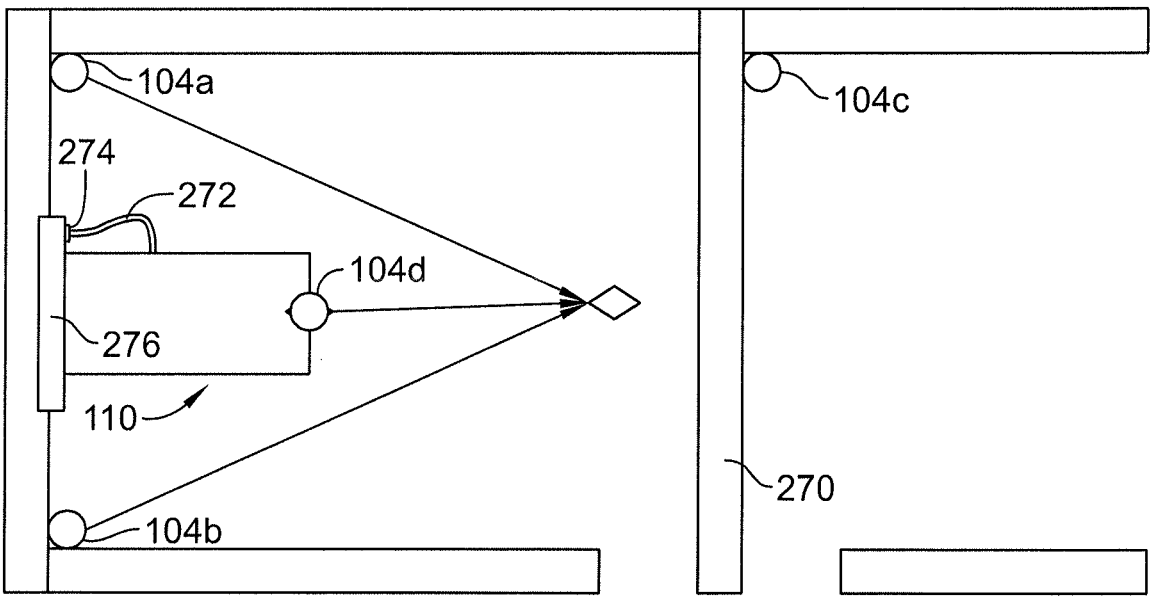
FIG. 9 is a diagrammatic top plan view, similar to FIG. 8, showing a bed in the first room, the bed having a locating tag that acts as a mobile tag when the bed is being transported through a healthcare facility and that acts as a UWB receiver or transceiver when the bed is determined to be stationary in a patient room as indicated in FIG. 9 by the locating tag on the bed being depicted as circle shaped, and showing the mobile tag in communication with the three UWB receivers or transceivers in the first patient room.

As alluded to above, the circuitry of tags 102 and the circuitry of transceivers 104 (aka receivers 104 and anchors 104) are the same in some embodiments. Thus, according to the present disclosure, a tag 102 on a piece of mobile medical equipment changes its role from being a tag 102 to being an anchor 104 under some circumstances. In particular, before changing roles from operating as a mobile tag 102 to operating as a stationary anchor 104, system 100 first determines that the piece of mobile medical equipment to which tag 102 is attached, has become stationary within the healthcare facility. As shown in FIG. 9, bed 110 is an example of a piece of mobile medical equipment that has become stationary in the first room.

In the illustrative example of FIG. 9, system 100 determines that bed 110 has become stationary in the room based on a power cord 272 of bed 110 having its plug 274 plugged into an outlet in the room. More particularly, at least one computer device 106, 150, 152, 154, 155 of system 100 receives a message from bed 110 indicating that the bed 110 has been plugged into a power outlet in the room and makes the determination that the bed is stationary. In the illustrative example, the power outlet is included in a headwall unit or bed locator unit 276. However, coupling plug 274 of power cord 272 of bed 110 to any power outlet in the room will suffice.

In some embodiments, the caster brakes of bed 110 are also required to be in the braked position, along with bed 110 being plugged into a power outlet, before the bed 110 is determined to be stationary by the at least one computer device 106, 150, 152, 154, 155 of system 100. Alternatively or additionally, bed 110 is determined to have become stationary in the room due to a nurse call cable having its connector, such as a standard 37-pin nurse call connector, coupled to a mating connector or port of a bed connector unit such as an audio station bed connector (ASBC) or a network interface unit (NIU). In FIG. 9, cable 272 and connector 274 may just as well depict such a nurse call cable and associated connector in lieu of depicting a power cord and plug. Further details of ASBC's and NIU's are shown and described in U.S. Pat. Nos. 7,538,659 and 7,319,386 and in U.S. Patent Application Publication Nos. 2009/0217080 A1, 2009/0212925 A1 and 2009/0212926 A1, each of which is hereby expressly incorporated by reference herein.

As shown diagrammatically in FIG. 9, the tag of bed 110 which switches to operating as an anchor 104d is coupled to a footboard or to a foot end frame member of bed 110 at a position about midway between the opposite sides of bed 110. Once bed 110 has its power cord 272 or nurse call cable 272 plugged in and, in some embodiments, its casters braked, system 100 knows that the general location of anchor 104d is about eight feet from the bed locator unit 276 or room wall having the ASBC or NIU. Thus, use of ranging events between the two anchors 104a, 104b and anchor 104d within the respective room is all that may be necessary to determine the location of anchor 104d. That is, the two circles generated based on a first distance between anchor 104a and anchor 104d (centered on anchor 104a), and based on a second distance between anchor 104b and anchor 104d (centered on anchor 104b), will intersect at two points, but the one closest to the distance eight feet from the wall or unit 276 in the room is the correct one.

After bed 110 is determined by system 100 to be stationary, then anchors 104a, 104b, 104d are used to determine the locations of mobile tags 102 within the respective room. Thus, communications between anchor 104c, as well as any other anchors 104 outside of the room in which bed 110 with anchor 104d is situated, are ignored in connection with determining the location of any tags 102 in the room having bed 110 with anchor 104d. The position of anchor 104d is modeled on a floor plan layout by the at least one computer 106, 150, 152, 154, 155 of system 100 in some embodiments. Even after the tag 102 of bed 110 of FIG. 9, changes its role so as to operate as anchor 104d of the corresponding system 100, circuitry 204 of bed 110 and/or one or more other computers 106, 150, 152, 154, 155 are still able to model a boundary, such as boundary 116 or boundary 256 or boundary 262, around bed 110 using the anchor 104d on the bed 110 (i.e., the anchor 104d that previously operated as tag 102) in some embodiments.

Based on the foregoing, therefore, locating system 100 includes a plurality of locating tags 102 including equipment locating tag 102 that coupled to a piece of mobile medical equipment, such as bed 110. A plurality of locating anchors 104a, 104b, 104c are mounted at fixed locations and in wireless communication with the plurality of locating tags 102. At least one computer 106, 150, 152, 154, 155 is communicatively coupled to the plurality of locating anchors 104a, 104b, 104c. The plurality of locating tags 102, the plurality of locating anchors 104a, 104b, 104c, and the at least one computer 106, 150, 152, 154, 155 cooperate to form a high-accuracy locating system operable to determine a location of each locating tag 102 of the plurality of locating tags 102 within at least one foot of an actual location of the locating tags 102. The equipment locating tag 102 has its role changed so as to operate as a locating anchor 104d of the plurality of locating anchors in response to the piece of mobile medical equipment 110 becoming stationary.

In some embodiments, the piece of mobile medical equipment 110 sends a signal to indicate that it has become stationary in response to a power cord 272 of the piece of medical equipment 110 being plugged into a power outlet. The piece of mobile medical equipment 110 includes patient bed 110 and, in some embodiments, the patient bed 110 sends a signal to indicate that it has become stationary in response to casters 128 of the patient bed 110 being braked. Thus, in some embodiments, the piece of mobile medical equipment 110 includes patient bed 110 that sends a signal to indicate that it has become stationary in response to casters 128 of the patient bed 110 being braked and the power cord 272 of the patient bed 110 being plugged into a power outlet. Alternatively, the piece of mobile medical equipment includes patient bed 110 that sends a signal to indicate that is has become stationary in response to a nurse call cable 272 of the patient bed being connected to a nurse call port, such as is included in an ASBC or NIU, located in the patient room.

As mentioned above, the piece of mobile medical equipment may include patient bed 110 and the equipment locating tag 102 may be coupled to the patient bed 110 near a foot end of the patient bed 110. For example, the equipment locating tag 102 may be coupled to a footboard of the patient bed. In the illustrative example, the piece of mobile medical equipment 110 is located in a patient room that has two locating anchors 104a, 104b at fixed locations and the equipment locating tag 102 becomes a third locating anchor 104d in the patient room after its role is changed to operate as one of the locating anchors 104 of system 100.

In some embodiments, prior to changing its role to operate as one of the locating anchors 104, a location of the equipment locating tag 102 is determined by the at least one computer 106, 150, 152, 154, 155 using two way ranging and time difference of arrival (TDOA) techniques. Alternatively or additionally, prior to changing its role to operate as one of the locating anchors 104, a location of the equipment locating tag 102 is determined by the at least one computer 106, 150, 152, 154, 155 using time of arrival (TOA) or time of flight (TOF) techniques. In the illustrative example, the equipment locating tag 102 communicates with the plurality of locating anchors 104a, 104b, 104c using ultra-wideband (UWB) signals. In some embodiments, the at least one computer 106, 150, 152, 154, 155 keeps track of whether the equipment locating tag 102 has changed roles to operating as one of the locating anchors 104, particularly illustrative anchor 104d.

The present disclosure contemplates that if bed 110 has two tags, such as tags 102a, 102b as shown for bed 110 of FIG. 6 for example, then in response to bed 110 having tags 102a, 102b determined by one or more of computers 106, 150, 152, 154, 155 to have become stationary, such as in any of the manners described above in connection with bed 110 of FIGS. 8 and 9, then both tags 102a, 102b have their role changed to operating as anchors 104 of the corresponding system 100 in some embodiments. In other embodiments, only one of tags 102a, 102b switches its role to operating as an anchor 104 in response to the associated bed 110 becoming stationary. For example, tag 102b adjacent the foot end of the bed 110 changes its role to operating as an anchor 104 in some embodiments. Even if either or both of tags 102a, 102b change roles so as to operate as anchors 104 of system 100, circuitry 204 of bed 110 and/or one or more other computers 106, 150, 152, 154, 155 are still able to model boundary 256 around bed 110 using the anchors 104 on the bed 110 (i.e., the anchors 104 that previously operated as tags 102a, 102b) in some embodiments.

In FIGS. 8 and 9, some components of system 100 are not shown. For example, network 108 and computer devices 106, 150, 152, 154, 155 are not shown. However, it should be understood that some or all of these components are, in fact, included in system 100 of FIGS. 8 and 9 and the discussion of these components herein is also applicable. Accordingly, the features of the embodiments of system 100 of FIGS. 8 and 9 may be used in combination with the features of any of systems 100 discussed herein in connection with FIGS. 1-7 and 10-13, if desired. Although the piece of mobile medical equipment shown in FIG. 9 is patient bed 110, it should be appreciated that tags 102 that switch roles to operating as anchors 104 of system 110 may be mounted to other types of medical equipment such as intravenous (IV) pumps, infusion pumps, electrocardiogram devices (EKG's), pulse oximeters, blood pressure measurement devices, ventilators, passive motion therapy devices, electroencephalogram devices (EEG's), deep vein thrombosis (DVT) treatment devices, and so forth.

Figure 10:
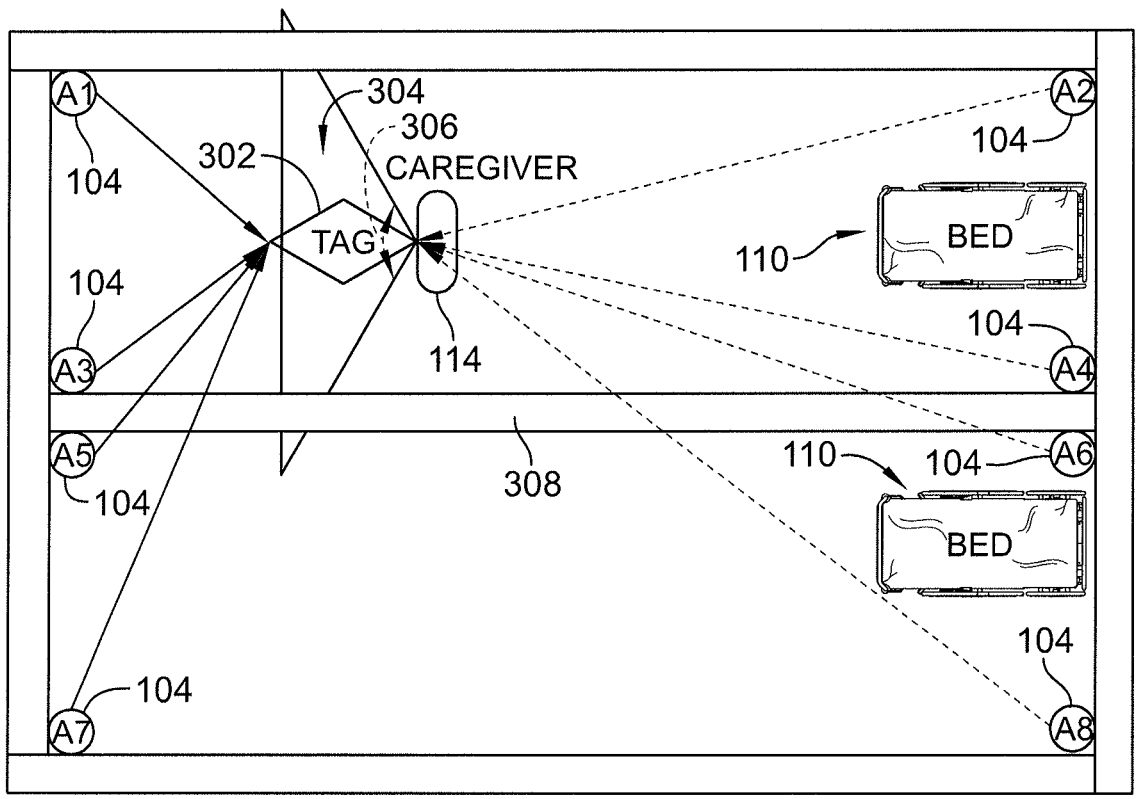
FIG. 10 is a diagrammatic top plan view showing a mobile locating tag (diamond shaped) carried by a caregiver and having a digital compass that is used to determine a direction of orientation of the locating tag and that is used to establish a field of good ranging (triangular shaped) through a predetermined angle in front of the locating tag and away from the caregiver's body.

Referring now to FIG. 10, a caregiver 114 transports an alternative embodiment of a caregiver locating tag 302 which has a digital compass that operates to determine a direction of orientation of tag 302 and that is used to establish a field of good ranging 304 through a predetermined angle 306 in front of the caregiver locating tag 302 and away from the caregiver's body. The benefits of using a digital compass in tag 302 will be understood in light of the following discussion regarding UWB locating, in general. In the discussion that follows, reference is made to tag 102 but it should be understood that the discussion is also applicable to systems 100 including one or more of tags 302.

When using indoor locating systems based on time of flight (TOF) or time difference of arrival (TDOA) in the UWB band, each node (or anchor 104) establishes a radius or a hyperbola centered about its location to the tag 102 that is attempting to be located. To solve for the actual location of the tag 102 in the easiest of cases, three intersecting circles intersect in one point only, and this is the solution for the location of the tag 102 of interest. Any number of techniques such as substitution or linear algebra can be used to solve for the single point. This single point can be found relative to some pre-established datum (e.g., origin 156 shown in FIG. 1), upon installation of the anchors 104, and thus the tag 102 can be found in two dimensional space. Things become a little more difficult when error or uncertainty occurs in establishing the radius from each anchor 104 to the tag 102.

An established technique for dealing with uncertainty in the system 100 is to use the reported radius from each anchor 104, whether the error is high or not, and to perform a least squares fit operation. This is a good approach for determining the approximate location of the tag 102 (e.g., within about 1 foot or less to about 3 feet of the actual tag location). However, this approach assumes that the error is the same for each reported radius. Due to differences in the amount of obstructions in one or more of the range results between anchors 104 and tags 102, the accuracy can be effected highly by just one pair.

The theory of time of flight (TOF) in UWB suggests that there are two main sources of error in non-line-of-sight (NLOS) instances. One source of error is signal attenuation. The general Equation 1 below shows the relationship of received and transmitted power:

$$P_r = P_t + G_{ant} - L_{board} - 20 \log_{10}(4 \times pi \times f \times (d/c)) - L_{mat} \quad \text{Equation 1:}$$

where $P_r$ is received power from tag 102 or anchor 104 at receiver; $P_t$ is transmitted power from tag 102 or anchor 104 at receiver; $G_{ant}$=gain of antenna on the transmitter; $L_{board}$ is the losses in the board of the receiver; F is transmit frequency; d is distance from anchor 104 to tag 102; c is the speed of light; and $L_{mat}$ is the attenuation through some obstruction between the anchor 104 and tag 102.

After all of the gains and losses, the power received ($P_r$) must be greater than a threshold set by the designer of system 100 in order for the event to be registered. Due to the short burst lengths, time of flight (TOF) locating with UWB mitigates multi-path concerns, but error can easily be introduced when the first-path (e.g., the non-reflected path) has been attenuated below the threshold and thus, is not picked up by the receiver of tag 102 or anchor 104, as the case may be. In these cases if the $n^{th}$ path is less attenuated, then the $n^{th}$ path could be thought to be the first path by the system 100.

Another source of error is refraction errors. Refraction errors exist when the first path refracts through an object and the overall length of the ray (e.g., detected signal path) from the anchor 104 to the tag 102 (or visa-versa) is lengthened and slowed down by traveling through different media. See signal 268 in FIG. 8, for example, which is refracted by wall 270. In general, the calculated first path when there are no obstructions in the signal path is as follows:

$$d_{los} = TOF_{los} * c \quad \text{Equation 2:}$$

where $d_{los}$ is the line-of-sight (needed) distance between the anchor 104 and tag 102; c is the speed of light; $TOF_{los}$ is the found time of flight between the anchor 104 and tag 102. When there are obstructions in the signal path, the distance between anchor 104 and tag 102 is calculated as follows:

$$d=d_{los}+w(R-1) \quad \text{Equation 3:}$$

where w is the width of the obstruction and R is the refraction index of the obstruction.

The present disclosure contemplates various ways to improve the accuracy of system 100 in light of the two sources of error just discussed. In various real life situations, there are more than three anchors 104 in a given area with which tag 102 is able to communicate. However, only three anchors 104 are needed to calculate the location of the tag 102 under most circumstances, so the following techniques can be used to determine the "best three" ranging calculations. In some embodiments, more than one of these techniques are used to identify the best three anchors 104 with which to base the location determination for any given tag 102.

A first technique is to only use the three anchors 104 with the highest received power (e.g., received signal strength or RSSI). A second technique is to compute the least squares with as many combinations of three anchors 104 as there are ranging data from, and then to keep the lowest sum of squared error out of all of those combinations. A third technique is to determine whether a calculated variance indicates that there is interference or attenuation between particular anchor 104/tag 102 pairs, which makes the respective ranging result untrustworthy. If more than three ranging results are found, only the three with the lowest variance are used to determine the location of the tag 102 according to the third technique.

According to a fourth technique, the received power at each anchor 104 from tag 102 is measured and logged through time. If there is a sudden dip of received power in one or more anchors 104, occurring generally simultaneously with an increase of received power of other anchors 104, it can be assumed that the subject (e.g., caregiver, patient, or equipment) is rotating in place, or an obstruction (such as another person) has moved into the line of sight between the tag 102 and the anchor 104 having the power dip. In either scenario, this may cause error in the determination of the location of the tag 102. Thus, according to the fourth technique ranging events from tag 102 to the one or more anchors 104 that suddenly dipped in received power are thrown out (e.g., erased from memory) or ignored (e.g., retained in memory but not used) in connection with the determination of the location of tag 102 by the at least one computer device 106, 150, 152, 154, 155 of system 100.

According to a fifth technique, it may be safe to assume that the longer ranges between tag 102 and anchors 104 have more potential to have more obstructions (and thus error) in the signal paths of the ranging events. Thus, according to the fifth technique, the determination of the location of tag 102 is based only on the ranging events with the three anchors 104 that are closest to the tag 102. A sixth technique uses self-calibration to increase the accuracy of system 100. Anchors 104, which are installed at fixed and known distances from each other, can range to one another. The actual distances between anchors 104 can be compared to the ranging event results between anchors 104. The comparison allows for losses through obstructions to be derived and then, henceforth, the at least one computer 106, 150, 152, 154, 155 uses the derived losses as a correction factor between anchors 104 and tags 102.

In some embodiments of system 100, instead of determining the strongest signal strength, ranging events that have passed through the human body are thrown out or ignored by the at least one computer 106, 150, 152, 154, 155 of system 100 because such signals passing through the human body have some refraction or multi-path concerns. Again referring to FIG. 10, signals from tags 302 having a digital compass are used by the at least one computer 106, 150, 152, 154, 155 of system 100 to determine a direction that tag 302 is oriented so that line-of-sight (or at least not attempting to radiate through the body) to the three or more best anchors 104 within the field of good ranging 304 is able to be determined. In some embodiments, the use of tags 302 with the digital compass having the field of good ranging 306 may be used in combination with any of the techniques discussed above for improving the accuracy of system 100.

Based on the foregoing, therefore, locating system 100 includes locating tag 302 that is transported (e.g., carried or worn) by a person (e.g., caregiver 114 or patient 112) and that has a digital compass. The digital compass is used to determine a direction of orientation of the locating tag 392 and is also used to establish a field of good ranging 304 through a predetermined angle 306 in front of the locating tag 302 and away from the person's body. The locating system 100 also includes a plurality of locating anchors 104 that are mounted at fixed locations within a facility and at least one computer 106, 150, 152, 154, 155 that is in communication with the plurality of locating anchors 104.

In FIG. 10, locating anchors 104 are also denoted alphanumerically as anchors A1-A8. As shown in FIG. 10, the ranging events that occur between the tag 302 and anchors A1, A3, A5, and A7 are not all LOS (line of sight) but none of them pass through the human body of caregiver 114, which is preferable. In particular, the ranging events between tag 302 and anchors A5, A7 pass through a wall 308 separating the two rooms. In some embodiments, the ranging events occurring between all anchors A1-A8 are passed to the location engine 106 or other computer device 150, 152, 154, 155 of system 100, but some are thrown out or ignored before computing the location of tag 302 because they are known to have passed through the body of the caregiver 114. Furthermore, the techniques discussed above are used in some embodiments to filter out spurious behavior. For instance, if one or more of the computers 106, 150, 152, 154, 155 of system 100 is getting "good" ranging data, and tracking a subject, and suddenly the least squares approximation locates the subject at a distance for which they couldn't possibly have moved within a short amount of time, the calculated new location is ignored, and it is assumed that the subject is actually at the previously calculated location.

In general, one or more computers 106, 150, 152, 154, 155 of system 100 (e.g., whichever of computers 106, 150, 152, 154, 155 analyze information from anchors 104) will not know if a given received power at anchors 104 includes losses from obstructions, or losses due to distance from the anchor 104 to the tag 302, or tag 102 in other embodiments. As discussed, one relatively large and frequent source of error is due to the ranging event passing through human bodies. It is contemplated by the present disclosure that the system 100 is able to identify when this is happening, so the system 100 can ignore those ranging results. To identify ranging events that pass through a person's body, a fast Fourier transform (FFT) is performed at numerous frequencies (e.g., channels) within the UWB within a small amount of time, and their ratios are calculated. The transfer function of electromagnetic radiation though water (a person) is known, and if it is found that the ratio is consistent with that of ranging events passing through water, the at least one computer 106, 150, 152, 154, 155 concludes that the ranging event passing through a person actually happened and acts accordingly.

In some cases, the ranging event through the person is not thrown out or ignored, but rather, is corrected for the refraction by the at least one computer 106, 150, 152, 154, 155. In other cases, the ranging event through the person is thrown out or ignored such that only line-of-sight (LOS) ranging results are used by the at least one computer 106, 150, 152, 154, 155 of system to determine the location of tag 302 or tag 102, as the case may be.

As is apparent in FIG. 10, anchors A1, A3, A5, A8 are within the field of good ranging 304 because they are in front of the caregiver 114 and anchors A2, A4, A6, A8 are not within the field of good ranging 304 because they are behind the caregiver 114. Thus, although the field of good ranging 304 is diagrammatically shown as a triangle in FIG. 10, it should be appreciated that the field of good ranging 304 extends beyond the diagrammatic triangle and is defined between extensions of the two sides of the diagrammatic triangle that define angle 306.

The at least one computer 106, 150, 152, 154, 155 of system 100 detects ranging events between the locating tag 302 and the plurality of locating anchors A1-A8. However, the at least one computer 106, 150, 152, 154, 155 determines a location of the locating tag 302 using only the ranging events associated with each of the locating anchors A1, A3, A5, A7 that are within the field of good ranging 304 established by the digital compass of tag 302 in the illustrative FIG. 10 example. Thus, the at least one computer 106, 150, 152, 154, 155 ignores the ranging events associated with each of the locating anchors A2, A4, A6, A8 that are not within the field of good ranging 304 established by the digital compass of tag 302 in the illustrative FIG. 10 example.

In some embodiments, the at least one computer 106, 150, 152, 154, 155 is configured to use a least squares fit technique to determine the location of the locating tag 302. Optionally, if more than three locating anchors 104 are within the field of good ranging 304, the at least one computer 106, 150, 152, 154, 155 determines the location of the locating tag 302 using only the three locating anchors 104 within the field of good ranging 304 that have highest received power. Further optionally, if more than three locating anchors 104 are within the field of good ranging 304, the at least one computer 106, 150, 152, 154, 155 determines the location of the locating tag 302 using only the three locating anchors 104 within the field of good ranging 304 that have lowest sums of squared error.

It is contemplated that, in some embodiments, if more than three locating anchors 104 are within the field of good ranging 304, the at least one computer 106, 150, 152, 154, 155 determines the location of the locating tag 302 using only the three locating anchors 104 within the field of good ranging 304 that have lowest variance. Alternatively, if more than three locating anchors 104 are within the field of good ranging 304, the at least one computer 106, 150, 152, 154, 155 determines the location of the locating tag 302 using only the three locating anchors 104 within the field of good ranging that are closest to the locating tag 302.

In some embodiments, the at least one computer 106, 150, 152, 154, 155 is configured to ignore ranging events between the locating tag 302 and any of the locating anchors 104 within the field of good ranging 304 that experience a sudden dip in received power. Optionally, the at least one computer 106, 150, 152, 154, 155 is configured to compare actual distances between respective pairs of the locating anchors 104 and calculated distances between the respective pairs of locating anchors 104 based on ranging events between the respective pairs of locating anchors 104 and to determine correction factors for respective locating anchors 104 to use on the ranging events with the locating tag 302 to account for attenuation losses.

If desired, the location of the locating tag 302 is determined by the at least one computer 106, 150, 152, 154, 155 using two way ranging and time difference of arrival (TDOA) techniques. Alternatively or additionally, the location of the locating tag 302 is determined by the at least one computer 106, 150, 152, 154, 155 using time of arrival (TOA) or time of flight (TOF) techniques. In the illustrative embodiment of FIG. 10, the equipment locating tag 302 communicates with the plurality of locating anchors 104 using ultra-wideband (UWB) signals. Optionally, the predetermined angle 306 of the field of good ranging 304 is at least 90 degrees. Further optionally, the predetermined angle 306 of the field of good ranging 304 is at least 120 degrees. Angles 306 of less than 90 degrees and more than 120 degrees for the field of good ranging 304 are within the scope of the present disclosure, however.

In some embodiments, the at least one computer 106, 150, 152, 154, 155 determines if the person's body (e.g., the body of caregiver 114) is obstructing a signal path between the locating tag 302 and one or more of the plurality of locating anchors 104 by performing a fast Fourier transform (FFT) on multiple frequencies within an ultra-wideband spectrum and comparing ratios of received signal power to a transfer function of electromagnetic radiation through water. In some such embodiments, if the at least one computer 106, 150, 152, 154, 155 determines that the person's body may be obstructing the signal path, the at least one computer ignores the ranging event between the locating tag 302 and any of the locating anchors 104 that may be determined to be obstructed by the person's body. Alternatively or additionally, if the at least one computer 106, 150, 152, 154, 155 determines that the person's body may be obstructing the signal path, the at least one computer corrects the ranging event to account for refraction through the person's body.

In FIG. 10, some components of system 100 are not shown. For example, network 108 and computer devices 106, 150, 152, 154, 155 are not shown. However, it should be understood that some or all of these components are, in fact, included in system 100 of FIG. 10 and, therefore, the discussion of these components herein is also applicable to system 100 of FIG. 10. Accordingly, the features of the embodiments of system 100 of FIG. 10 may be used in combination with the features of any of systems 100 discussed herein in connection with FIGS. 1-9 and 11-13, if desired. Thus, tag 302 having the digital compass to establish the field of good ranging 304 may be used in addition to, or in lieu of, any of the tags 102 disclosed herein in connection with systems 100 of FIGS. 1-9 and 11-13.

Figure 11:
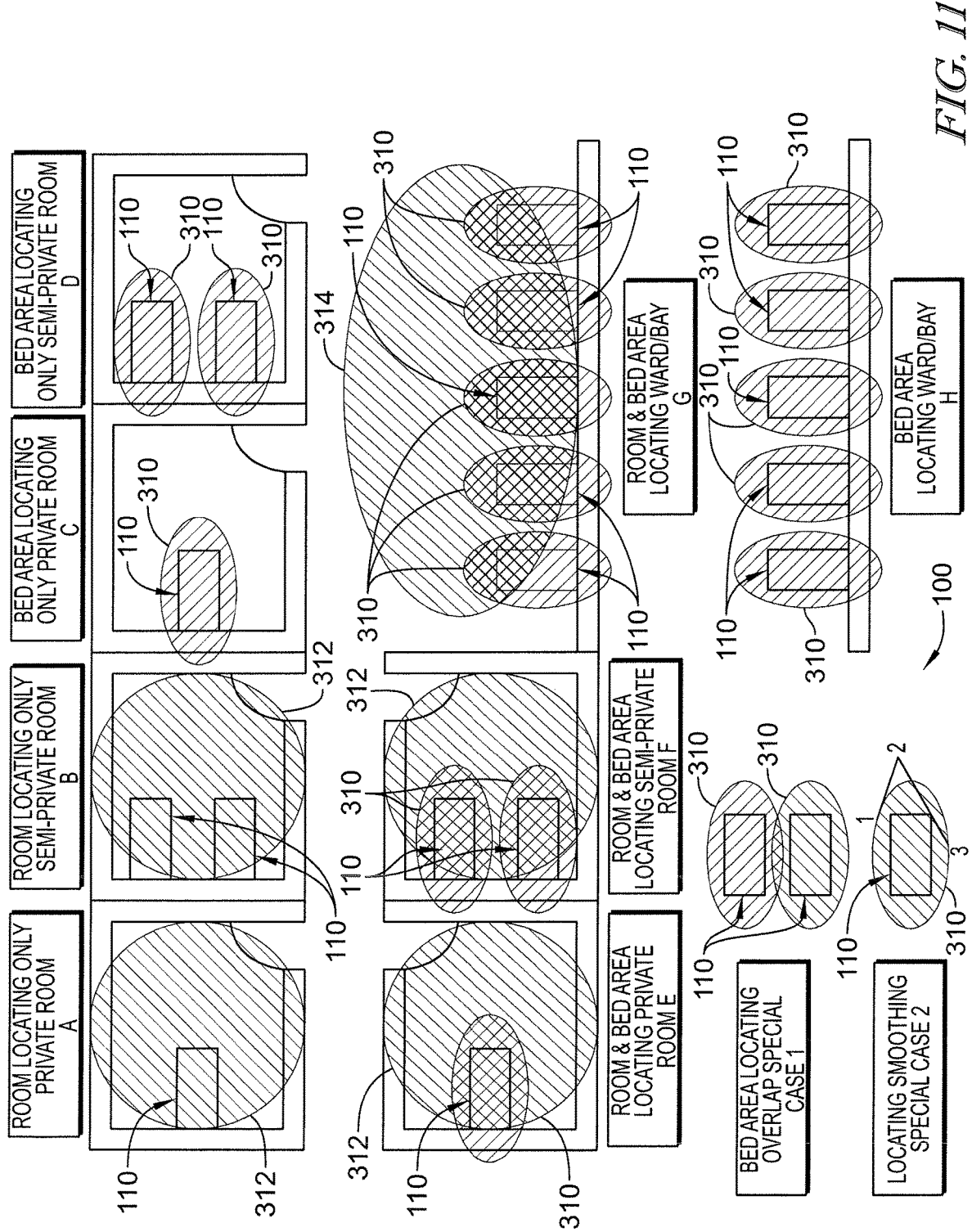
FIG. 11 is a diagrammatic top plan view showing patient beds in various rooms and in a multi-bed ward of a healthcare facility and showing that a computer models patient contact zones adjacent the beds based on the locations of equipment locating tags on the beds so that the computer is able to signal the beds to suppress monitoring of one or more bed conditions in response to a caregiver locating tag being detected in the patient contact zone and so that the computer is also able to determine that the caregiver has successfully completed a caregiver round.

Referring now to FIG. 11, a diagrammatic top plan view is provided showing patient beds 110 in various rooms (labeled as rooms A-F) and in a couple of multi-bed wards (labeled as G and H) of a healthcare facility. A couple of special cases (labeled as special case 1 and special case 2) are also shown in FIG. 11 in diagrammatic top plan view. It should be understood that system 100 having tags 102 (or 302), receivers 104 (aka transceivers 104 or anchors 104), hubs computers 150, 152, RTLS server 106, network 108, and servers 154, 155 are used in connection with the rooms A-F, wards G, H, and special cases 1 and 2 in FIG. 11.

However, these components are omitted from FIG. 11 for ease of illustration and discussion. The discussion herein of the embodiments of system 100 in connection with FIGS. 1-10, 12 and 13 are equally applicable to FIG. 11 unless specifically noted otherwise.

In FIG. 11, there are three different types of contact zones illustrated which will be referred to herein as a bed contact zone 310, room contact zone 312, and ward contact zone 314. Collectively, these zones are sometimes generically referred to herein as patient contact zones. Thus, in some embodiments, one or more of the computers 106, 150, 152, 154, 155 of system 100 models the patient contact zones, such as bed contact zones 310 adjacent the beds 110, based on the locations of equipment locating tags 102 on the beds 110 or based on patient locating tags 102 of patients 112 supported on beds 110. Alternatively or additionally, one or more of the computers 106, 150, 152, 154, 155 of system 100 models the patient contact zones, such as room contact zones 312 and/or ward contact zones 314, based on the locations of anchors 104 within the patient rooms or wards.

As will be discussed below, in response to caregiver locating tag 102 (or caregiver locating tag 302) being detected in the respective patient contact zones 310, 312, 314 under different scenarios, one or more of computers 106, 150, 152, 154, 155 of system 100 is configured to signal the beds 110 to suppress monitoring of one or more bed conditions and/or to suppress alerts being generated by bed 110 and/or to cancel any nurse calls being sent from the bed 110 or from the room. Furthermore, one or more of computers 106, 150, 152, 154, 155 is configured to determine that the caregiver 114 has successfully completed a caregiver round for one or more patients in response to a caregiver locating tag 102 (or caregiver locating tag 302) being detected in the respective patient contact zones 310, 312, 314 under different scenarios. The discussion below will refer to tags 102, but is equally applicable to embodiments of system 100 including tags 302.

Still referring to FIG. 11, room A is a private room having only a single bed 110 and one or more of computers 106, 150, 152, 154, 155 of system 100 only models room contact zone 312 in connection with room A. In response to tag 102 of a respective caregiver 114 entering room contact zone 312 of room A, one or more of computers 106, 150, 152, 154, 155 of system 100 performs the following functions via communication of appropriate messages to respective devices: a dome light or other type of nurse call indicator assembly adjacent the door to room A is illuminated to indicate that the caregiver 114 is present in room A; a status board at a master nurse call station is updated to indicate that the caregiver 114 is located in room A; if the PPM system of bed 110 in room A was armed to monitor patient position on, or exit from, bed 110, then the PPM system monitoring is suppressed; any nurse calls that have been placed from room A or from the bed 110 located in room A, are canceled based on the assumption that the caregiver 114 is attending to the condition(s) that precipitated the nurse call(s); any audible alarms that are occurring on bed 110 are suppressed (e.g., silenced or turned off); an amount of time that the caregiver 114 is present in room A is monitored; and after a threshold amount of time has elapsed, the caregiver 114 in room A gets credit for having completed a successful caregiver round.

In response to tag 102 of the caregiver 114 exiting room contact zone 312 of room A, one or more of computers 106, 150, 152, 154, 155 of system 100 performs the following functions via communication of appropriate messages to respective devices: the dome light or nurse call indicator assembly is no longer illuminated to indicate caregiver presence in room A; the status board at the master nurse call station is updated to indicate that the caregiver 114 is no longer located in room A; any audible alarm that was previously occurring on bed 110 is re-sounded or turned back on if the alarm condition causing the audible alarm prior to caregiver arrival in room A was not rectified or otherwise canceled prior to caregiver exit of room A; and if the PPM system of bed 110 in room A was armed to monitor patient position on, or exit from, bed 110 prior to entry of the caregiver 114 into room A, then the PPM system monitoring is re-enabled if the patient 112 is sensed by the PPM system of bed 110 to be present on the bed 110 and properly positioned. For additional details of nurse call indicator assemblies (aka dome lights) and status boards, see U.S. Pat. Nos. 8,384,526 and 8,779,924 which are hereby incorporated by reference herein in their entireties to the extent not inconsistent with the present disclosure which shall control as to any inconsistencies.

Room B of FIG. 11 is a semi-private room having two beds 110 located therein and, similar to room A, system 100 only models room contact zone 312 in connection with room B. In response to tag 102 of a respective caregiver 114 entering room contact zone 312 of room B, one or more of computers 106, 150, 152, 154, 155 of system 100 performs the following functions via communication of appropriate messages to respective devices: a dome light or other type of nurse call indicator assembly adjacent the door to room B is illuminated to indicate that the caregiver 114 is present in room B; a status board at a master nurse call station is updated to indicate that the caregiver 114 is located in room B; if the PPM system of either or both of beds 110 in room B were armed to monitor patient position on, or exit from, bed 110, then the PPM system monitoring of the respective bed 110 is suppressed; any nurse calls that have been placed from room B or from either or both beds 110 located in room B, are canceled based on the assumption that the caregiver 114 is attending to the condition(s) that precipitated the nurse call(s); any audible alarms that are occurring on either or both of beds 110 in room B are suppressed (e.g., silenced or turned off); an amount of time that the caregiver 114 is present in room B is monitored; and after a threshold amount of time has elapsed, the caregiver 114 in room B gets credit for having completed successful caregiver rounds for both patients 112 in room B, assuming two patients 112 are present in room B, otherwise the caregiver 114 gets credit for having completed a successful caregiver round for the single patient in room B.

In response to tag 102 of the caregiver 114 exiting room contact zone 312 of room B, one or more of computers 106, 150, 152, 154, 155 of system 100 performs the following functions via communication of appropriate messages to respective devices: the dome light or nurse call indicator assembly is no longer illuminated to indicate caregiver presence in room B; the status board at the master nurse call station is updated to indicate that the caregiver 114 is no longer located in room B; any audible alarm that was previously occurring on either or both of beds 110 in room B is re-sounded or turned back on if the alarm condition causing the audible alarm prior to caregiver arrival in room B was not rectified or otherwise canceled prior to caregiver exit of room B; and if the PPM system of either or both of beds 110 in room B were armed to monitor patient position on, or exit from, the respective bed 110 prior to entry of the caregiver 114 into room B, then the PPM system monitoring is re-enabled if the patient 112 is sensed by the PPM system of the respective bed 110 to be present on the respective bed 110 and properly positioned.

Room C of FIG. 11 is private room having only one bed 110 therein and system 100 only models bed contact zone 310 in connection with the bed 110 of room C. In response to tag 102 of a respective caregiver 114 entering bed contact zone 310 of room C, one or more of computers 106, 150, 152, 154, 155 of system 100 performs the following functions via communication of appropriate messages to respective devices: a dome light or other type of nurse call indicator assembly adjacent the door to room C is illuminated to indicate that the caregiver 114 is present in bed contact zone 310 of room C; a status board at a master nurse call station is updated to indicate that the caregiver 114 is located in bed contact zone 310 of room C; if the PPM system of bed 110 in room C was armed to monitor patient position on, or exit from, bed 110, then the PPM system monitoring is suppressed; any nurse calls that have been placed from room C or from the bed 110 located in room C, are canceled based on the assumption that the caregiver 114 is attending to the condition that precipitated the nurse call(s); any audible alarms that are occurring on bed 110 of room C are suppressed (e.g., silenced or turned off); an amount of time that the caregiver 114 is present in bed contact zone 310 of room C is monitored; and after a threshold amount of time has elapsed, the caregiver 114 in room C gets credit for having completed a successful caregiver round.

In response to tag 102 of the caregiver 114 exiting bed contact zone 310 of room C, one or more of computers 106, 150, 152, 154, 155 of system 100 performs the following functions via communication of appropriate messages to respective devices: the dome light or nurse call indicator assembly is no longer illuminated to indicate caregiver presence in bed contact zone 310 of room C; the status board at the master nurse call station is updated to indicate that the caregiver 114 is no longer located in bed contact zone 310 of room C; any audible alarm that was previously occurring on bed 110 is re-sounded or turned back on if the alarm condition causing the audible alarm prior to caregiver arrival in bed contact zone 310 of room C was not rectified or otherwise canceled prior to caregiver exit from the bed contact zone 310 of room C; and if the PPM system of bed 110 in room C was armed to monitor patient position on, or exit from, bed 110, prior to entry of the caregiver 114 into bed contact zone 310 of room C, then the PPM system monitoring is re-enabled if the patient 112 is sensed by the PPM system of bed 110 to be present on the bed 110 and properly positioned.

Room D of FIG. 11 is a semi-private room having two beds 110 therein and there is a bed contact zone 310 modeled around each bed 110 by one or more of computers 106, 150, 152, 154, 155 of system 100. Thus, there are two bed contact zones 310 in room D, one for each bed 110. The two beds 110 of room D will be referred to as bed 1 and bed 2 in the description that follows. In response to tag 102 of a respective caregiver 114 entering either of bed contact zones 310 of beds 1, 2 of room D, one or more of computers 106, 150, 152, 154, 155 of system 100 performs the following functions via communication of appropriate messages to respective devices: a dome light or other type of nurse call indicator assembly adjacent the door to room D is illuminated to indicate that the caregiver 114 is present in one of the bed contact zones 310 of beds 1, 2 of room D; a status board at a master nurse call station is updated to indicate that the caregiver 114 is located in one of bed contact zones 310 of beds 1, 2 of room D; an amount of time that the caregiver 114 is present in either of bed contact zones 310 of beds 1, 2 of room D is monitored; and after a threshold amount of time has elapsed, the caregiver 114 in room D gets credit for having completed a successful caregiver round for the patients on bed 1 and on bed 2 regardless of whether the caregiver 114 is in the contact zone 310 of bed 1 or the contact zone 310 of bed 2. Thus, the dome light and status board at the master nurse station are updated the same way and the caregiver time in room D for rounding assessment and successful rounding credit are updated the same way for patients on beds 1, 2 regardless of whether the tag 102 of the caregiver 114 is in contact zone 310 of bed 1 or contact zone 310 of bed 2.

In response to tag 102 of the respective caregiver 114 entering bed contact zone 310 of bed 1, if the PPM system of bed 1 in room D was armed to monitor patient position on, or exit from, bed 1, then the PPM system monitoring is suppressed; any nurse calls that have been placed from bed 1 located in room D, are canceled based on the assumption that the caregiver 114 is attending to the condition that precipitated the nurse call(s); and any audible alarms that are occurring on bed 1 of room D are suppressed (e.g., silenced or turned off). Similarly, in response to tag 102 of the respective caregiver 114 entering bed contact zone 310 of bed 2, if the PPM system of bed 2 in room D was armed to monitor patient position on, or exit from, bed 2, then the PPM system monitoring is suppressed; any nurse calls that have been placed from bed 2 located in room D, are canceled based on the assumption that the caregiver 114 is attending to the condition that precipitated the nurse call(s); and any audible alarms that are occurring on bed 2 of room D are suppressed (e.g., silenced or turned off). Thus, PPM monitoring suppression, nurse call cancellation, and alarm suppression only occurs for the individual bed 1 or bed 2, depending upon whether the tag 102 of the caregiver is located in zone 310 of bed 1 or zone 310 of bed 2, respectively.

In response to tag 102 of the caregiver 114 exiting bed contact zones 310 of beds 1, 2 of room D (e.g., tag 102 is not located in either of zones 310 of beds 1, 2), one or more of computers 106, 150, 152, 154, 155 of system 100 performs the following functions via communication of appropriate messages to respective devices: the dome light or nurse call indicator assembly is no longer illuminated to indicate caregiver presence in either of bed contact zones 310 of room D; the status board at the master nurse call station is updated to indicate that the caregiver 114 is no longer located in either of the bed contact zones 310 of room D; any audible alarm that was previously occurring on either of beds 110 of room D is re-sounded or turned back on if the alarm condition causing the audible alarm prior to caregiver arrival in the respective bed contact zone 310 of beds 1, 2 of room D was not rectified or otherwise canceled prior to caregiver exit from the respective bed contact zone 310 of room D; and if the PPM system of bed 1 or bed 2 in room D was armed to monitor patient position on, or exit from, bed 1 or bed 2, prior to entry of the caregiver 114 into the respective bed contact zone 310 of bed 1 or bed 2, respectively, of room D, then the PPM system monitoring is re-enabled on the respective bed 1, 2 if the respective patient 112 is sensed by the PPM system of the respective bed 1, 2 to be present on the respective bed 1, 2 and properly positioned.

Room E of FIG. 11 is a private room having one bed 110 therein and one or more of computers 106, 150, 153, 154, 155 of system 100 models bed contact zone 310 in connection with the bed 110 of room E. and also models room contact zone 312 in connection with room E. Thus, a substantial portion (e.g., 75% or more) of zone 310 overlaps with zone 312 in room E as shown in FIG. 11. In response to tag 102 of a respective caregiver 114 entering room contact zone 312 of room E, which occurs upon initial entry of the caregiver 114 into room E, one or more of computers 106, 150, 152, 154, 155 of system 100 performs the following functions via communication of appropriate messages to respective devices: a dome light or other type of nurse call indicator assembly adjacent the door to room E is illuminated to indicate that the caregiver 114 is present in room E; a status board at a master nurse call station is updated to indicate that the caregiver 114 is located in room E; any nurse calls that have been placed from room E or from the bed 110 located in room E, are canceled based on the assumption that the caregiver 114 is attending to the condition(s) that precipitated the nurse call(s); an amount of time that the caregiver 114 is present in zone 312 of room E is monitored; and after a threshold amount of time has elapsed, the caregiver 114 in zone 312 of room E gets credit for having completed a successful caregiver round.

In response to tag 102 of the respective caregiver 114 entering bed contact zone 310 of room E, which occurs after the caregiver 114 has moved sufficiently toward bed 110 in room E, one or more of computers 106, 150, 152, 154, 155 of system 100 performs the following functions via communication of appropriate messages to respective devices: if the PPM system of bed 110 in room E was armed to monitor patient position on, or exit from, bed 110, then the PPM system monitoring is suppressed; any audible alarms that are occurring on bed 110 of room E are suppressed (e.g., silenced or turned off); an amount of time that the caregiver 114 is present in zone 310 of room E is monitored and added to the amount of time that the caregiver 114 was in zone 312 of room E; and after a threshold amount of time has elapsed, the caregiver 114 in zone 310 of room E gets credit for having completed a successful caregiver round. In other words, the time that the caregiver 114 is in zone 312 of room E and the time that the caregiver is in zone 310 of room E, both count toward the time threshold for determining a successful round.

In response to tag 102 of the caregiver 114 exiting bed contact zone 310 of room E, one or more of computers 106, 150, 152, 154, 155 of system 100 performs the following functions via communication of appropriate messages to respective devices: any audible alarm that was previously occurring on bed 110 of room E is re-sounded or turned back on if the alarm condition causing the audible alarm prior to caregiver arrival in bed contact zone 310 of room E was not rectified or otherwise canceled prior to caregiver exit from the bed contact zone 310 of room E; and if the PPM system of bed 110 in room E was armed to monitor patient position on, or exit from, bed 110, prior to entry of the caregiver 114 into bed contact zone 310 of room E, then the PPM system monitoring is re-enabled if the patient 112 is sensed by the PPM system of bed 110 to be present on the bed 110 of room E and properly positioned.

In response to tag 102 of the caregiver 114 exiting room contact zone 312 of room E, such as occurs when the caregiver 114 exits room E altogether, one or more of computers 106, 150, 152, 154, 155 of system 100 performs the following functions via communication of appropriate messages to respective devices: the dome light or nurse call indicator assembly is no longer illuminated to indicate caregiver presence in room E and the status board at the master nurse call station is updated to indicate that the caregiver 114 is no longer located in room E. In other embodiments, different combinations of functions are carried by one or more of computers 106, 150, 152, 154, 155 of system 100 in response the tag 102 of the respective caregiver 114 entering or exiting zone 312 of room E and zone 310 of room E. For example, audible alarms may be turned off or suppressed in response to initial entry of the caregiver 114 into room contact zone 312 of room E instead of the later entry of the caregiver 114 into bed contact zone 310 of room E. As another example, nurse call cancellation may not occur until the caregiver 114 enters bed contact zone 310 of room E rather than upon entry of the caregiver 114 into room contact zone 312 of room E. Furthermore, in some embodiments, the time threshold for determining successful rounding by the caregiver 114 may only occur when the caregiver 114 is located in the bed contact zone 310 of room E and not while the caregiver is outside of zone 310 but in room contact zone 312 of room E.

Room F of FIG. 11 is a semi-private room having two beds 110 therein with a bed contact zone 310 modeled around each bed 110 by one or more of computers 106, 150, 152, 154, 155 of system 100 and with a room contact zone 312 also being modeled by the one or more computers 106, 150, 152, 154, 155 of system 100 in connection with room F. Thus, a substantial portion (e.g., 75% or more) of each bed contact zone 310 of the two beds 110 overlaps with zone 312 in room F as shown in FIG. 11. In response to tag 102 of a respective caregiver 114 entering room contact zone 312 of room F, which occurs upon initial entry of the caregiver 114 into room F, one or more of computers 106, 150, 152, 154, 155 of system 100 performs the following functions via communication of appropriate messages to respective devices: a dome light or other type of nurse call indicator assembly adjacent the door to room F is illuminated to indicate that the caregiver 114 is present in room F; a status board at a master nurse call station is updated to indicate that the caregiver 114 is located in room F; any nurse calls that have been placed from room F or from the beds 110 located in room F, are canceled based on the assumption that the caregiver 114 is attending to the condition(s) that precipitated the nurse call(s); an amount of time that the caregiver 114 is present in zone 312 of room F is monitored; and after a threshold amount of time has elapsed, the caregiver 114 in zone 312 of room F gets credit for having completed a successful caregiver round for the patients on both of beds 110 in room F, assuming both patients are present on beds 110 in room F.

As noted above, there are two bed contact zones 310 in room F, one for each bed 110. The two beds 110 of room F will be referred to as bed 1 and bed 2 in the description that follows. In response to tag 102 of the respective caregiver 114 entering bed contact zone 310 of bed 1 of room F, if the PPM system of bed 1 in room F was armed to monitor patient position on, or exit from, bed 1, then the PPM system monitoring is suppressed; any audible alarms that are occurring on bed 1 of room F are suppressed (e.g., silenced or turned off); an amount of time that the caregiver 114 is present in zone 310 of bed 1 of room F is monitored and added to the amount of time that the caregiver 114 was in zone 312 of room F; and after a threshold amount of time has elapsed, the caregiver 114 in zone 310 of bed 1 in room F gets credit for having completed a successful caregiver round for the patients on beds 1, 2 of room F, assuming both patients are present on beds 1, 2 of room F. In other words, the time that the caregiver 114 is in zone 312 of room F and the time that the caregiver is in zone 310 of bed 1 of room F, both count toward the time threshold for determining a successful round.

Similarly, in response to tag 102 of the respective caregiver 114 entering bed contact zone 310 of bed 2 of room F, if the PPM system of bed 2 in room F was armed to monitor patient position on, or exit from, bed 2, then the PPM system monitoring is suppressed; any audible alarms that are occurring on bed 2 of room F are suppressed (e.g., silenced or turned off); an amount of time that the caregiver 114 is present in zone 310 of bed 2 of room F is monitored and added to the amount of time that the caregiver 114 was in zone 312 of room F; and after a threshold amount of time has elapsed, the caregiver 114 in zone 310 of bed 2 in room F gets credit for having completed a successful caregiver round for the patients on beds 1, 2 of room F, assuming both patients are present on beds 1, 2 of room F. In other words, the time that the caregiver 114 is in zone 312 of room F and the time that the caregiver is in zone 310 of bed 2 of room F, both count toward the time threshold for determining a successful round.

In response to tag 102 of the caregiver 114 exiting bed contact zones 310 of beds 1, 2 of room F (e.g., tag 102 is not located in either of zones 310 of beds 1, 2 of room F), one or more of computers 106, 150, 152, 154, 155 of system 100 performs the following functions via communication of appropriate messages to respective devices: any audible alarm that was previously occurring on bed 1 or bed 2 of room F is re-sounded or turned back on if the alarm condition causing the audible alarm prior to caregiver arrival in bed contact zone 310 of bed 1 or bed 2, as the case may be, of room F was not rectified or otherwise canceled prior to caregiver exit from the bed contact zone 310 of the respective bed 1, 2 of room F; and if the PPM system of bed 1 or bed 2 in room F was armed to monitor patient position on, or exit from, the respective bed 1, 2, prior to entry of the caregiver 114 into bed contact zone 310 of room F, then the PPM system monitoring is re-enabled if the respective patient 112 is sensed by the PPM system of the respective bed 1, 2 of room F to be present on the respective bed 1, 2 of room F and properly positioned.

In response to tag 102 of the caregiver 114 exiting room contact zone 312 of room F, such as occurs when the caregiver 114 exits room F altogether, one or more of computers 106, 150, 152, 154, 155 of system 100 performs the following functions via communication of appropriate messages to respective devices: the dome light or nurse call indicator assembly is no longer illuminated to indicate caregiver presence in room F and the status board at the master nurse call station is updated to indicate that the caregiver 114 is no longer located in room F. In other embodiments, different combinations of functions are carried by one or more of computers 106, 150, 152, 154, 155 of system 100 in response the tag 102 of the respective caregiver 114 entering or exiting zone 312 of room F and either or both of zones 310 of room F. For example, audible alarms may be turned off or suppressed in response to initial entry of the caregiver 114 into room contact zone 312 of room F instead of the later entry of the caregiver 114 into one of the two bed contact zones 310 of room F.

As another example, nurse call cancellation may not occur until the caregiver 114 enters one of the two bed contact zone 310 of room F rather than upon entry of the caregiver 114 into room contact zone 312 of room F. In such embodiments, the nurse call is cancelled only for bed 1 or bed 2 corresponding to the zone 310 in which the caregiver is located, as the case may be. Furthermore, in some embodiments, the time threshold for determining successful rounding by the caregiver 114 may only occur when the caregiver 114 is located in the bed contact zone 310 of bed 1 or bed 2 of room F and not while the caregiver is outside of zones 310 but in room contact zone 312 of room F. In such embodiments, the successful round is credited only for the patient on bed 1 or bed 2, as the case may be, corresponding to the bed contact zone 310 in which the caregiver is located for the threshold period of time.

Ward or bay G of FIG. 11 illustratively has five beds 110 therein with a bed contact zone 310 modeled around each bed 110 by one or more of computers 106, 150, 152, 154, 155 of system 100 and with a ward contact zone 314 also being modeled by the one or more computers 106, 150, 152, 154, 155 of system 100 in connection with ward G. As shown in FIG. 11, a fair amount (e.g., roughly about 50% to about 75% or more) of each bed contact zone 310 of the five beds 110 overlaps with zone 314 in ward G. In response to tag 102 of a respective caregiver 114 entering ward contact zone 314 of ward G, which occurs upon initial entry of the caregiver 114 into ward G, one or more of computers 106, 150, 152, 154, 155 of system 100 performs the following functions via communication of appropriate messages to respective devices: a dome light or other type of nurse call indicator assembly adjacent the door to ward G is illuminated to indicate that the caregiver 114 is present in ward G; a status board at a master nurse call station is updated to indicate that the caregiver 114 is located in ward G; and any nurse calls that have been placed from ward G or from the beds 110 located in ward G, are canceled based on the assumption that the caregiver 114 is attending to the condition(s) that precipitated the nurse call(s).

As noted above, there are five bed contact zones 310 in ward G, one for each bed 110. The description below of the functions performed by system 100 in connection with caregiver presence in zone 310 of one of the five beds 110 of ward G is applicable to each of the individual five beds 110 of ward G unless specifically noted otherwise. In response to tag 102 of the respective caregiver 114 entering bed contact zone 310 of bed 110 of ward G, if the PPM system of bed 110 in ward G was armed to monitor patient position on, or exit from, the particular bed 110, then the PPM system monitoring is suppressed for that bed 110; any audible alarms that are occurring on the particular bed 110 of ward G are suppressed (e.g., silenced or turned off); an amount of time that the caregiver 114 is present in zone 310 of the particular bed 110 of ward G is monitored; and after a threshold amount of time has elapsed, the caregiver 114 in zone 310 of the particular bed 110 in ward G gets credit for having completed a successful caregiver round for the patient on the particular beds 110 of ward G, assuming the respective patient is present on the particular bed 110 of ward G.

In response to tag 102 of the caregiver 114 exiting the bed contact zone 310 of the particular bed 110 of ward G (e.g., tag 102 is not located in any of zones 310 of the five beds 110 of ward G), one or more of computers 106, 150, 152, 154, 155 of system 100 performs the following functions via communication of appropriate messages to respective devices: any audible alarm that was previously occurring on the particular bed 110 of ward G is re-sounded or turned back on if the alarm condition causing the audible alarm prior to caregiver arrival in bed contact zone 310 of the particular bed 110 of ward G was not rectified or otherwise canceled prior to caregiver exit from the bed contact zone 310 of the respective bed 110 of ward G; and if the PPM system of the particular bed 110 in ward G was armed to monitor patient position on, or exit from, the particular bed 110 prior to entry of the caregiver 114 into bed contact zone 310 of the particular bed of ward G, then the PPM system monitoring is re-enabled if the respective patient 112 is sensed by the PPM system of the respective bed 110 of ward G to be present on the respective bed 110 of ward G and properly positioned.

In response to tag 102 of the caregiver 114 exiting ward contact zone 314 of ward G, such as occurs when the caregiver 114 exits ward G altogether, one or more of computers 106, 150, 152, 154, 155 of system 100 performs the following functions via communication of appropriate messages to respective devices: the dome light or nurse call indicator assembly is no longer illuminated to indicate caregiver presence in ward G and the status board at the master nurse call station is updated to indicate that the caregiver 114 is no longer located in ward G. In other embodiments, different combinations of functions are carried by one or more of computers 106, 150, 152, 154, 155 of system 100 in response the tag 102 of the respective caregiver 114 entering or exiting zone 314 of ward G and any of zones 310 of the five beds 110 of ward G. For example, audible alarms may be turned off or suppressed for all five beds 110 in response to initial entry of the caregiver 114 into ward contact zone 314 of ward G instead of the later entry of the caregiver 114 into one of bed contact zones 310 of a particular bed 110 of ward G. As another example, nurse call cancellation may not occur until the caregiver 114 enters the bed contact zone 310 of one of the five beds 110 of ward G rather than canceling nurse calls for all five of beds 110 upon entry of the caregiver 114 into ward contact zone 314 of ward G. In such embodiments, the nurse call is cancelled only for the particular bed 110 of ward G corresponding to the zone 310 in which the caregiver is located.

Ward or bay H of FIG. 11 illustratively has five beds 110 therein with a bed contact zone 310 modeled around each bed 110 by one or more of computers 106, 150, 152, 154, 155 of system 100. Ward H is similar to ward G, but the ward contact zone 314 is omitted from the illustrative ward H scenario. As just noted above, there are five bed contact zones 310 in ward H, one for each bed 110. The description below of the functions performed by system 100 in connection with caregiver entry into, and exit from, zone 310 of one of the five beds 110 of ward H is applicable to each of the individual five beds 110 of ward H unless specifically noted otherwise.

In response to tag 102 of a respective caregiver 114 entering bed contact zone 310 of a particular bed 110 of ward H, one or more of computers 106, 150, 152, 154, 155 of system 100 performs the following functions via communication of appropriate messages to respective devices: a dome light or other type of nurse call indicator assembly adjacent the door to ward H is illuminated to indicate that the caregiver 114 is present in ward H; a status board at a master nurse call station is updated to indicate that the caregiver 114 is located in ward H; if the PPM system of the particular bed 110 in ward H was armed to monitor patient position on, or exit from, bed 110, then the PPM system monitoring is suppressed; any nurse calls that have been placed from the particular bed 110 of ward H, are canceled based on the assumption that the caregiver 114 is attending to the condition that precipitated the nurse call(s) from the particular 110; any audible alarms that are occurring on the particular bed 110 of ward H are suppressed (e.g., silenced or turned off); an amount of time that the caregiver 114 is present in bed contact zone 310 of the particular bed 110 of ward H is monitored; and after a threshold amount of time has elapsed, the caregiver 114 in zone 310 of the particular bed 110 of ward H gets credit for having completed a successful caregiver round for the patient on the particular bed 110 of ward H, assuming the patient 112 is, in fact, present on the particular bed 110 of ward H.

In response to tag 102 of the caregiver 114 exiting bed contact zone 310 of the particular bed of ward H, one or more of computers 106, 150, 152, 154, 155 of system 100 performs the following functions via communication of appropriate messages to respective devices: the dome light or nurse call indicator assembly is no longer illuminated to indicate caregiver presence in bed contact zone 310 of the particular bed 110 of ward H; the status board at the master nurse call station is updated to indicate that the caregiver 114 is no longer located in bed contact zone 310 of the particular bed 110 of ward H; any audible alarm that was previously occurring on the particular bed 110 of ward H is re-sounded or turned back on if the alarm condition causing the audible alarm prior to caregiver arrival in bed contact zone 310 of the particular bed 110 of ward H was not rectified or otherwise canceled prior to caregiver exit from the bed contact zone 310 of the particular bed 110; and if the PPM system of the particular bed 110 of ward H was armed to monitor patient position on, or exit from, the particular bed 110, prior to entry of the caregiver 114 into bed contact zone 310 of the particular bed 110 of ward H, then the PPM system monitoring is re-enabled if the patient 112 is sensed by the PPM system of bed 110 to be present on the particular bed 110 of ward H and properly positioned.

Still referring to FIG. 11, a special case 1 is shown in which bed contact zones 310 of two adjacent beds 110 overlap to some extent. Such a situation may occur in connection with rooms D and F and in connection with wards G and H of FIG. 11, for example. If one or more of computers 106, 150, 152, 154, 155 of system 100 determines that a locating tag 102 is located within the area of overlap of zones 310, then in some embodiments, the one or more computers 106, 150, 152, 154, 155 simply acts as if the locating tag is outside of both zones 310 altogether. That is, the functions that are described above as occurring when a caregiver locating tag 102 is in a particular zone 310, do not occur at all when the caregiver locating tag is in the area of overlap. In other embodiments, the functions that are described above as occurring when a caregiver locating tag 102 is in a particular zone 310, occur for both beds 110 having the overlapping zones 310. Alternatively or additionally, if the caregiver locating tag 102 is located within one zone 310 or the other zone 310 that overlap prior to entering and being located in the area of overlap of the two zones 310, then the functions that are described above as occurring when a caregiver locating tag 102 is in a particular zone 310 continues to occur for the particular bed 110 associated with the zone 310 in which the caregiver locating tag 102 was located prior to entering the area of overlap of the two zones 310.

A locating smoothing special case 2 is also depicted in FIG. 11. In special case 2, one bed contact zone 310 is shown around a corresponding bed 110 and numbers 1, 2, and 3 are provided to indicate the calculated locations of a locating tag 102 at times t1, t2, and t3, respectively. Assuming location calculations for tags 102 are made by system 100 fairly quickly, such as every half second or less, or every one second, for example, it can be appreciated that it is unlikely that the locating tag 102 moves between locations 1, 2 and 3 within one second (in the case of half second between location calculations) or even within two seconds (in the case of one second between location calculations). Thus, in situations in which the locating tag 102 appears to jump around from location to location too quickly, or in situations in which different combinations of anchors 104 locate the tag 102 at different locations simultaneously (e.g., locations 1, 2 and 3), then one or more of computers 106, 150, 152, 154, 155 implement a smoothing algorithm to average out the sporadic movement or simultaneous locations so that the caregiver locating tag 102 is determined by the one or more computers 106, 150, 152, 154, 155 to be at a stable location. Thus, the smoothing operation takes out high frequency components in the time-series data of locations for tag 102 using a moving average or filtering technique. For example, a temporal and/or spatial hysteresis algorithm is used in some embodiments to eliminate dithering of the movement of tag 102. Once the tag 102 moves by a sufficient amount from one location to another for a sufficient time, then one or more of computers 106, 150, 152, 154, 155 will detect the movement, possibly with a slight lag while the filtering or temporal and/or spatial hysteresis algorithm catches up to the actual movement of tag 102.

In the discussion above of zones 310 of rooms C, D, E, F, wards G, H, and special cases 1 and 2, it has been assumed that zone 310 is established around a respective bed 110 such as by modeling the boundary of zone 310 around bed 110 based on one or more equipment locating tags 102 mounted to the respective bed 110. In other embodiments, zones 310 for the examples of rooms C, D, E, F, wards G, H, and special cases 1 and 2 are modeled around patient locating tags 102 that are attached to, worn by, or otherwise carried by respective patients 112. Thus, the discussions above regarding the examples of rooms C, D, E, F, wards G, H, and special cases 1 and 2 are equally applicable to embodiments in which zones 310 are modeled by system 100 based on locations of patient locating tags 102 rather than based on equipment locating tags 102. Thus, alarms, monitoring functions, and nurse calls relating to any equipment within zone 310 around a patient equipment tag 102 are suppressed, canceled, re-enabled, re-sounded, etc., as the case may be, in a manner similar to that discussed above in connection with beds 110 in the various embodiments of FIG. 11.

Based on some embodiments of the foregoing, therefore, a locating and bed control system 100 includes bed 110 configured to support patient 112 thereon. The bed 110 has at least one sensor (e.g., sensors 222, load cells of scale system 224, caster braking sensors, deck section angle sensors, siderail position sensors, etc.) to monitor a bed condition and generate an alarm if the bed condition is sensed to be in an alarm state by the at least one sensor. The system 100 also includes equipment locating tag 102 to the bed 110, caregiver locating tag 102 coupled to caregiver 114, a plurality of receivers 104 mounted at fixed locations and in wireless communication with the equipment locating tag 102 and the caregiver locating tag 102, and at least one computer 106, 150, 152, 154, 155 communicatively coupled to the plurality of receivers 104. The equipment locating tag 102, the caregiver locating tag 102, the plurality of receivers 104, and the at least one computer 106, 150, 152, 154, 155 cooperate to form a high-accuracy locating system that is operable to determine a location of the equipment locating tag 102 and the caregiver locating tag 102 within at least one foot of an actual location of the equipment locating tag 102 and the caregiver locating tag 102, respectively. The at least one computer 106, 150, 152, 154, 155 models a patient contact zone (e.g., one or more of zones 310, 312, 314) adjacent the bed 110 based on the location of the equipment locating tag 102. The at least one computer 106, 150, 152, 154, 155 signals the bed 110 to suppress monitoring of the bed condition by the at least one sensor in response to the caregiver locating tag 102 being detected in the patient contact zone 310, 312, 314 and the at least one computer 106, 150, 152, 154, 155 also determines that the caregiver has successfully completed a caregiver round in response to the caregiver locating tag being detected in the patient contact zone 310, 312, 314 in various circumstances in the various embodiments described above in connection with FIG. 11.

In some embodiments of system 100 of FIG. 11, the at least one sensor includes a patient position monitoring (PPM) sensor (e.g., a load cell of scale system 224) and the alarm is generated in response to the PPM sensor detecting that the patient 112 has moved toward exiting the bed 110 by a threshold amount. Thus, after monitoring of the bed condition by the PPM sensor has been suppressed by the at least one computer 106, 150, 152, 154, 155, the caregiver 114 is able to assist the patient 112 in getting out of the bed 110 without the alarm being generated. If desired, the PPM sensor is re-enabled to monitor for the alarm condition in response to the patient 112 being returned to bed 110 and the caregiver locating tag 102 being detected to have left the patient contact zone 310, 312, 314.

Optionally, the bed 110 of includes a nurse call input (e.g., one of inputs 228) that is selectable by the patient 110 to place a nurse call and the at least one computer 106, 150, 152, 154, 155 is configured to send a message to cancel the nurse call in response to the caregiver locating tag 102 being detected in the patient contact zone 310, 312, 314 under various circumstances in various embodiments of the system 100 of FIG. 11. Alternatively or additionally, generation of the alarm may result in a nurse call being sent from the bed 110 to a nurse call computer (e.g., a master station of a nurse call system) and the at least one computer 106, 150, 152, 154, 155 is configured to send a message to the nurse call computer to cancel the nurse call in response to the caregiver locating tag 102 being detected in the patient contact zone 310, 312, 314.

In some embodiments, the bed 110 is located in a patient room and the system 100 furthers include a second bed 110 located in the patient room. In such embodiments, the at least one computer 106, 150, 152, 154, 155 is configured to determine that the caregiver has successfully completed caregiver rounds for the patient 112 on the bed 110 and for a second patient 112 on the second bed 110 in response to the caregiver locating tag 102 being detected in the patient contact zone 310, 312 adjacent the bed 110 or in response to the caregiver locating tag 102 being detected in a second patient contact zone 310, 312 adjacent the second bed 110.

It is contemplated by the present disclosure that the patient contact zone 310 may be defined as being within a boundary that may be about three feet from a periphery of the bed 110. For example, the patient contact zone 310 may be defined as being within a boundary calculated as being about three feet away from a footprint of the bed 110 as theoretically projected onto a floor supporting the bed 110. Alternatively, the patient contact zone 310 may be defined as being within a circular boundary having a radius of about five feet and centered on the equipment locating tag 102. Further alternatively, the patient contact zone 310 may be defined as being within an ellipse-shaped boundary that may extend beyond both sides and both ends of the bed 110.

In some embodiments of system 100 of FIG. 11, the equipment locating tag 102 and the caregiver locating tag 102 communicate with the plurality of receivers 104 via ultra-wideband (UWB) signals. If desired, the locations of the equipment locating tag 102 and the caregiver locating tag 102 of embodiments of system 100 of FIG. 11 are determined by the at least one computer 106, 150, 152, 154, 155 using two way ranging and time difference of arrival (TDOA) techniques. Alternatively or additionally, the locations of the equipment locating tag 102 and the caregiver 102 locating tag of the embodiments of system 100 of FIG. 11 are determined by the at least one computer 106, 150, 152, 154, 155 using time of arrival (TOA) at which transmissions from the equipment locating tag 102 and the caregiver locating tag 102 are received at the plurality of receivers 104.

Optionally, the at least one computer 106, 150, 152, 154, 155 of the embodiments of system 100 of FIG. 11 uses signals from only a subset of the plurality of receivers 104 to determine the location of the equipment locating tag 102 and the caregiver locating tag 102. The subset of the receivers 104 may be determined based on signal strength of signals from the equipment locating tag 102 and the caregiver locating tag 102 to the plurality of receivers 104. For example, the subset of receivers 104 may include at least three receivers 104 from the plurality of receivers 104 of the embodiments of system 100 of FIG. 11 having highest signal strength values as compared to others of the plurality of receivers 104.

In some embodiments, the at least one sensor of bed 110 of the embodiments of system 100 of FIG. 11 is configured to sense a presence of patient 112 on the bed 110 and the at least one computer 106, 150, 152, 154, 155 is configured to determine that a successful caregiver round has occurred only if the patient 112 is present on the bed 100 as sensed by the sensor. It is contemplated by the present disclosure that the locating and bed control system 100 may further include a patient locating tag 102 coupled to patient 112 and the at least one computer 106, 150, 152, 154, 155 may be configured to determine that a successful caregiver round has occurred only if the patient locating tag 102 is determined to be within the patient contact zone 310 with the caregiver locating tag 102.

Figure 12:
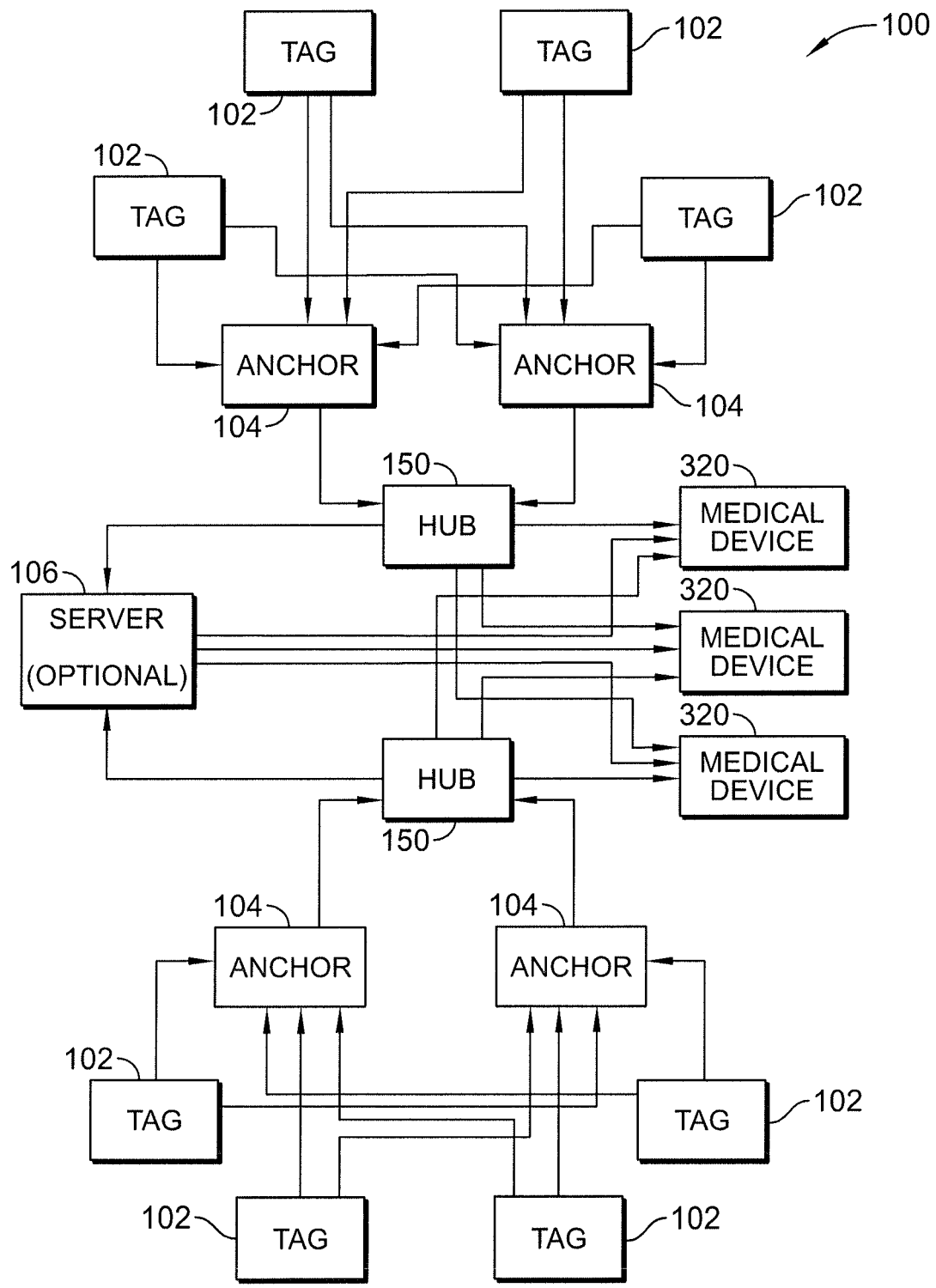
FIG. 12 is a block diagram showing a locating system having a plurality of locating tags, a plurality of locating anchors in wireless communication with the locating tags, and a plurality of processing hubs communicatively coupled to subsets of the locating anchors, and showing an optional locating server communicatively coupled to the processing hubs.

Referring now to FIG. 12, an embodiment of locating system 100 is shown having multiple locating tags 102, multiple locating anchors 104 in wireless communication with the locating tags 102, and multiple processing hubs 150 communicatively coupled to subsets of the locating anchors 104. As also shown in FIG. 12 locating server 106 is an optional component and when present, is communicatively coupled to the processing hubs 150. Thus, the present disclosure contemplates embodiments of system 100 that is devoid of any locating server 106 or other server (e.g., servers 154, 155) as part of the location system. As such, the software used to make the determinations as to the locations of tags 102 is made entirely at hubs 150 in such embodiments.

Although, only two anchors 104 are shown as being communicatively coupled to each hub 150 in FIG. 12, it should be appreciated that three or more anchors 104 are coupled to each hub 150 in real world implementations. Each hub 150 determines the locations of tags 102 that are in wireless communication with the respective anchors 104 that are coupled to the corresponding hub 150. Once the locations of tags 102 are determined at hubs 150, the locations are communicated to other computer devices for display of the location information (e.g., mobile devices of caregivers, room stations of nurse call systems, status boards of nurse call systems, master nurse stations of nurse call systems, computers of an EMR system, computers of a workflow system, and so forth) in some embodiments.

In the illustrative example of FIG. 12, hubs 150 are communicatively coupled (e.g., either via wireless communication or wired communication) with multiple medical devices 320. In particular, three medical devices 320 are shown in FIG. 12 with each medical device being in communication with both hubs 150 and with the optional server 106. However, in other embodiments, more or less than three medical devices 320 are in communication with the hubs 150 and, if present, with server 106 of system 100 of FIG. 12. In some embodiments, each hub 150 communicates with only a particular subset of medical devices 320. For example, medical devices 320 in different wards or units of a healthcare facilitate may be in communication only with one more hubs 150 associated with the particular ward or unit and not with hubs 150 associated with other wards or units.

The locating hubs 150 are configured to send location data to one or more medical devices 320. In particular, hubs 150 send location data indicative of the locations of the tags 102 that are in communication with the particular hub 150 via corresponding anchors 104. Alternatively or additionally, the processing hubs 150 of are configured to send commands to one or more medical devices 320 to control a feature of the medical device 320. It is contemplated by the present disclosure that the commands are sent to the one or more medical devices 320 by the processing hubs 150 in response to at least one of the locating tags 102 of the plurality of locating tags 102 being located within a device zone (not shown but similar to zones 116, 256, 262, 310 around beds 110) of the respective medical devices 320. For example, in some embodiments, at least one of the commands is an alarm silence command to silence an alarm of the respective medical device 320 in response to caregiver locating tag 102 being located in the device zone. Alternatively or additionally, at least one of the commands is a nurse call cancel command to cancel a nurse call originating from the respective medical device 320. It is within the scope of the present disclosure for the plurality of medical devices 320 to include all types of devices used in the healthcare setting for medical care including one or more of the following: a hospital bed 110 or other patient support apparatus 110, a vital signs monitor, an intravenous (IV) pump, a mattress controller, a deep vein thrombosis (DVT) therapy device, a passive motion machine, a pulse oximeter, or a patient lift, just to name a few.

Figure 13:
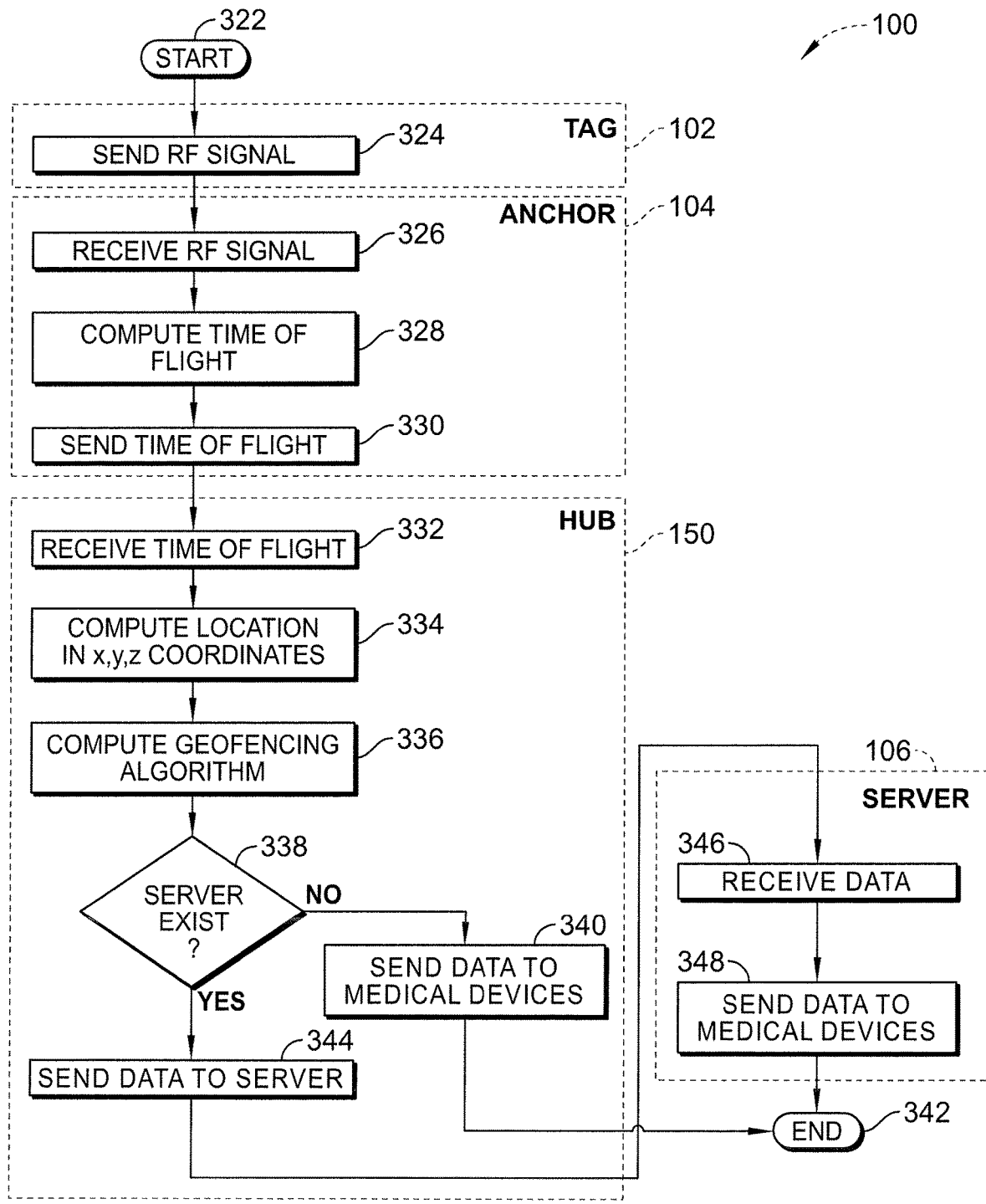
FIG. 13 is a flow chart showing an algorithm or functions cooperatively implemented by the locating tags, the locating anchors, the processing hubs, and, if present, the optional server of FIG. 12 to determine the locations of the locating tags and to send locating data and/or commands to medical devices.

Referring now to FIG. 13 various functions of system 100 of FIG. 12 that are cooperatively implemented by the locating tags 102, the locating anchors 104, the processing hubs 150, and, if present, the optional server 106 are shown. The functions shown in FIG. 13 are used to determine the locations of the locating tags 102 and to send locating data and/or commands to the medical devices 320. In FIG. 13, only one tag 102, one anchor 104, one hub 150, and one optional server 106 is shown for ease of description. However, the described functions are equally applicable to each of the multitude of like components included in system 100.

At block 322 of FIG. 13, system 100 starts its functions of locating tags 102. In particular, after the start indicated at block 322, tag 102 sends an RF signal (e.g., an UWB signal) as indicated at block 324. The wireless RF signal sent from tag 102 is sent periodically, such as at regular intervals, in some embodiments. After the tag 102 sends the RF signal at block 324, one or more anchors 104 within the reception range of tag 102 receives the RF signal as indicated at block 326. After receipt of the RF signal at block 326, the anchor 104 proceeds to compute the time of flight (TOF) of the RF signal as indicated at block 328. After the TOF of the RF signal is calculated at block 328; the anchor 104 sends the TOF information to hub 150 as indicated at block 330.

After the TOF information is sent from anchor 104 at block 330, hub 150 receives the TOF information as indicated at block 332. After receiving the TOF information at block 332, hub 150 computes the location of tag 102 in x, y, z coordinates, in some embodiments, as indicated at block 334. In other embodiments, the location of tag 102 is computed at block 334 in only x, y coordinates. See the discussion above in connection with FIG. 1 in this regard. After the location of tag 102 is computed at block 334, hub 150 computes a geofencing algorithm as indicated at block 336 to determine whether the tag is within a zone of interest (e.g., a medical device zone similar to zones 116, 256, 262, 310 around beds 110 or other patient contact zones 312, 314).

After computing the geofencing algorithm of block 336, hub 150 determines whether system 100 includes locating server 106 as indicated at block 338. If at block 338 the hub 150 determines that the server does not exist within system 100, then hub 150 sends the locating data and/or command data to the relevant medical devices 320 as indicated at block 340. The relevant medical devices 320 include those are that within the zone of interest as computed at block 336 in some embodiments or that are within some other programmed zone of interest. After the data is sent by hub 150 to the relevant medical devices 320 at block 340, the illustrative FIG. 13 functions of system 100 end as indicated at block 342, at least until the functions start again at block 322, such as in response to the next transmission of an RF signal from locating tag 102.

If at block 338 hub 150 determines that server 106 does exist within system 100, then hub 150 sends the locating data and/or command data to server 106 as indicated at block 344. After hub 150 sends the data to server 106 as indicated at block 344, server 106 receives the data as indicated at block 346. After server 106 receives the data as indicated at block 346, server 106 sends the locating data and/or command data to the relevant medical devices 320 as indicated at block 348. Again, the relevant medical devices 320 include those are that within the zone of interest as computed at block 336 in some embodiments or that are within some other programmed zone of interest. After the data is sent by server 106 to the relevant medical devices 320 at block 340, the illustrative FIG. 13 functions of system 100 end as indicated at block 342, at least until the functions start again at block 322, such as in response to the next transmission of an RF signal from locating tag 102.

Based on the foregoing, locating system 100 includes a plurality of locating tags 102 that are coupled to personnel within a facility, a plurality of locating anchors 104 that are mounted at fixed locations and in wireless communication with the plurality of locating tags 102, and a plurality of processing hubs 150 that are communicatively coupled to subsets of the plurality of locating anchors 104. The plurality of locating tags 102, the plurality of locating anchors 104, and the processing hubs 150 of system 100 of FIGS. 12 and 13 cooperate to form a high-accuracy locating system operable to determine a location of each locating tag 102 of the plurality of locating tags 102 within at least one foot of an actual location of the locating tags 102 and the high-accuracy locating system is devoid of any locating server 106, in some embodiments.

In illustrative embodiments, the locating system 100 of FIGS. 12 and 13 further includes a plurality of medical devices 320. The locating hubs 150 are configured to send location data to one or more medical devices 320 of the plurality of medical devices 320. Alternatively or additionally, the processing hubs 150 are configured to send commands to one or more medical devices 320 to control a feature of the medical device 320. If desired, the commands are sent to the one or more medical devices 320 by the processing hubs 150 in response to a first locating tag 102 of the plurality of locating tags 102 being located within a device zone of the respective medical devices 320. In some embodiments, at least one of the commands is an alarm silence command to silence an alarm of the respective medical device 320, for example. Alternatively or additionally, at least one of the commands is a nurse call cancel command to cancel a nurse call originating from the respective medical device 320. Optionally, the plurality of medical devices 320 of the system 100 of FIGS. 12 and 13 include one or more of the following: a hospital bed 110, a vital signs monitor, an intravenous (IV) pump, a mattress controller, a deep vein thrombosis (DVT) therapy device, a passive motion machine, a pulse oximeter, or a patient lift, just to name a few examples.

It is contemplated by the present disclosure that each processing hub 150 of system 100 of FIGS. 12 and 13 is communicatively coupled to at least two locating anchors 104. The present disclosure contemplates that each locating tag 102 of the system 100 of FIGS. 12 and 13 includes a radio frequency (RF) transmitter and each locating anchor 104 includes an RF receiver. Optionally, the locating tags 102 of the system 100 of FIGS. 12 and 13 communicate with the plurality of locating anchors 104 via ultra-wideband (UWB) signals. The locations of the locating tags 102 of system 100 of FIGS. 12 and 13 are determined by the plurality of processing hubs 104 using two way ranging and time difference of arrival (TDOA) techniques. Alternatively or additionally, the locations of the locating tags 102 of system 100 of FIGS. 12 and 13 are determined by the plurality of processing hubs 150 using time of arrival (TOA) at which transmissions from the locating tags 102 are received at the plurality of locating anchors 104 or using time of flight (TOF) of transmissions between the locating tags 102 and the plurality of locating anchors 104.

In some embodiments of system 100 of FIGS. 12 and 13, each processing hub 150 of the plurality of processing hubs 150 uses signals from only a subset of the plurality of locating anchors 104 to determine the location of the locating tags 102. For example, the subset anchors 104 of system 100 of FIGS. 12 and 13 are determined based on signal strength of signals from the locating tags 102 to each locating anchor 104 of the plurality of locating anchors 104. If desired, the subset anchors 104 of system 100 of FIGS. 12 and 13 includes at least three locating anchors 104 from the plurality of locating anchors 104 having highest signal strength values as compared to others of the plurality of locating anchors 104.

As noted above, in some embodiments of system 100 of FIGS. 12 and 13, no server 106 is present. In such embodiments, the hubs 150 make the determinations regarding the locations of respective tags 102 that are in communication with the respective anchors 104 that are communicatively coupled, such as by wired connections, to the corresponding hub 150. In general, server 106 includes software that manages network resources and that serves functionality to other computer devices that are networked to the server. In contrast, hubs 150 are standalone devices that operate self-contained software to perform their dedicated functions. Servers 106 are capable of executing several software programs at once, whereas hubs 150 execute only their dedicated locating software. Thus, hubs 150 typically have less computing power than server 106 and therefore, are typically less expensive than server 106. Hubs 150 also typically have more connection ports for coupling to multiple anchors 104 as compared to the number of connection ports of server 106 which is typically coupled to network 108 via a single Ethernet cable for both transmission and receipt of network messages.

Although certain illustrative embodiments have been described in detail above, variations and modifications exist within the scope and spirit of this disclosure as described and as defined in the following claims.

The invention claimed is:

1. A caregiver rounding system comprising
a bed configured to support a patient thereon, the bed including bed circuitry, a power cord, and casters,
an equipment locating tag coupled to the bed and in communication with the bed circuitry,
a caregiver locating tag coupled to a caregiver,
a plurality of receivers mounted at fixed locations and in wireless communication with the equipment locating tag and the caregiver locating tag,
at least one computer communicatively coupled to the plurality of receivers, wherein the equipment locating tag, the caregiver locating tag, the plurality of receivers, and the at least one computer cooperate to form a high-accuracy locating system operable to determine a location of the equipment locating tag and the caregiver locating tag within at least one foot of an actual location of the equipment locating tag and the caregiver locating tag, respectively, wherein the at least one computer models a rounding zone adjacent the bed based on the location of the equipment locating tag, wherein the at least one computer determines that the caregiver has successfully completed a caregiver round if the caregiver locating tag is located within the rounding zone for a threshold period of time,
wherein the equipment locating tag changes its role from operating as an equipment locating tag to operating as an additional receiver of the plurality of receivers after determining that the bed has become stationary based on a signal from the bed circuitry indicating the occurrence of at least one or both of the following: (i) the power cord of the bed being plugged into a power outlet, and (ii) the casters of the patient bed being braked.

2. The caregiver rounding system of claim 1, wherein the rounding zone is defined as being within a boundary that is about three feet from a periphery of the bed.

3. The caregiver rounding system of claim 1, wherein the rounding zone is defined as being within a boundary calculated as being about three feet away from a footprint of the bed as theoretically projected onto a floor supporting the bed.

4. The caregiver rounding system of claim 1, wherein the rounding zone is defined as being a circular boundary having a radius of about five feet and centered on the equipment locating tag.

5. The caregiver rounding system of claim 1, wherein the threshold period of time is about five minutes.

6. The caregiver rounding system of claim 1, wherein the threshold period of time is greater than about one minute.

7. The caregiver rounding system of claim 1, wherein the equipment locating tag and the caregiver locating tag communicate with the plurality of receivers via ultra-wideband (UWB) signals.

8. The caregiver rounding system of claim 7, wherein the locations of the equipment locating tag and the caregiver locating tag is determined by the at least one computer using two way ranging and time difference of arrival (TDOA) techniques.

9. The caregiver rounding system of claim 7, wherein the locations of the equipment locating tag and the caregiver locating tag is determined by the at least one computer using time of arrival (TOA) at which transmissions from the equipment locating tag and the caregiver locating tag are received at the plurality of receivers.

10. The caregiver rounding system of claim 7, wherein the at least one computer uses signals from only a subset of the plurality of receivers to determine the location of the equipment locating tag and the caregiver locating tag, the subset being determined based on signal strength of signals from the equipment locating tag and the caregiver locating tag to the plurality of receivers.

11. The caregiver rounding system of claim 10, wherein the subset comprises at least three receivers from the plurality of receivers having highest signal strength values as compared to others of the plurality of receivers.

12. The caregiver rounding system of claim 1, wherein the bed includes a sensor that senses a presence of a patient on the bed and the at least one computer is configured to determine that a successful caregiver round has occurred only if the patient is present on the bed as sensed by the sensor.

13. The caregiver rounding system of claim 12, wherein the bed includes communication circuitry configured to transmit patient presence data for receipt by the at least one computer.

14. The caregiver rounding system of claim 12, wherein the sensor comprises a weight sensor of a weigh scale system of the bed.

15. The caregiver rounding system of claim 1, further comprising a patient locating tag coupled to a patient and the at least one computer being configured to determine that a successful caregiver round has occurred only if the patient locating tag is determined to be within the rounding zone with the caregiver locating tag for the threshold period of time.

16. A caregiver rounding system comprising
a patient locating tag coupled to a patient,
a caregiver locating tag coupled to a caregiver,
a plurality of receivers mounted at fixed locations and in wireless communication with the patient locating tag and the caregiver locating tag,
at least one computer communicatively coupled to the plurality of receivers, wherein the patient locating tag, the caregiver locating tag, the plurality of receivers, and the at least one computer cooperate to form a high-accuracy locating system operable to determine a location of the patient locating tag and the caregiver locating tag within at least one foot of an actual location of the patient locating tag and the caregiver locating tag, respectively, wherein the at least one computer models a rounding zone adjacent the patient based on the location of the patient locating tag, wherein the at least one computer determines that the caregiver has successfully completed a caregiver round if the caregiver locating tag is located within the rounding zone for a threshold period of time,
wherein at least one receiver of the plurality of receivers includes an equipment locating tag that is coupled to a bed and that changes its role from operating as an equipment locating tag to operating as an additional receiver of the plurality of receivers after determining that the bed has become stationary based on a signal from bed circuitry of the bed indicating the occurrence of at least one or both of the following: (i) a power cord of the bed being plugged into a power outlet, and (ii) casters of the patient bed being braked.

17. The caregiver rounding system of claim 16, wherein the rounding zone is defined as being within a boundary that is about three feet from the patient locating tag.

18. The caregiver rounding system of claim 16, wherein a boundary of the rounding zone is defined as a circle on a floor with the patient locating tag being situated vertically above a center of the circle.

19. The caregiver rounding system of claim 18, wherein a radius of the circle is about three feet in length.

20. The caregiver rounding system of claim 16, wherein the threshold period of time is about five minutes.

21. The caregiver rounding system of claim 16, wherein the threshold period of time is greater than about one minute.

22. The caregiver rounding system of claim 16, wherein the patient locating tag and the caregiver locating tag communicate with the plurality of receivers via ultra-wideband (UWB) signals.

23. The caregiver rounding system of claim 22, wherein the locations of the patient locating tag and the caregiver locating tag is determined by the at least one computer using two way ranging and time difference of arrival (TDOA) techniques.

24. The caregiver rounding system of claim 22, wherein the locations of the patient locating tag and the caregiver locating tag is determined by the at least one computer using time of arrival (TOA) at which transmissions from the patient locating tag and the caregiver locating tag are received at the plurality of receivers.

25. The caregiver rounding system of claim 22, wherein the at least one computer uses signals from only a subset of the plurality of receivers to determine the location of the patient locating tag and the caregiver locating tag, the subset being determined based on signal strength of signals from the patient locating tag and the caregiver locating tag to the plurality of receivers.

26. The caregiver rounding system of claim 25, wherein the subset comprises at least three receivers from the plurality of receivers having highest signal strength values as compared to others of the plurality of receivers.

27. The caregiver rounding system of claim 16, wherein the at least one computer is configured to determine that a successful caregiver round has occurred only if the patient locating tag and the caregiver locating tag are both determined to be within a patient room assigned to the patient.

28. The caregiver rounding system of claim 1, wherein the patient bed includes circuitry and further comprising a first bed transceiver carried by the patient bed and coupled to the circuitry, a second bed transceiver carried by the patient bed and coupled to the circuitry, and the caregiver locating tag communicating a tag identification (ID) to the circuitry via the first and second transceivers, the circuitry using one or more of two way ranging techniques, time difference of arrival (TDOA) techniques, or time of arrival (TOA) techniques to determine a location of the caregiver locating tag in the patient room.

29. The caregiver rounding system of claim 16, further comprising a patient bed including circuitry, a first bed transceiver carried by the patient bed and coupled to the circuitry, a second bed transceiver carried by the patient bed and coupled to the circuitry, and the caregiver locating tag communicating a tag identification (ID) to the circuitry via the first and second transceivers, the circuitry using one or more of two way ranging techniques, time difference of arrival (TDOA) techniques, or time of arrival (TOA) techniques to determine a location of the caregiver locating tag in the patient room.

30. The caregiver rounding system of claim 1, wherein the bed includes at least one sensor to monitor a bed condition and generate an alarm if the bed condition is sensed to be in an alarm state by the at least one sensor, and further comprising an equipment locating tag coupled to the bed, the plurality of receivers being in wireless communication with the equipment locating tag, and wherein the at least one computer models a patient contact zone adjacent the bed based on the location of the equipment locating tag, wherein the at least one computer signals the bed to suppress monitoring of the bed condition by the at least one sensor in response to the caregiver locating tag being detected in the patient contact zone.

31. The caregiver rounding system of claim 16, further comprising a bed configured to support the patient thereon, the bed having at least one sensor to monitor a bed condition and generate an alarm if the bed condition is sensed to be in an alarm state by the at least one sensor, an equipment locating tag coupled to the bed, the plurality of receivers being in wireless communication with the equipment locating tag, and wherein the at least one computer models a patient contact zone adjacent the bed based on the location of the equipment locating tag, wherein the at least one computer signals the bed to suppress monitoring of the bed condition by the at least one sensor in response to the caregiver locating tag being detected in the patient contact zone.

* * * * *